(12) United States Patent
Slatkine

(10) Patent No.: US 7,771,374 B2
(45) Date of Patent: Aug. 10, 2010

(54) METHOD AND APPARATUS FOR VACUUM-ASSISTED LIGHT-BASED TREATMENTS OF THE SKIN

(75) Inventor: Michael Slatkine, Herzlia (IL)

(73) Assignee: Candela Corporation, Wayland, MA (US)

( * ) Notice: Subject to any disclaimer, the term of this patent is extended or adjusted under 35 U.S.C. 154(b) by 1156 days.

(21) Appl. No.: 11/401,674

(22) Filed: Apr. 11, 2006

(65) Prior Publication Data

US 2006/0259102 A1    Nov. 16, 2006

Related U.S. Application Data

(63) Continuation-in-part of application No. 11/057,542, filed on Feb. 14, 2005, which is a continuation-in-part of application No. 10/498,382, filed on Jun. 10, 2004, which is a continuation-in-part of application No. PCT/IL02/00635, filed on Aug. 2, 2002.

(30) Foreign Application Priority Data

| Dec. 10, 2001 | (IL) | ................................. 147009 |
| Jun. 6, 2002 | (IL) | ................................. 150094 |
| Feb. 22, 2004 | (IL) | ................................. 160510 |
| Apr. 12, 2005 | (EP) | ................................. 05007952 |
| Aug. 4, 2005 | (IL) | ................................. 170132 |

(51) Int. Cl.
 *A61H 7/00* (2006.01)
(52) U.S. Cl. .................. 601/6; 601/7; 601/15
(58) Field of Classification Search ............ 606/9–10; 601/6–7, 10, 15, DIG. 1, DIG. 4, DIG. 5
See application file for complete search history.

(56) References Cited

U.S. PATENT DOCUMENTS 3,982,541 A     9/1976   L-Esperance et al.

(Continued)

FOREIGN PATENT DOCUMENTS

DE         37 30 469 A1      9/1987

(Continued)

OTHER PUBLICATIONS

Effects of Tissue Optical Clearing . . . Lasers Light within Tissue (G. Vergas & A J. Welch, "Laser in Surgery and Medicine", Supp. 13, 2001, p. 26).

(Continued)

*Primary Examiner*—Michael A. Brown
(74) *Attorney, Agent, or Firm*—Proskauer Rose LLP

(57) ABSTRACT

A method and apparatus are disclosed for enhancing the absorption of light in targeted skin structures and for the inhibition of pain transmission during light based treatments of the skin. After applying a vacuum to a vacuum chamber placed on a skin target and modulating the applied vacuum, the concentration of blood and/or blood vessels is increased within a predetermined depth below the skin surface of the skin target. Optical energy associated with light directed in a direction substantially normal to a skin surface adjoining the skin target is absorbed within the predetermined depth. The apparatus is suitable for treating vascular lesions with a reduced treatment energy density level than that of the prior art and for evacuating condensed vapors produced during the cooling of skin. The vacuum chamber may also have a skin flattening transmitting element which inhibits pain transmission upon applying a sufficiently high vacuum.

45 Claims, 50 Drawing Sheets
(2 of 50 Drawing Sheet(s) Filed in Color)

U.S. PATENT DOCUMENTS

| | | | |
|---|---|---|---|
| 4,592,353 A | 6/1986 | Daikuzono |
| 4,736,743 A | 4/1988 | Daikuzono |
| 4,838,281 A | 6/1989 | Rogers et al. |
| 4,976,709 A | 12/1990 | Sand |
| 5,057,104 A | 10/1991 | Chess |
| 5,059,192 A | 10/1991 | Zaias |
| 5,066,293 A | 11/1991 | Furumoto |
| 5,217,455 A | 6/1993 | Tan |
| 5,226,907 A | 7/1993 | Tankovich |
| 5,282,797 A | 2/1994 | Chess |
| 5,312,395 A | 5/1994 | Tan et al. |
| 5,344,418 A | 9/1994 | Ghaffari |
| 5,401,270 A | 3/1995 | Schonborn et al. |
| 5,411,502 A | 5/1995 | Zair |
| 5,429,601 A | 7/1995 | Conley et al. |
| 5,431,647 A | 7/1995 | Purcell, Jr. et al. |
| 5,449,354 A | 9/1995 | Konwitz et al. |
| 5,527,308 A | 6/1996 | Anderson et al. |
| 5,530,780 A | 6/1996 | Ohsawa |
| 5,558,660 A | 9/1996 | Dreier |
| 5,595,568 A | 1/1997 | Anderson et al. |
| 5,626,631 A | 5/1997 | Eckhouse |
| 5,630,811 A | 5/1997 | Miller |
| 5,655,547 A | 8/1997 | Karni |
| 5,735,844 A | 4/1998 | Anderson et al. |
| 5,745,519 A | 4/1998 | Ruda et al. |
| 5,814,041 A | 9/1998 | Anderson et al. |
| 5,853,407 A | 12/1998 | Miller |
| 5,871,521 A | 2/1999 | Kaneda et al. |
| 5,879,346 A | 3/1999 | Waldman et al. |
| 5,885,273 A | 3/1999 | Eckhouse et al. |
| 5,947,957 A | 9/1999 | Morris et al. |
| 5,961,475 A | 10/1999 | Guitay |
| 5,964,749 A | 10/1999 | Eckhouse |
| 6,011,890 A | 1/2000 | Neuberger |
| 6,096,029 A | 8/2000 | O'Donnell, Jr. |
| 6,120,497 A | 9/2000 | Anderson et al. |
| 6,132,392 A | 10/2000 | Stone |
| 6,142,650 A | 11/2000 | Brown et al. |
| 6,149,645 A | 11/2000 | Tobinick |
| 6,165,170 A | 12/2000 | Wynne et al. |
| 6,185,356 B1 | 2/2001 | Parker et al. |
| 6,197,020 B1 | 3/2001 | O'Donnell, Jr. |
| 6,214,034 B1 | 4/2001 | Azar |
| 6,261,310 B1 | 7/2001 | Neuberger et al. |
| 6,264,649 B1 | 7/2001 | Whitcroft et al. |
| 6,273,884 B1 | 8/2001 | Altshuler et al. |
| 6,280,438 B1 | 8/2001 | Eckhouse et al. |
| 6,508,813 B1 | 1/2003 | Altshuler |
| 6,530,920 B1 * | 3/2003 | Whitcroft et al. ............. 606/13 |
| 6,544,259 B1 | 4/2003 | Tsaliovich |
| 6,662,054 B2 | 12/2003 | Kreindel et al. |
| 7,108,689 B2 | 9/2006 | Eckhouse et al. |
| 2002/0012860 A1 | 1/2002 | Yoo |
| 2002/0013602 A1 | 1/2002 | Huttner |
| 2002/0034012 A1 | 3/2002 | Santoro et al. |
| 2002/0128600 A1 | 9/2002 | Nissels |
| 2002/0128635 A1 | 9/2002 | Altshuler et al. |
| 2002/0169442 A1 * | 11/2002 | Neev ............................ 606/9 |
| 2003/0083536 A1 | 5/2003 | Eshel et al. |
| 2004/0077977 A1 | 4/2004 | Ella et al. |
| 2004/0082940 A1 | 4/2004 | Black et al. |
| 2004/0254599 A1 | 12/2004 | Lipoma |
| 2005/0251117 A1 | 11/2005 | Anderson et al. |
| 2005/0251118 A1 | 11/2005 | Anderson et al. |
| 2005/0261584 A1 | 11/2005 | Eshel et al. |
| 2006/0189964 A1 | 8/2006 | Anderson et al. |
| 2006/0211958 A1 | 9/2006 | Rosenberg et al. |
| 2006/0241573 A1 | 10/2006 | Roersma et al. |
| 2007/0027411 A1 * | 2/2007 | Ella et al. ..................... 601/7 |
| 2007/0032763 A1 | 2/2007 | Vogel |
| 2007/0179482 A1 | 8/2007 | Anderson |
| 2007/0219532 A1 | 9/2007 | Karpowicz et al. |
| 2007/0230520 A1 | 10/2007 | Mordaunt et al. |
| 2007/0255355 A1 | 11/2007 | Altshuler et al. |

FOREIGN PATENT DOCUMENTS

| | | |
|---|---|---|
| DE | 198 49 301 | 4/2000 |
| EP | 0 103 664 B1 | 12/1982 |
| EP | 0 761 257 | 3/1997 |
| EP | 0880940 | 12/1998 |
| EP | 933.096 | 8/1999 |
| EP | 1 031 324 | 8/2000 |
| EP | 1.116.476 | 7/2001 |
| EP | 1 168 535 | 1/2002 |
| GB | 1 494 324 A | 12/1977 |
| JP | 2001-212231 | 8/2001 |
| JP | 2005-087520 | 4/2005 |
| WO | WO/99 27863 | 6/1999 |
| WO | WO 99/46005 A | 9/1999 |
| WO | WO00/60711 | 10/2000 |
| WO | WO 00 72771 | 12/2000 |
| WO | 2001/037922 | 5/2001 |
| WO | 03/103523 | 12/2003 |
| WO | 2004/004803 | 1/2004 |
| WO | 2005/009266 | 2/2005 |
| WO | 2005/112815 | 12/2005 |
| WO | 2006/052745 | 5/2006 |

OTHER PUBLICATIONS

"The Physiology Coloring Book," W. Kapit et al, Harpor Collins Publishers, 1987, pp. 88-891.
US 5,885,773, (withdrawn).

* cited by examiner

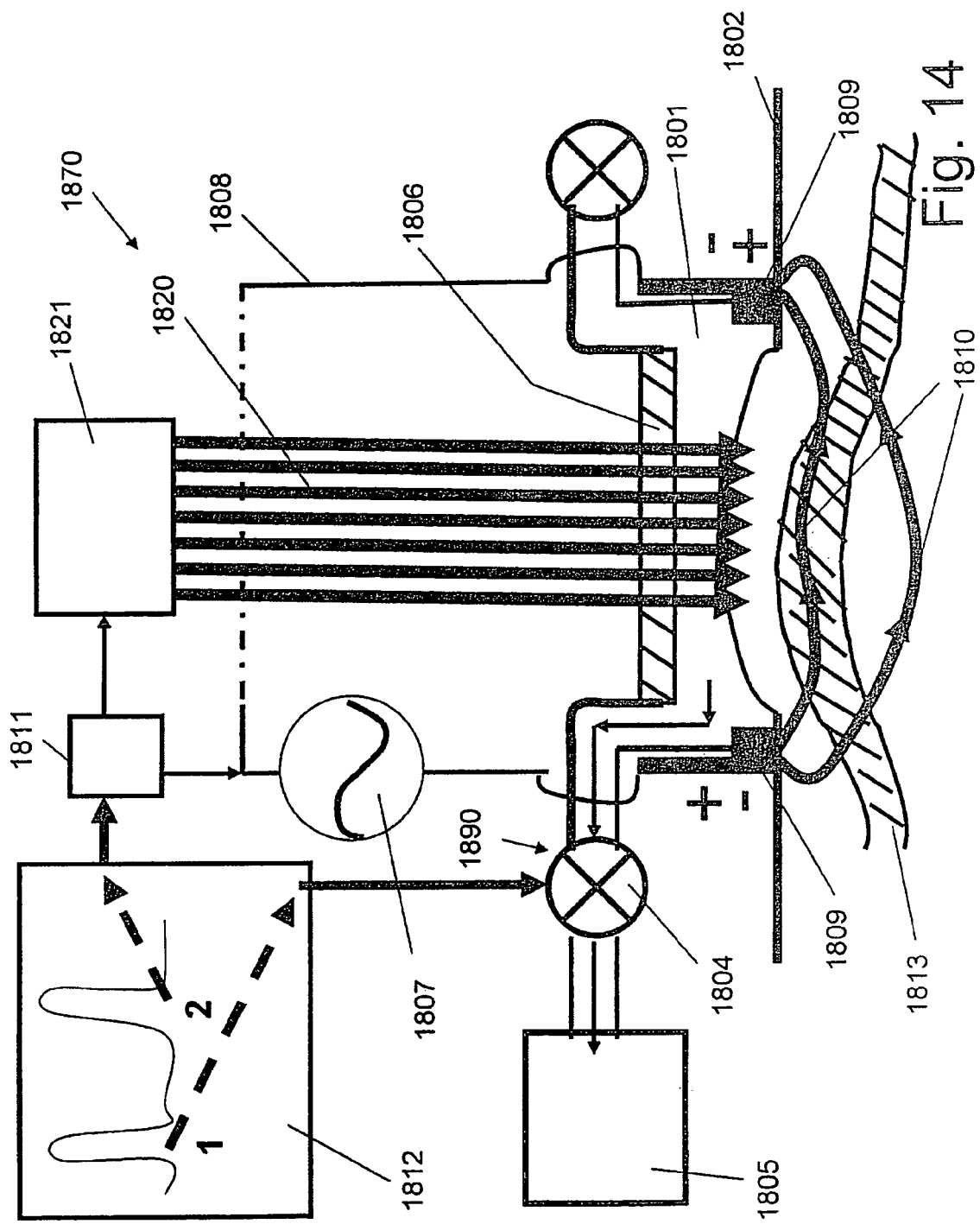

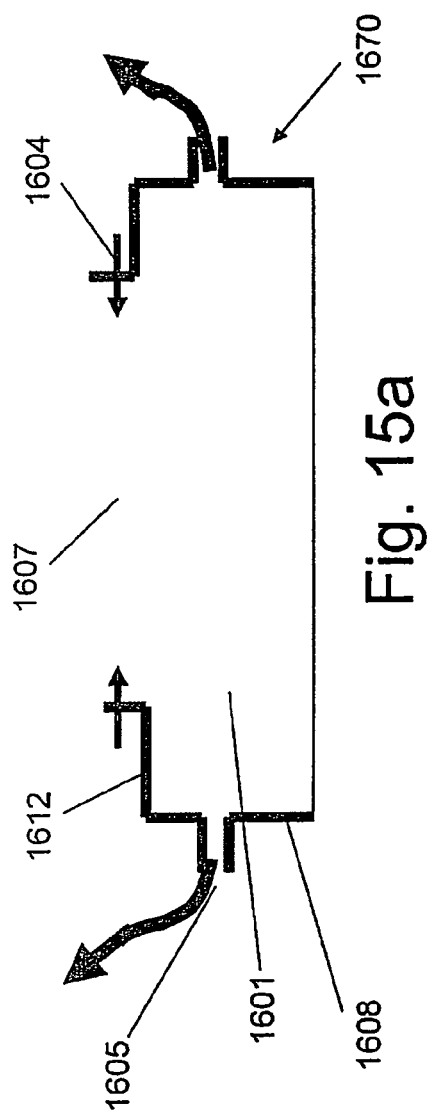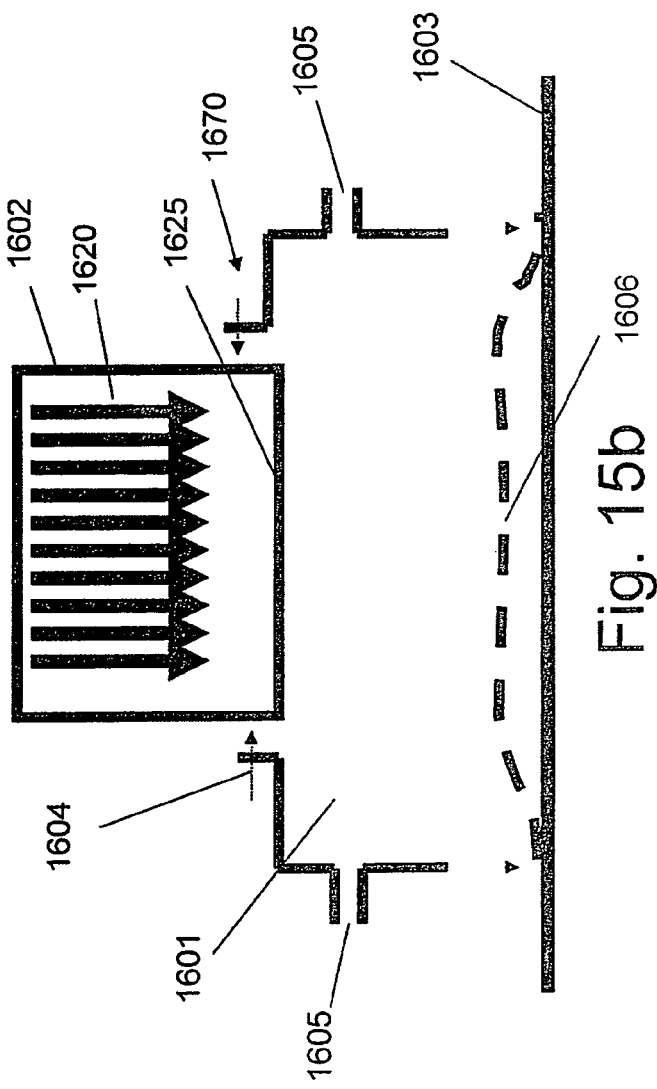

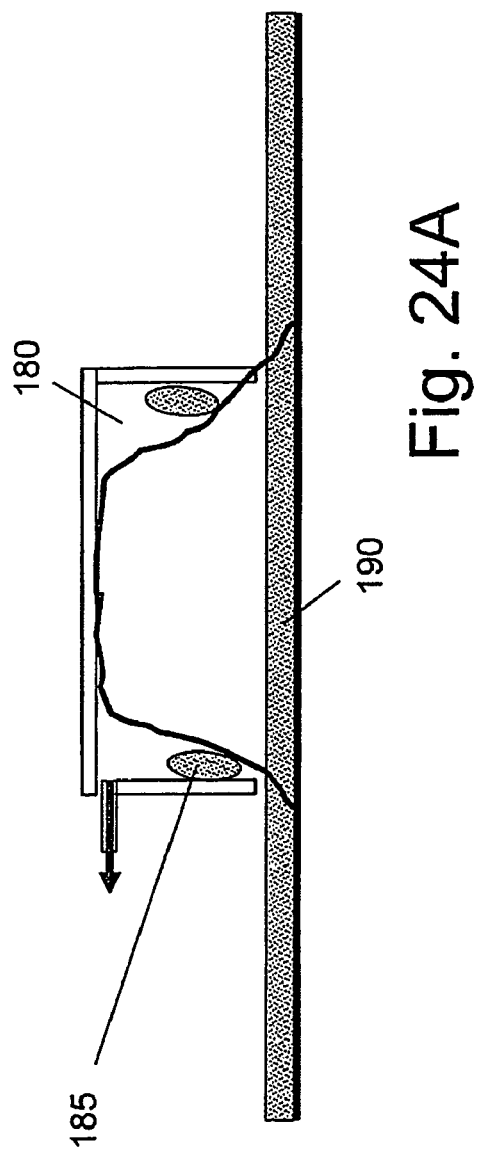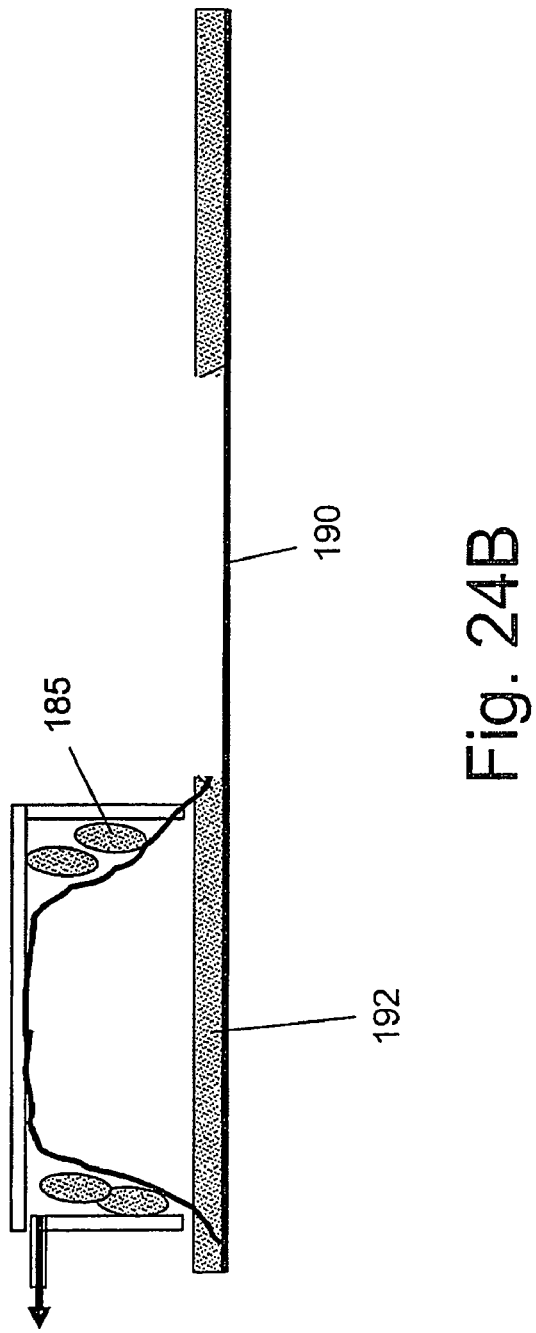

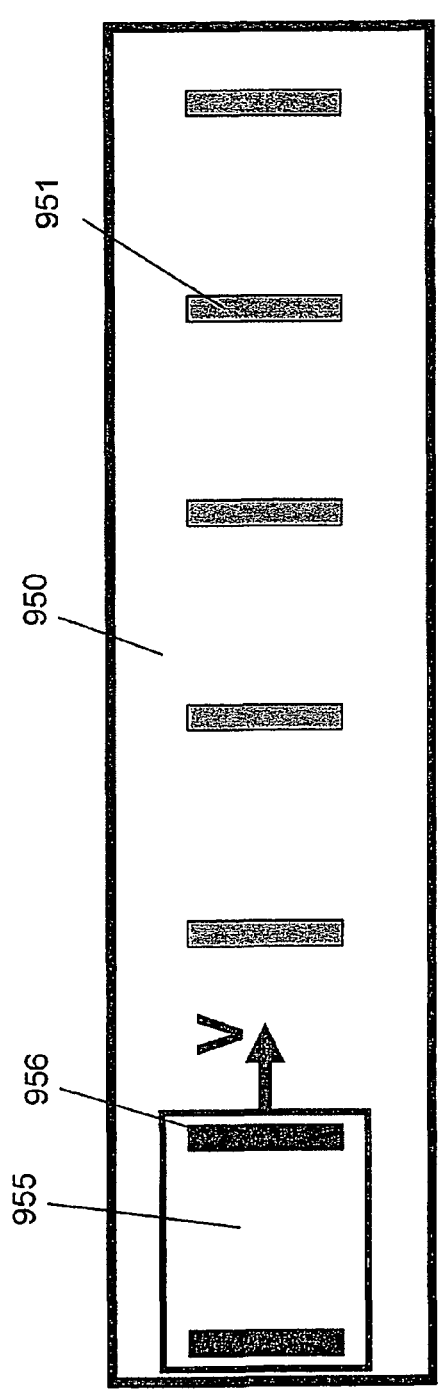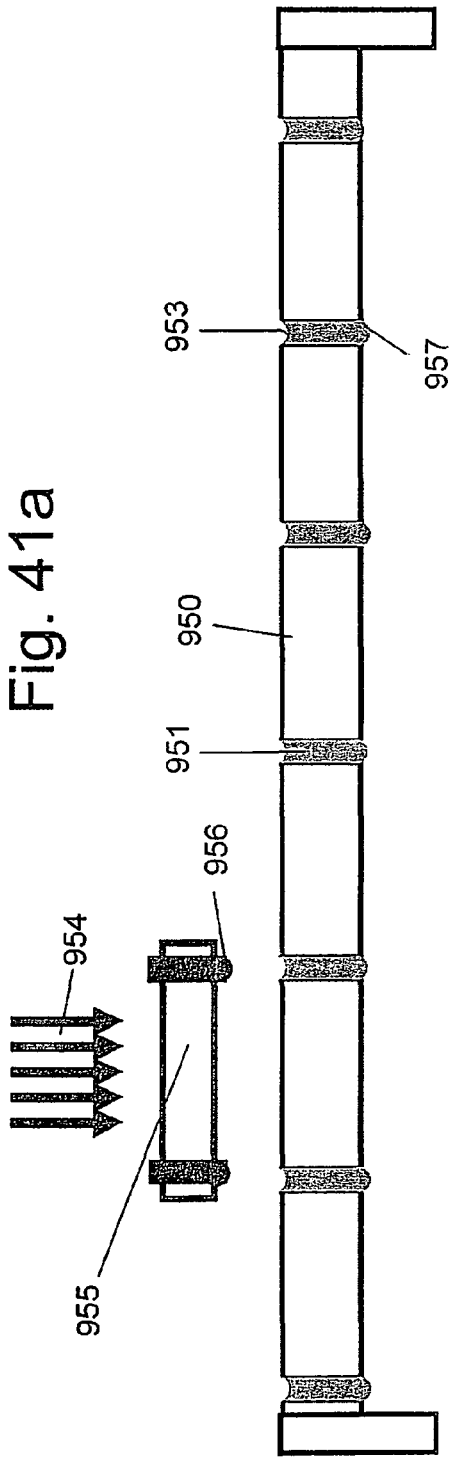
Fig. 41a
Fig. 41b

METHOD AND APPARATUS FOR VACUUM-ASSISTED LIGHT-BASED TREATMENTS OF THE SKIN

This application claims priority from EP Patent Application No. 050007952.4 (filed Apr. 12, 2005) and from IL Patent Application No. 170132 (filed Aug. 4, 2005), and is a Continuation-In-Part of U.S. patent application Ser. No. 11/057,542 (filed Feb. 14, 2005), which claims priority from Israeli Patent Application No. 160510 (filed on Feb. 22, 2004) and is a Continuation-In-Part of U.S. patent application Ser. No. 10/498,382 (filed Jun. 10, 2004), which is a Continuation-In-Part of PCT/IL02/00635 (filed on Aug. 2, 2002), which is derived from IL 147009 (filed on Dec. 10, 2001) and from IL 150094 (filed on Jun. 6, 2002).

FIELD OF THE INVENTION

The present invention is related to the field of light-based skin treatments. More specifically, the invention is related to the utilization of light sources for the non-invasive treatment of skin disorders under the skin surface, whereby light is selectively absorbed by hair shafts, blood vessels, or collagen bundles, for the treatment or destruction of unwanted hairs, of blood vessels, or of other skin disorders.

BACKGROUND OF THE INVENTION

Prior art very high intensity, short duration pulsed light systems which operate in the visible part of the spectrum, such as flashlamps or intense pulsed lasers are currently used in aesthetic treatments by one of two known ways: a) Applying the light to the skin without applying any pressure on the treatment zone, so as not to interfere with the natural absorption properties of skin; and b) Applying pressure onto the skin by means of the exit window of the treatment device in contact with the skin, thereby expelling blood from the light path within the skin and enabling better transmission of the light to a skin target in cases where the spectral lines of the treatment light source match absorption lines of the blood.

The major applications of intense pulsed light or intense pulsed laser systems are hair removal, coagulation of blood vessels for e.g. port wine stains, telangectasia, spider veins and leg veins, multiple heating of blood vessels for e.g. rosacea, treatment of pigmented skin such as erasure of black stains and sun stains or tattoo removal, and removal of fine wrinkles by heating the tissue around the wrinkles, normally referred to as photorejuvenation.

U.S. Pat. Nos. 5,226,907, 5,059,192, 5,879,346, 5,066,293, 4,976,709, 6,120,497, 6,120,497, 5,626,631, 5,344,418, 5,885,773, 5,964,749, 6,214,034 and 6,273,884 describe various laser and non-coherent intense pulsed light systems. These prior art light systems are not intended to increase the natural absorption of the skin. These prior art light systems are also not intended to block pain transmission during treatments.

Applying a vacuum to the skin is a known prior art procedure, e.g. for the treatment of cellulites, which complements massaging the skin. Such a procedure produces a flow of lymphatic fluids so that toxic substances may be released from the tissue. As the vacuum is applied, a skin fold is formed. The skin fold is raised above the surrounding skin surface, and the movement of a handheld suction device across the raised skin performs the massage. The suction device is moved in a specific direction relative to the lymphatic vessels, to allow lymphatic fluids to flow in their natural flow direction. The lymphatic valve in each lymphatic vessel prevents the flow of lymphatic fluid in the opposite direction, if the suction device were moved incorrectly. Liquids generally accumulate if movement is not imparted to the raised skin. The massage, which is generally carried out by means of motorized or hand driven wheels or balls, draws lymphatic fluids from cellulite in the adipose subcutaneous region and other deep skin areas, the depth being approximately 5-10 mm below the dermis.

U.S. Pat. No. 5,961,475 discloses a massaging device with which negative pressure is applied to the skin together during massaging. A similar massaging device which incorporates a radio frequency (RF) source for the improvement of lymphatic flow by slightly heating the adipose tissue is described in U.S. Pat. No. 6,662,054. Some massaging systems, such as those produced by Deka and Cynosure, add a low power, continuous working (CW) light source of approximately 0.1-2 W/cm$^2$, in order to provide deep heating of the adipose tissue by approximately 1-3° C. degrees and to enhance lymphatic circulation. The light sources associated with vacuum lymphatic massage devices are incapable of inducing blood vessel coagulation due to their low power. Also, prior art vacuum lymphatic massage devices are adapted to induce skin protrusion or to produce a skin fold by applying a vacuum.

Selective treatment of blood vessels by absorption of intense pulsed laser radiation is possible with Dye lasers operating at 585 nm, as well as with other types of lasers. Photorejuvenation has also been performed with Diode lasers in the near infrared spectral band of 800-980 nm and with Nd:YAG lasers having a frequency of approximately 1064 nm with limited success. The light emitted by such lasers is not well absorbed by tiny blood vessels or by the adjoining liquid. Broad band non-coherent intense pulsed light systems are also utilized for photorejuvenation with some success, although requiring more than 10 repeated treatments. The heat which is absorbed by the blood vessels, as a result of the light emitted by the intense short pulse devices, is transferred to adjacent collagen bundles.

The absorption of pulsed Diode and Nd:YAG laser beams by blood vessels is lower than the absorption of pulsed Dye laser beam. In order to compensate for limited photorejuvenation with red and infrared intense pulsed light and laser systems, a very high energy density as high as 30-60 J/cm$^2$ needs to be generated. At such an energy density, the melanin-rich epidermis, particularly in dark skin, is damaged if not chilled. A method to reduce the energy density of intense pulsed lasers or non-coherent intense pulsed light sources which operate in the visible or the near infrared regions of the spectrum will thereforebe beneficial.

Pulsed dye lasers operating in the yellow spectral band of approximately 585-600 nm, which is much better absorbed by blood vessels, are also utilized for the smoothing of fine wrinkles. The energy density of light emitted by Dye lasers, which is approximately 3-5 J/cm$^2$, is much lower than that of light emitted by other lasers. However, the pulse durations of light emitted by Dye lasers are very short, close to 1 microsecond, and therefore risk the epidermis in darker skin. Treatments of wrinkles with Dye lasers are slow, due to the low concentration of absorbing blood vessels, as manifested by the yellow or white color of treated skin, rather than red or pink characteristic of skin having a high concentration of blood vessels. Due to the low energy density of light emitted by Dye lasers, as many as 10 treatments may be necessary. A method to reduce the energy density of light generated by Dye lasers, or to reduce the number of required treatments at currently used energy density levels, for the treatment of fine wrinkles, would be beneficial.

Pulsed Dye lasers operating at 585 nm are also utilized for the treatment of vascular lesions such as port wine stains or telangectasia or for the treatment of spider veins. The energy density of the emitted light is approximately 10-15 J/cm$^2$, and is liable to cause a burn while creating the necessary purpura. A method to reduce the energy density of light emitted by Dye lasers for the treatment of vascular lesions would be highly beneficial.

Hair removal has been achieved by inducing the absorption of infrared light, which is not well absorbed by melanin present in hair strands, impinging on blood vessels. More specifically, absorption of infrared light by blood vessels at the distal end of hair follicles contributes to the process of hair removal. High intensity pulsed Nd:YAG lasers, such as those produced by Altus, Deka, and Iridex, which emit light having an energy density of more than 50 J/cm$^2$, are used for hair removal. The light penetration is deep, and is often greater than 6 millimeters. Some intense pulsed light or pulsed laser systems, such as that produced by Syneron, used for hair removal or photorejuvenation also employ an RF source for further absorption of energy within the skin.

The evacuation of smoke or vapor, which is produced following the impingement of monochromatic light on a skin target, from the gap between the distal end window of a laser system and the skin target, is carried out in conjunction with prior art ablative laser systems such as $Co_2$, Erbium or Excimer laser systems. The produced smoke or vapor is usually purged by the introduction of external fresh air at greater than atmospheric pressure.

Coagulative lasers such as pulsed dye lasers or pulsed Nd:YAG lasers, which treat vascular lesions under the skin surface without ablating the skin surface, are generally not provided with an evacuation chamber which produces subatmospheric pressure over a skin target.

Some prior art intense pulsed laser systems, which operate in the visible and near infrared region of the spectrum and treat lesions under the skin surface, e.g. vascular lesions, with pulsed dye laser systems or pulsed Nd:YAG lasers, employ a skin chilling system. Humidity generally condenses on the distal window, due to the use of a skin chilling system. The humidity is not caused by the skin treatment, but rather by the low temperature of the distal window. It would be advantageous to evacuate the condensed vapors from the distal window of the laser system prior to the next firing of the laser.

U.S. Pat. Nos. 5,595,568 and 5,735,844 describe a coherent laser system for hair removal whereby pressure is applied to the skin by a transparent contact device in contact therewith, in order to expel blood present in blood vessels from a treatment zone. In this approach blood absorption decreases in order to increase subcutaneous light penetration.

U.S. Pat. Nos. 5,630,811 and 5,853,407 also describe a coherent laser system for hair removal which restricts local blood flow, in order to reduce damage to the skin tissue surrounding the hairs. Local tissue structures are flattened by applying positive pressure or negative pressure to the skin. The treatment beam is limited to only 5 mm. The treatment beam is not suitable for a larger treatment spot per pulse of approximately 40 mm. Also, the pressure level which has to be applied is not recited, although different pressures levels will lead to different effects. Some of these effects cannot be achieved with a beam diameter of 5 mm or less, as will be described hereinafter. Blood expulsion resulting from the pressing of skin is not uniform and is not instantaneous for such large treatment spots, and therefore blood may remain in the skin tissue after the laser beam has been fired. Also, a large-diameter treatment device may not be easily repositioned to another treatment site, due to the relatively high lifting force needed when negative pressure is applied to the skin. Furthermore, this laser system does not provide any means for preventing gel obstruction when negative pressure is applied to the skin. Although applying a flattening positive pressure or negative pressure to a small-diameter treatment area enhances hair removal, the treatment of vascular lesions is not improved since fewer blood vessels are present within the treatment area due to the blood expulsion. A need therefore exists for a vacuum-assisted device that can alternatively reduce or increase the blood volume fraction within a skin target.

US 2002/0128635 discloses a head for applying light energy to a selected depth in a scattering medium having an outer layer in physical and thermal contact with the head. The head includes a thermally conductive block having an energy emitting surface and at least one laser diode mounted in the block adjacent the energy emitting surface. At the bottom of the block is attached a transparent element having a high reflectivity mask with slits, for optimizing retroreflection of scattered energy from the skin. In one embodiment, the block is formed with a recess therein, into which a vacuum draws the skin. The head is not easily repositioned to another treatment site in order to treat a large-area skin surface, due to the relatively high lifting force needed when the vacuum is applied to the skin. Furthermore, means are not provided for preventing gel obstruction when a vacuum is applied to the skin.

The light-based non-ablative treatment of hair or of vascular lesions is often very painful, particularly during the treatment of dark and thick unwanted hairs which may appear in a bikini line, on the legs, or on the back. A pain sensation is felt with almost all types of light based devices for hair removal, including intense pulsed light sources and lasers.

The aforementioned prior art efforts to expel blood vessels help in some cases to avoid unnecessary damage to skin structures which are not intended to be treated, such as unnecessary coagulation of blood vessels during a hair removal treatment, while increasing hair removal efficacy. The reduction in damage to skin structures does not alleviate the immediate pain sensed during a treatment, but rather, the expulsion of blood causes a higher exposure of the hair shaft to a treatment pulse of light, resulting in a higher hair follicle temperature and a correspondingly higher level of acute pain due to excessive heating of the nerves which surround the hair shafts. Furthermore, the expelling of blood from one skin area increases the fractional blood volume in adjacent areas, causing a risk of thermal damage if the treatment light diffuses to the adjacent blood rich zone. It is well known to light-based hair removal practitioners that acute pain is felt during the treatment when hairy areas, particularly characterized by dark thick hair, are impinged by the treatment beam, whereas firing the light beam on a hairless area is substantially painless. It can therefore be concluded that the pain which is sensed during a hair removal treatment is generated by nerves surrounding the hair shafts, and not by nerves distributed in other areas of the skin. There is therefore a need for an improved apparatus for pain reduction without having to reduce the treatment energy density.

According to the Gate Theory of Afferent Inhibition described in, for example, "The Physiology Coloring Book," W. Kapit et al, Harper Collins Publishers (1987), pages 88-89, the pressure sensed by large, fast-conducting tactile nerves, such as by rubbing the skin, limits the transmission gates in the dorsal horn, excludes access for the weaker pain signal, and therefore inhibits the pain signal transmission by pain nerves in the spinal cord. During light-based skin treatments, pain nerves in the vicinity of the epidermis and adjacent to hair follicles sense a relatively high increase in temperature of the hair follicle, often greater than 70° C. If not inhibited, the pain nerves transmit a pain signal to the brain via the spinal cord. Due to sensed pain, the treatment time is considerably increased.

Two types of a pain sensation caused by light-based aesthetic treatments are recognizable: immediate sharp pain and long term milder pain. The immediate sharp pain is felt during each treatment pulse and increases to an intolerable sensation after a few shots, necessitating a patient to rest during a long delay before continuing the treatment. The treatment rate, particularly for large areas such as on the legs, is therefore considerably reduced. Depending on his pain tolerance, the patient may even decide not to continue the treatment. The sharp pain is caused by the exposure of treatment light to nerve endings located in the epidermis and dermis, by sensory receptors of hair shafts located deep in the dermis, or by the stimulation of nerves surrounding the hair bulbs as the hair shafts are being heated during the treatment, often at a temperature of approximately 70° C.

The less acute, long term milder pain is caused by the accumulative increase of skin temperature following treatment, e.g. during a period ranging from 10 minutes to a day after treatment, which is approximately 3 to 5° C. above body temperature. The increase in skin temperature may induce redness and edema, causing pain, depending on the hair density and the fractional blood volume within the adjoining tissue. The application of a cold gauze immediately after the treatment usually helps to avoid the post-treatment pain.

The most common prior art method for alleviating or preventing the immediate sharp pain caused by the non-ablative treatment of hair or of vascular lesions with intense pulsed light is the application of EMLA cream produced by AstraZeneca Canada Inc. Such cream is a topical anesthetic applied to the skin approximately 30-60 minutes before a treatment, which numbs the skin and decreases the sensation of pain. This prior art method is generally impractical due to the long and inconvenient waiting time between the application of the EMLA cream and the treatment. Since health professionals prefer to maximize the number of patients to be treated during a given time period, the health clinic must provide a large waiting room for those patients that are waiting to be treated by intense pulsed light following the application of the EMLA cream.

Pain caused by the non-ablative treatment of hair or of vascular lesions may also be alleviated or prevented by reducing the energy density of the intense pulsed light. Energy density reduction, however, compromises the treatment quality, and therefore is an unacceptable solution, particularly due the relatively high cost of treatment.

U.S. Pat. Nos. 6,264,649 and 6,530,920 disclose a cooling head for a skin treatment laser and a method to reduce or eliminate pain during laser ablative treatments of the skin by cooling the skin surrounding the treatment area. The pain is associated with the ablation or burning of a skin surface during skin resurfacing. An extraction port of the cooling head enables removal of debris material, such as smoke produced by the skin treatment laser, from the treatment area and for connection to a vacuum source. Evacuated vapor such as smoke is replaced by fresh and clean air.

With respect to prior art smoke evacuation devices, a significant subatmospheric pressure is generally not generated over a skin surface due to the introduction of fresh atmospheric pressure air. If subatmospheric pressure were maintained over a skin surface, the treatment handpiece would be prevented from being lifted and displaced from one skin site to another during the treatment process. Additionally, prior art smoke evacuation devices are not associated with non-ablative lasers, such as a long-pulse Nd:YAG laser, which treat tissue only under the skin surface and do not produce smoke resulting from the vaporization of the skin surface. Furthermore, the application of heat releasing gel onto a skin target is not conducive for the ablation of a skin surface or for the subsequent evacuation of debris material since the gel forms a barrier between the skin surface and the surrounding air.

Current laser and IPL skin treatment systems utilize chilling means. However, pain is still noticeable.

A need therefore exists for alleviating the resulting pain caused by the treatment of unwanted hair, unwanted wrinkles or vascular lesions by intense pulsed light or intense pulsed laser systems, without reducing the light source intensity, without applying a topical anesthetic, and without using a chiller as means to reduce pain.

It is an object of the present invention to provide a method and apparatus for the treatment of subcutaneous lesions, such as vascular lesions, by a non-ablative, high intensity pulsed laser or light system operating at wavelengths shorter than 1800 nm which does not damage the surface of the skin or the epidermis.

It is an object of the present invention to provide a method and apparatus for controlling the depth of subcutaneous light absorption.

It is an object of the present invention to provide a method and apparatus for increasing the absorption of light which impinges a skin target by increasing the concentration of blood vessels thereat.

It is an additional object of the present invention to provide a method and apparatus by which the energy density level of intense pulsed light that is suitable for hair removal, fine wrinkle removal, including removal of wrinkles around the eyes and in the vicinity of the hands or the neck, and the treatment of port wine stain or rosacea may be reduced relative to that of the prior art.

It is an additional object of the present invention to provide a method and apparatus by which the number of required treatments for hair removal, fine wrinkle removal, including removal of wrinkles around the eyes and in the vicinity of the hands or the neck, and the treatment of port wine stain or rosacea at currently used energy density levels may be reduced relative to that of the prior art.

It is yet an additional object of the present invention to provide a method and apparatus for repeated evacuation, prior to the firing of a subsequent light pulse, of vapors which condense on the distal window due to the chilling of laser treated skin.

It is yet an additional object of the present invention to provide a method and apparatus for alleviating the resulting pain caused by the treatment of unwanted hair, unwanted wrinkles or vascular lesions by intense pulsed light or intense pulsed laser systems, without reducing the light source intensity, without applying a topical anesthetic, and without relying on skin chilling for pain reduction.

It is yet an additional object of the present invention to provide a method and apparatus for speedy repositioning of a vacuum-assisted, non-ablative light-based treatment handpiece from one site to another.

It is yet an additional object of the present invention to provide a method and apparatus for a vacuum-assisted, light-based skin treatment which is conducive for the application of a heat releasing gel onto a skin surface, without resulting in obstruction of vacuum generating apparatus.

It is a further object of the present invention to provide an apparatus for vacuum-assisted, light-based treatment which can be held by one hand while a light treatment handpiece is held by the other hand.

Other objects and advantages of the invention will become apparent as the description proceeds.

SUMMARY OF THE INVENTION

The present invention is directed to apparatus for vacuum-assisted light-based skin treatments. The apparatus comprises a vacuum chamber which is transparent or translucent to intense pulsed monochromatic or non-coherent light directed to a skin target. A vacuum is applied to said vacuum chamber, whereby said skin target is drawn to said vacuum chamber. The efficacy and utility of the apparatus are achieved by employing the apparatus in two modes: (a) in a vacuum applying mode wherein a high vacuum level ranging from 0-1 atmospheres is attained and (b) in a vacuum release mode upon deactivation of the light source and of the vacuum pump after optical energy associated with the directed light has been absorbed within a predetermined depth under the skin surface, wherein atmospheric air is introduced to the vacuum chamber so that the vacuum chamber may be speedily repositioned to another skin target.

In one embodiment of the invention, the apparatus comprises:
a) a non-ablative intense pulsed monochromatic or non-coherent light source;
b) a vacuum chamber placeable on a skin target which has an opening on the distal end thereof and provided with a transmitting element on the proximate end thereof, said transmitting element being transparent or translucent to light generated by said source and directed to said skin target;
c) means for applying a vacuum to said vacuum chamber, the level of the applied vacuum suitable for drawing said skin target to said vacuum chamber via said opening; and
d) means for preventing influx of air into vacuum chamber during a vacuum applying mode.

As referred to herein, "distal" is defined as a direction towards the exit of the light source and "proximate" is defined as a direction opposite from a distal direction.

As referred to herein, the term "transmitting element" includes an element through which electromagnetic energy suitable for effecting a desired treatment is transmitted to a selected skin target. When the electromagnetic energy is light, the transmitting element is an optical element. When the electromagnetic energy is RF energy, the transmitting element may be metallic.

The terms "evacuation chamber" and "vacuum chamber" as referred to herein are interchangeable.

As referred to herein, a "vacuum level" is the absolute pressure below atmospheric pressure. A vacuum level of 500 mmHg is therefore a pressure of 500 mmHg below atmospheric pressure. When a vacuum level is referred to as being greater than a given value, e.g. greater than 400 mmHg, the pressure therein is an absolute pressure of a value below atmospheric pressure greater than said given value.

The vacuum chamber is advantageously one-hand graspable by means of a handle connected thereto so that the vacuum chamber can be held by one hand while a light treatment handpiece is held by the other hand.

Preferably—
a) the vacuum applying means comprises a vacuum pump and at least one control valve;
b) the wavelength of the light ranges from 400 to 1800 nm;
c) the pulse duration of the light ranges from 10 nanoseconds to 900 msec;
d) the energy density of the light ranges from approximately 2 to approximately 150 J/cm$^2$;
e) the level of applied vacuum within the vacuum chamber ranges from approximately 0 to approximately 1 atmosphere;
f) the light source is selected from the group of Dye laser, Nd:YAG laser, Diode laser, light emitting diode, Alexandrite laser, Ruby laser, Nd:YAG frequency doubled laser, Nd:Glass laser, a non-coherent intense pulse light source, and a non-coherent intense pulse light source combined with an RF source or with a monopolar or bipolar RF source;
g) the light is suitable for hair removal, collagen contraction, photorejuvenation, treatment of vascular lesions, treatment of sebacouse or sweat glands, treatment of warts, treatment of pigmented lesions, treatment of damaged collagen, skin contraction, treatment of acne, treatment of warts, treatment of keloids, treatment of sweat glands, treatment of psoriasis, and treatment of lesions pigmented with porphyrins or with cyanin green;
h) the light is suitable for the treatment of vascular lesions selected from the group of port wine stains, telangectasia, rosacea, and spider veins;
i) the transmitting element is suitable for transmitting the light in a direction substantially normal to a skin surface adjoining said skin target;
j) the transmitting element is separated from the adjoining skin surface by a gap ranging from 0.5 to 50 mm, and preferably approximately 2 mm;
k) the treatment spot per pulse is greater than 5 mm, and preferably between 15 to 50 mm;
l) the influx of air into vacuum chamber during a vacuum applying mode is prevented by means of a control valve and control circuitry or by means of manual occlusion of a vacuum chamber conduit;
m) the ratio of the maximum length to maximum width of the aperture formed on the distal end of the vacuum chamber ranges from approximately 1 to 4;
n) the vacuum chamber has at least one suction opening, the vacuum being applied to the vacuum chamber via said at least one suction opening;
o) the vacuum chamber is U-shaped; and
p) the vacuum chamber is provided with a rim for sealing the peripheral contact area between the skin surface adjoining the skin target and the vacuum chamber wall.

Preferably, the apparatus further comprises control means for controlling operation of the vacuum pump, the at least one control valve, and the light source. The control means is selected from the group of electronic means, pneumatic means, electrical means, and optical means. The control means may be actuated by means of a finger depressable button, which is positioned on a light treatment handpiece.

In one aspect, the control means is suitable for firing the light source after a first predetermined delay, e.g. from approximately 0.5 sec to approximately 4 seconds, following operation of the vacuum pump.

In one aspect, the control means is suitable for firing the light source after a predetermined delay following opening of the at least one control valve.

In one aspect, the control means is suitable for increasing the pressure in the vacuum chamber to atmospheric pressure following deactivation of the light source, to allow for effortless repositioning of the vacuum chamber to a second skin target. The increase in vacuum chamber pressure may be triggered by means of a light detector which transmits a signal to the control means upon sensing a significant decrease in optical energy generated by the light source or may be effected after a second predetermined delay, following deactivation of the light source.

In one aspect, the control means is suitable for verifying that a desired energy density level of the light is being directed to the skin target and for deactivating the light source if the energy density level is significantly larger than said desired level.

In one aspect, the vacuum chamber is connected to, or integrally formed with, a proximately disposed handpiece through which light propagates towards the skin target. The vacuum chamber has a proximate cover formed with an aperture, said cover being attachable or releasably attachable to a handpiece such as a light guide having an integral transmitting element.

In one aspect, the vacuum pump is an air pump.

In one aspect, the vacuum pump is a pump, e.g. a peristaltic pump, for drawing air and gel from the interior of the vacuum chamber via a hose connected to a conduit in communication with the interior of the vacuum chamber. The hose provides indication means that the skin target has undergone a light-based treatment by means of gel which is discharged from an end of the hose onto a skin surface during a vacuum applying mode.

In one aspect, the apparatus further comprises means to stabilize the vacuum chamber on a substantially non-planar skin surface.

In one aspect, the apparatus further comprises a skin contact detector for sensing the placement of the vacuum chamber onto the skin target and for generating a first signal to activate the vacuum pump following placement of the vacuum chamber onto the skin target.

In one aspect, the control valve is opened following generation of a second signal by means of a light detector which is adapted to sense termination of the light directed to the skin target, atmospheric pressure air thereby being introduced to the interior of the vacuum chamber.

In one aspect, the second signal is suitable for deactivating the vacuum pump.

In another embodiment of the invention, the apparatus further comprises an array of vacuum chambers placeable on a skin surface. The array is formed from a single sheet made of material which is transparent or translucent to the light, said sheet being formed with a plurality of conduits for air evacuation such that each of said conduits is in communication with a corresponding vacuum chamber. The distance between adjacent vacuum chambers is sufficiently small to allow light which has diffused from the interior of each chamber to treat a skin area located underneath a corresponding conduit.

Each conduit preferably branches into first and second portions which are in communication with a vacuum pump and with a source of compressed air, respectively.

In one aspect, each vacuum chamber is provided with a contact detector for triggering a signal to activate the vacuum pump, two control valves to control the passage of fluid through the corresponding first and second conduits portions, respectively, and a light detector which generates a signal to introduce compressed air through the corresponding second conduit portion upon sensing the termination of the light directed to the skin target.

In one aspect, the first conduit portions are arranged such that the air from all vacuum chambers is evacuated simultaneously upon activation of the vacuum pump.

In another embodiment of the invention, the vacuum applying means comprises a vertically displaceable cover to which the transmitting element is secured and chamber walls which surround, and are of a similar shape as, said cover, a vacuum being generated within a vacuum chamber defined by the volume between said cover, said walls, and the skin target upon proximal displacement of said cover relative to said walls. The means for preventing influx into the vacuum chamber is a sealing element which is secured to the outer periphery of the cover and resiliently contacts the chamber walls.

In one aspect, a proximally directed force or distally directed force is generated by any means selected from the group of a plurality of solenoids, a spring assembly, and a pneumatic device, or a combination thereof, which are deployed around the periphery of the cover and connected to the walls, and is controllable so as to adjust the height of the drawn skin target relative to the adjoining skin surface. Due to their low power consumption, a 1.5 V battery may be used to energize the solenoids.

The apparatus preferably further comprises an aeration tube for introducing atmospheric air to the vacuum chamber during a vacuum release mode. The aeration tube is in communication with a valve which is actuated upon conclusion of a skin target treatment.

In one aspect, the proximally directed force is supplemented by means of a vacuum pump.

In another embodiment of the invention, the apparatus comprises means for preventing passage of skin cooling gel to the vacuum applying means.

In one aspect, the means for preventing passage of gel to the vacuum applying means comprises a trap, a first conduit through which gel and air are drawn from the vacuum chamber to said trap, a second conduit through which air is drawn from said trap to the vacuum pump, and optionally, a filter at the inlet of the first and second conduits.

In one aspect, the trap is suitable for the introduction therein of an ion exchange resin with which the gel is boundable.

In one aspect, the means for preventing passage of gel is a detachable vacuum chamber upper portion, detachment of said upper portion allowing removal of gel retained within the vacuum chamber interior. Suitable apparatus comprises an upper portion having an open central area, a transmitting element attached to said upper portion, vacuum chamber walls, a vacuum chamber cover perpendicular to said walls and suitably sized so as to support said upper portion, and a plurality of attachment clips pivotally connected to a corresponding vacuum chamber wall for detachably securing said upper portion to said vacuum chamber cover.

In one aspect, the vacuum chamber walls are coated with a hydrophobic material. Accordingly, the vacuum chamber provides indication that the skin target has undergone a light-based treatment by means of gel which falls to the skin surface during a vacuum release mode in the shape of the distal end of the vacuum chamber walls.

In one aspect, the at least one suction opening is sufficiently spaced above the distal end of a vacuum chamber wall and from the centerline of the vacuum chamber so as to prevent obstruction of the at least one suction opening by gel and drawn skin upon application of the vacuum.

In another embodiment of the invention, the apparatus further comprises means for skin cooling, said skin cooling means adapted to reduce the rate of temperature increase of the epidermis at the skin target. The level of the applied vacuum is suitable for evacuating condensed vapors which are produced within the gap between the transmitting element and the skin target and condense on the transmitting element during the cooling of skin.

In one aspect, the skin cooling means is a metallic plate in abutment with the vacuum chamber on the external side thereof, said plate being cooled by means of a thermoelectric cooler. The plate may be positionable on the skin surface adjoining said skin target in order to cool the lateral sides of the vacuum chamber or may be in contact with the transmitting element.

In one aspect, the skin cooling means is a polycarbonate layer transparent to the directed light which is attached to the distal face of the transmitting element.

In one aspect, the skin cooling means is a gel, a low temperature liquid or gas applied onto the skin target.

In another embodiment of the invention, the apparatus is suitable for controlling the depth of light absorption by blood vessels under a skin surface, comprising:

a) a vacuum chamber placed on a skin target which is formed with an aperture on the distal end thereof and provided with a transmitting element on the proximate end thereof, said transmitting element being transparent or translucent to intense pulsed monochromatic or non-coherent light directed to said skin target and suitable for transmitting the light in a direction substantially normal to a skin surface adjoining said skin target;

b) means for applying a vacuum to said vacuum chamber, the level of the applied vacuum suitable for drawing said skin target to said vacuum chamber via said aperture; and c) means for inducing an increase in the concentration of blood and/or blood vessels within a predetermined depth below the skin surface of said skin target, optical energy associated with the directed light being absorbed within said predetermined depth.

As referred to herein, the term "blood volume fraction" is interchangeable with "the concentration of blood and/or blood vessels within a predetermined depth below the skin surface".

In one embodiment, the means for inducing an increase in the concentration of blood and/or blood vessels within a predetermined depth below the skin surface of said skin target is a means for modulating the applied vacuum.

The depth under the skin surface at which optical energy is absorbed may be selected in order to thermally injure or treat predetermined skin structures located at said depth. As referred to herein, a "skin structure" is defined as any damaged or healthy functional volume of material located under the epidermis, such as blood vessels, collagen bundles, hair shafts, hair follicles, sebaceous glands, sweat glands, adipose tissue. Depending on the blood concentration within the skin target, the light may propagate through the skin surface and upper skin layers without being absorbed thereat and then being absorbed at a skin layer corresponding to that of a predetermined skin structure. As referred to herein, the term "light" means both monochromatic and non-coherent light. The terms "light absorption" and "optical energy absorption" refer to the same physical process and are therefore interchangeable.

In contrast with a prior art vacuum-assisted apparatus for laser or intense pulsed light treatment wherein a sharp skin fold is produced through a slit following application of the vacuum, vacuum-assisted drawn skin by means of the apparatus of the present invention is not distorted, but rather is slightly and substantially uniformly drawn to the vacuum chamber, protruding approximately 1-2 mm from the adjoining skin surface. The maximum protrusion of the drawn skin from the adjoining skin surface is limited by a transmitting element defining the proximate end of the vacuum chamber. The transmitting element is separated from the adjoining skin surface by a gap of preferably 2 mm, and ranging from 0.5-50 mm. In one embodiment of the invention, the drawn skin abuts the transmitting element.

As referred to herein, "vacuum modulation" means adjustment of the vacuum level within, or of the frequency by which vacuum is applied to, the vacuum chamber. By properly modulating the vacuum, the blood flow rate, in a direction towards the vacuum chamber, within blood vessels at a predetermined depth below the skin surface can be controlled. As the concentration of blood and/or blood vessels is increased within the skin target, the number of light absorbing chromophores is correspondingly increased at the predetermined depth. The value of optical energy absorbence at the predetermined depth, which directly influences the efficacy of the treatment for skin disorders, is therefore increased.

Preferably— a) The wavelength of the light ranges from 400 to 1800 nm.
b) The pulse duration of the light ranges from 10 nanoseconds to 900 msec.
c) The energy density of the light ranges from 2 to 150 $J/cm^2$.
d) The ratio of the maximum length to maximum width of the aperture formed on the distal end of the vacuum chamber ranges from approximately 1 to 4.
e) The level of the applied vacuum within the vacuum chamber ranges from 0 to 1 atmosphere.
f) The frequency of vacuum modulation ranges from 0.2 to 100 Hz.
g) The light is fired after a predetermined delay following application of the vacuum.
h) The predetermined delay ranges from approximately 10 msec to approximately 1 second.
i) The duration of vacuum application to the vacuum chamber is less than 2 seconds.
j) Vacuum modulation is electronically controlled.

In one embodiment of the invention, the means for inducing an increase in the concentration of blood and/or blood vessels within a predetermined depth below the skin surface of said skin target is at least one support element positioned at a skin area adjoining the skin target and having a thickness suitable for inducing an increase in the concentration of blood and/or blood vessels within said predetermined depth. The apparatus may further comprise at least one leg having a thickness considerably less than the at least one support element and positioned at the periphery of the vacuum chamber, said at least one leg being separated from an adjacent support element, the at least one support element being adapted to urge blood expelled by said at least one leg towards the skin target.

The predetermined depth under the skin surface at which optical energy is absorbed is selected in order to thermally injure or treat predetermined skin structures located at said depth.

Due to implementation of the apparatus, the treatment energy density level for various types of treatment is significantly reduced, on the average of 50% with respect with that associated with prior art devices. The treatment energy density level is defined herein as the minimum energy density level which creates a desired change in the skin structure, such as coagulation of a blood vessel, denaturation of a collagen bundle, destruction of cells in a gland, destruction of cells in a hair follicle, destruction of unwanted lesions by means of photodynamic therapy, or any other desired effects. The following is the treatment energy density level for various types of treatment performed with use of the present invention:

a) treatment of vascular lesions, port wine stains, telangectasia, rosacea, and spider veins with light emitted from a dye laser unit and having a wavelength of 585 nm: 5-12 $J/cm^2$;

b) treatment of vascular lesions, port wine stains, telangectasia, rosacea, and spider veins with light emitted from a diode laser unit and having a wavelength of 940 nm: 10-30 J/cm$^2$;

c) treatment of vascular lesions with light emitted from an intense pulsed non-coherent light unit and having a wavelength of 570-900 nm: 5-20 J/cm$^2$;

d) photorejuvination with light emitted from a dye laser unit and having a wavelength of 585 nm: 1-4 J/cm$^2$;

e) photorejuvination with light emitted from an intense pulsed non-coherent light unit and having a wavelength of 570-900 nm: 5-20 J/cm$^2$;

f) photorejuvination with a combined effect of light emitted from an intense pulsed non-coherent light unit and having a wavelength of 570-900 nm and of a RF source: 10 J/cm$^2$ for both the intense pulsed non-coherent light unit and RF source;

g) hair removal with light emitted from a Nd:YAG laser unit and having a wavelength of 1604 nm: 25-35 J/cm$^2$; and h) Porphyrin-based photodynamic therapy with light emitting diodes delivering blue light (420 nm), orange light (585 nm), or red light (630 nm): 5-20 J/cm$^2$.

The preferably further comprises a control unit for controlling operation of the vacuum applying means and light source. The control unit is also suitable for controlling operation of at least one control valve in communication with the vacuum chamber, for firing the light after a predetermined delay following application of the vacuum, and for electronically modulating the vacuum.

In one aspect, the apparatus further comprises a skin contact detector for sensing the placement of the vacuum chamber onto the skin target, the control unit being suitable for activating the vacuum applying means in response to a signal transmitted by said skin contact detector.

In one aspect, the apparatus further comprises a light detector for sensing the termination of the light directed to the skin target, the control unit being suitable for regulating a control valve in response to a signal transmitted by said light detector so as to introduce atmospheric pressure air to the interior of the vacuum chamber.

In one aspect, the apparatus further comprises a pulsed radio frequency (RF) source for directing suitable electromagnetic waves to the skin target. The frequency of the electromagnetic waves ranges from 0.2-10 MHz. The RF source is either a bipolar RF generator which generates alternating voltage applied to the skin surface via wires and electrodes or a monopolar RF generator with a separate ground electrode. The control unit is suitable for transmitting a first command pulse to the at least one control valve and a second command pulse to both the intense pulsed light source and RF source.

In one aspect, the apparatus further comprises an erythema sensor, said sensor suitable for measuring the degree of skin redness induced by the vacuum applying means. The control unit is suitable for controlling, prior to firing the light source, the energy density of the light emitted from the light source, in response to the output of the erythema sensor.

In one aspect, the vacuum chamber has a proximate cover formed with an aperture, said cover being attachable to a handpiece, such as a light guide, having an integral transmitting element.

In one aspect, the apparatus further comprises means for skin cooling, said skin cooling means adapted to reduce the rate of temperature increase of the epidermis at the skin target.

In one aspect, the apparatus further comprises means for preventing passage of skin cooling gel to the vacuum applying means.

In another embodiment of the invention, the apparatus is suitable for alleviating or preventing pain caused by a non-ablative light-based treatment of a targeted skin structure. Accordingly, the gap separating said the transmitting element from the skin surface adjoining said the skin target and the magnitude of the proximally directed force resulting from said the applied vacuum in combination are suitable for drawing said the skin target to said the vacuum chamber via the opening on the distal end of the vacuum chamber said aperture until said the skin target contacts said the transmitting element; and the control means is suitable for firing the light source after the first predetermined delay, following operation of the vacuum applying means.

In one aspect, the apparatus is suitable for causing the skin target to contact the transmitting element for a duration equal to, or greater than, the first predetermined delay, whereby pain signals generated by the nervous system during the treatment of the skin structure are alleviated or prevented.

The control means is preferably suitable for controlling the vacuum level generated by the vacuum applying means, and has a plurality of finger depressable buttons, each of which being adapted to set the vacuum applying means and light source at a unique combination of operating conditions so as to generate a predetermined vacuum level within the vacuum chamber and to fire the light source after a predetermined time delay following the operation of the vacuum applying means.

In one aspect, a single light source and vacuum pump are operable in conjunction with differently configured vacuum chambers, for example a vacuum chamber that is suitable for pain alleviation or a vacuum chamber that is suitable for inducing an increase in blood concentration within a skin target. Each differently configured vacuum chamber is releasably attachable to a treatment light handpiece, e.g. by means of suitable threading or clips.

In another embodiment of the invention, a dermatological vacuum pump is provided which is in fluid communication with a vacuum chamber placeable on a gel coated skin area and provided with a transmitting element transparent or translucent to pulsed light suitable for effecting a light-based dermatological treatment on the proximate end thereof and with an opening on the distal end thereof.

The pump comprises an eccentrically rotating rotor having an outer profile of generally equilateral triangular shape with convexly curved faces terminating at an apex, wherein each of said faces is formed with a central face slot adjacent to the centerline of the corresponding face and substantially parallel thereto; and a casing formed with an epitrochoidal inner wall defining a cavity in which said rotor rotates and being configured such that the apexes of said rotor are in contact with said wall throughout the eccentric angular displacement of said rotor.

Variably sized compartments defined by the volume within said cavity between said inner wall and a corresponding face of said rotor and through which controlled volumes of air and gel drawn from said vacuum chamber are sequentially transferable to a pump discharge, following operation of said pump, are established. Each of said compartments increases from a first volume to a second volume in an intake-expansion cycle to generate a vacuum in said vacuum chamber, decreases from said second volume to a third volume in a compression-exhaust cycle to discharge air and gel. A corresponding rotor face in the vicinity of a central face slot is flexible upon reaction to the force applied thereto by gel that is pressurized within a corresponding compartment during a compression-exhaust cycle.

The pump is capable of simultaneously evacuating both gel and air from the vacuum chamber, despite the very high pressure generated within the pump by the incompressible gel. The pump is also capable of evacuating any other liquid having slight or considerable viscosity from the vacuum chamber, when such a viscous liquid is used to conduct heat from a skin area during a light-based treatment. When the term "gel" is referred to hereinafter, a viscous liquid will be included by reference as well.

The casing is formed with an inlet in communication with a conduit through which air and gel are drawn from the interior of the vacuum chamber to the pump cavity and with an outlet through which the air and gel are discharged to an exhaust tube. The pump preferably further comprises an exhaust pipe larger in size than the exhaust tube.

The vacuum pump preferably further comprises means for restoring the pressure within the vacuum chamber to atmospheric pressure, e.g. within approximately 0.1 second. The vacuum chamber pressure is restored to atmospheric pressure by reversing the rotational direction of the pump, in order to deliver atmospheric-pressure air to the vacuum chamber.

The vacuum pump is preferably capable of evacuating air and gel from said vacuum chamber for at least 500 treatment cycles, each of said treatment cycles being characterized by a vacuum generating step, a treatment firing step, and a vacuum release step, and of generating, during each of said treatment cycles, a vacuum level within said vacuum chamber which is suitable for drawing said skin area to said vacuum chamber via said opening.

The vacuum level generated within the vacuum chamber is preferably greater than 500 mm Hg. The evacuation rate of the vacuum pump is sufficiently high to allow the completion of a treatment cycle at each treatment site within 3 seconds, and preferably 1-3 seconds, 2-3 seconds, or even less than one second.

The vacuum pump preferably further comprises means for limiting the vacuum level generated within the vacuum chamber. The vacuum level generated within the vacuum chamber is limited by means of remaining atmospheric-pressure not discharged through the exhaust tube or exhaust pipe, said remaining atmospheric-pressure air being transferable to the inlet and mixable with the air drawn from the vacuum chamber. The vacuum level generated within the vacuum chamber is limited to approximately 0.05-0.1 atmospheres.

The vacuum pump preferably further comprises means for the rotor to conform to the shape of the casing. Such means comprises an end face slot formed in each rotor face in the vicinity of a corresponding apex. Each of the end face slots is substantially perpendicular to the corresponding face and divides the same into a relatively small portion and a relatively long portion such that said relatively small portion is flexible upon contact of a corresponding apex with a first region of the inner casing wall whereat the gap of the rotor cavity is of a different dimension than at a second region of the inner casing wall.

The power consumption of a motor adapted to drive a shaft on which the rotor is mounted preferably ranges from approximately 1 to 10 W.

The vacuum pump preferably further comprises a pump cover and bottom which remain essentially in sealing abutment with the casing throughout each treatment cycle.

The rotor, casing, cover and bottom are preferably made from a self-lubricating material such as polymeric material, e.g. a mixture of approximately 70% Acetal and approximately 30% Teflon which has a coefficient of friction of approximately 0.05.

In one aspect, the rotor, casing, cover and bottom are made of steel.

The vacuum pump preferably further comprises a sealing ring surrounding the top and bottom covers and a sealing disc interposed between each of the top and bottom covers.

The pump volume is preferably no greater than 25 $cm^3$ and therefore the conduit has a length of no greater than 10 cm.

The present invention is also directed to a dermatological handpiece system, comprising:
a) a vacuum chamber placeable on a gel coated skin area and provided with a transmitting element transparent or translucent to pulsed light suitable for effecting a light-based dermatological treatment on the proximate end thereof and with an opening on the distal end thereof;
b) a handpiece body attached to said vacuum chamber;
c) a vacuum pump housed in said handpiece body, comprising an eccentrically rotating rotor having an outer profile of generally equilateral triangular shape with convexly curved faces terminating at an apex such that each of said faces is formed with a central face slot adjacent to the centerline of the corresponding face and substantially parallel thereto, and a casing formed with an epitrochoidal inner wall defining a cavity in which said rotor rotates and being configured such that the apexes of said rotor are in contact with said wall throughout the eccentric angular displacement of said rotor;
d) a conduit in fluid communication with said vacuum chamber and a first port of said pump cavity;
e) an exhaust tube in communication with a second port of said pump cavity
f) a bidirectional motor for driving said pump rotor;
g) a control unit for said motor;
h) a power source for said motor and said control unit; and
i) means in electrical communication with said power source for activating and deactivating said motor,
wherein variably sized compartments defined by the volume within said cavity between said inner wall and a corresponding face of said rotor and through which controlled volumes of air and gel drawn from said vacuum chamber via said conduit are sequentially transferable to said exhaust tube, following activation of said motor, are established,
wherein each of said compartments increases from a first volume to a second volume in an intake-expansion cycle to generate a vacuum in said vacuum chamber, decreases from said second volume to a third volume in a compression-exhaust cycle to discharge air and gel,
wherein a corresponding rotor face in the vicinity of a central face slot is flexible upon reaction to the force applied thereto by gel that is pressurized within a corresponding compartment during a compression-exhaust cycle.

In one aspect, the control unit, following reception of a suitable command, is capable of reversing the rotational direction of the motor and consequently of the rotor, in order to deliver atmospheric-pressure air to the vacuum chamber.

In one aspect, gel discharged from the exhaust tube to a skin area constitutes indication means that a skin target has undergone a light-based treatment.

In one aspect, the means for activating and deactivating the motor are at least one sensor in electrical communication with the control unit.

In one aspect, the handpiece body has a sufficiently small size, low weight and ergonometric design so as to prevent operator fatigue when intermittently held by one hand of an operator for more than one hour during repeated repositioning thereof to different skin areas.

In one embodiment, the handpiece body further houses the light source. Accordingly, the control unit is adapted to control the operation of both the vacuum pump and of the light source, and is therefore suitable for synchronizing in sequence a vacuum generating step, a treatment firing step, and a vacuum release step for each treatment cycle of a corresponding skin area.

The control unit is suitable for synchronizing a predetermined delay ranging from approximately 0.5 sec to approximately 4 seconds between the activation of the vacuum pump and the firing of the source, in order to ensure that a drawn skin area will be in contact with the clear transmitting element of the vacuum chamber for a sufficiently long nerve inhibiting duration after the light source is fired.

The control unit is also suitable for increasing the pressure in the vacuum chamber to atmospheric pressure by reversing the polarity of the motor following deactivation of the light source.

In one embodiment, an apparatus for alleviating or preventing pain caused by a treatment with electromagnetic energy of a targeted skin structure comprises:
 a) an element subjected to a generated vacuum therebelow, the level of the generated vacuum being sufficiently high to draw a skin target underlying said element towards, and in a compressing relation against, said element, whereby to alleviate or prevent the transmission of a pain signal generated by pain receptors located within said skin target; and
 b) a pulsed source of electromagnetic energy for generating waves that are transmitted through said element and that are suitable for treating a skin disorder within said skin target.

In one embodiment, an apparatus for alleviating or preventing pain caused by a light-based treatment of a targeted skin structure comprises:
 a) a non-ablative intense pulsed monochromatic or non-coherent light source for generating any spectral band of light having a wavelength ranging from 400 to 1800 nm;
 b) a vacuum chamber placed on a skin target which is formed with an aperture on the distal end thereof and provided with a transmitting element on the proximate end thereof, said transmitting element being transparent or translucent to the light generated by said light source and suitable for transmitting the light in a direction substantially normal to a skin surface adjoining said skin target; and
 c) a vacuum pump for applying a vacuum to said vacuum chamber, the level of the applied vacuum suitable for drawing said skin target through said aperture towards, and in a compressing relation against, said transmitting element, whereby to alleviate or prevent the transmission of a pain signal generated by pain receptors located within said skin target.

In one aspect, the apparatus further comprises gliding apparatus for displacing a light source distal end over the transmitting element at a speed ranging from 0.3 to 40 cm/sec.

In one aspect, the apparatus further comprises a scanner for scanning by means of said generated light substantially the entire area of the skin target which underlies the transmitting element at a repetition rate of up to 5 pulses/sec.

In one aspect, the apparatus further comprises a pressure sensor in communication with the interior of the vacuum chamber for determining whether the applied vacuum level is sufficient to inhibit the transmission of pain signals.

In one aspect, the apparatus further comprises a skin contact detector for sensing the placement of the vacuum chamber onto the skin target.

In one aspect, the apparatus is suitable for evacuating air and gel from the vacuum chamber.

In one aspect, the vacuum pump is a rotary pump, such as one that has an eccentrically rotating rotor having an outer profile of generally equilateral triangular shape with convexly curved faces terminating at an apex, each of said faces being formed with a central face slot adjacent to the centerline of the corresponding face and substantially parallel thereto.

In one aspect, the transmitting element is chilled.

In one aspect, the apparatus further comprises means for centering a light source distal end with respect to, and above, walls of the vacuum chamber.

In one aspect, the apparatus further comprises means for repositioning the vacuum chamber to another skin target without gaps or overlaps.

In one aspect, the apparatus further comprises an electronic control unit which is suitable for:
 a) receiving a first signal from the skin contact sensor upon placement of the vacuum chamber onto the skin target;
 b) transmitting a second signal to a vacuum pump actuator to operate the vacuum pump and to initiate a vacuum applying mode;
 c) receiving a third signal from a pressure sensor in communication with the interior of the vacuum chamber when the applied vacuum level is sufficient to inhibit the transmission of pain signals;
 d) transmitting a fourth signal to a light source controller to trigger operation of the light source or to enable triggering of the light source;
 e) receiving a fifth signal from an optical sensor which is adapted to detect the deactivation of the light source; and
 f) transmitting a sixth signal to the vacuum pump actuator to initiate a vacuum release mode.

In one aspect, the apparatus further comprises a dissolving solution pump in fluid communication with a dissolving solution reservoir and with a conduit connected to a vacuum pump discharge, for cleaning and dissolving accumulated gel. Accordingly, the control unit is further adapted to transmit a seventh signal to a dissolving solution pump actuator to activate the dissolving solution pump following a predetermined number of cycles of the vacuum applying and vacuum release mode.

In one embodiment, a method of painless hair removal comprises the steps of:
 a) positioning a rigid surface above a selected skin target;
 b) applying a vacuum of a sufficient value over said skin target such that the latter is flattened and compressed against said rigid; and
 c) firing a source of light which is suitable for a hair removal treatment such that the light is directed to said skin target and hair is removed, whereby pain signals generated by the nervous system during the hair removal treatment are inhibited due to the contact of said skin target onto said rigid surface.

In one embodiment, a method for the painless removal of tattoos or of pigmented lesions comprises the steps of:
 a) positioning a rigid surface above a selected skin target;
 b) applying a vacuum of a sufficient value over said skin target such that the latter is flattened and compressed against said rigid surface; and
 c) firing a source of light which is suitable for a tattoo or a pigmented lesion removal treatment such that the light is directed to said skin target and hair is removed, whereby pain signals generated by the nervous system during the tattoo or pigmented lesion removal treatment are inhibited due to the contact of said skin target onto said rigid surface.

In one embodiment, a method for alleviating or preventing pain caused by a non-ablative light-based treatment of a targeted skin structure comprises:
- a) providing a vacuum chamber having an aperture on the distal end thereof and a transmitting element on the proximate end thereof which is transparent to light suitable for effecting a desired treatment with respect to a selected skin structure;
- b) placing said vacuum chamber on a skin target in the vicinity of said skin structure;
- c) automatically applying a vacuum of a sufficient level to said vacuum chamber following step b) such that said skin target is drawn by the proximally directed force resulting from said vacuum through said aperture and contacts said transmitting element;
- d) directing a distal end of the light source to said skin target;
- e) firing the light source after a predetermined delay following step c) such that the light is directed to said skin structure and effects a desired treatment, whereby pain signals generated by the nervous system during the treatment of said skin structure are alleviated or prevented due to the contact and compression of said skin target onto said transmitting element for a duration equal to or longer than said predetermined delay;
- f) automatically releasing the vacuum from the vacuum chamber following deactivation of the light source;
- g) optionally, repositioning the vacuum chamber to the vicinity of another skin target;
- h) directing the distal end of the light source to said another skin target; and
- i) repeating steps c), e) and f).

In one aspect, the step of directing the distal end of the light source to another skin target is performed by gliding the light source distal end over the transmitting element.

In one aspect, the step of directing the distal end of the light source to another skin target is performed by means of a scanner.

In one aspect, the delay ranges from approximately 0.5 sec to approximately 4 seconds.

In one aspect, the light source is an intense pulsed monochromatic or non-coherent light source.

In one aspect, the light is in any optical band in the spectral range of 400 to 1800 nm.

In one aspect, the desired treatment is selected from the group of hair removal, treatment of vascular lesions, collagen contraction, tattoo removal, and treatment of pigmented lesions.

In one aspect, the vacuum level ranges from approximately 0 to 1 atmosphere.

In one aspect, the duration of the applied vacuum ranges from 0.1 to 6 seconds.

In one embodiment, an apparatus for the treatment of skin disorders comprises:
- a) a vacuum chamber placeable on a skin target which has an opening on the distal end thereof and provided with a transmitting element on the proximate end thereof;
- b) means for applying a vacuum to said vacuum chamber, the level of the applied vacuum suitable for drawing said skin target to said vacuum chamber via said opening and for inducing an increase in the concentration of blood and/or blood vessels below the skin surface of said skin target; and
- c) a light source suitable for emitting light which is transmitted through said vacuum chamber and propagates through said skin target, and for treating a skin disorder present on said skin target.

In one embodiment, an apparatus for the treatment of skin disorders comprises:
- a) a vacuum chamber placeable on a skin target which has an opening on the distal end thereof and provided with a transmitting element on the proximate end thereof;
- b) means for applying a vacuum to said vacuum chamber, the level of the applied vacuum suitable for drawing said skin target to said vacuum chamber via said opening and for inducing a change in spectral properties of said skin target; and
- c) a light source suitable for emitting light which is transmitted through said vacuum chamber and propagates through said skin target, and for treating a skin disorder present on said skin target.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings:

FIG. 14 schematically illustrates another embodiment of the invention which employs both an intense pulsed light source and a radio frequency source, for improved coagulation of blood vessels;

FIGS. 15a and 15b schematically illustrate a vacuum chamber which is attachable to a light guide, wherein FIG. 15a illustrates the vacuum chamber prior to attachment and FIG. 15b illustrates the vacuum chamber following attachment;

FIGS. 24A and 24B schematically illustrate the accumulation of gel as a vacuum chamber is displaced from skin area to another;

FIGS. 41a and 41b illustrate top and side views, respectively, of a vacuum chamber transmitting element which is provided with another configuration of bipolar RF-assisted metallic conducting electrodes that facilitate a gliding apparatus;

DETAILED DESCRIPTION OF PREFERRED EMBODIMENTS

The present invention is directed to apparatus which is provided with a unit for evacuating vapors, such as condensed vapors that were produced during the chilling of skin prior to the firing of the laser unit. The evacuation unit comprises a U-shaped vacuum chamber through which monochromatic or intense pulsed light passes as it is directed to a skin target, and a vacuum pump. During operation of the vacuum pump, the vacuum level within the vacuum chamber is increased by occluding a conduit of the vacuum chamber e.g. by a finger of the operator. As vacuum is applied to the skin target, skin is drawn toward the vacuum chamber and the concentration of blood vessels in the vicinity of the target increases. The added concentration of blood vessels increases the absorption of light within the tissue, and therefore facilitates treatment of a skin disorder.

Figure 1:
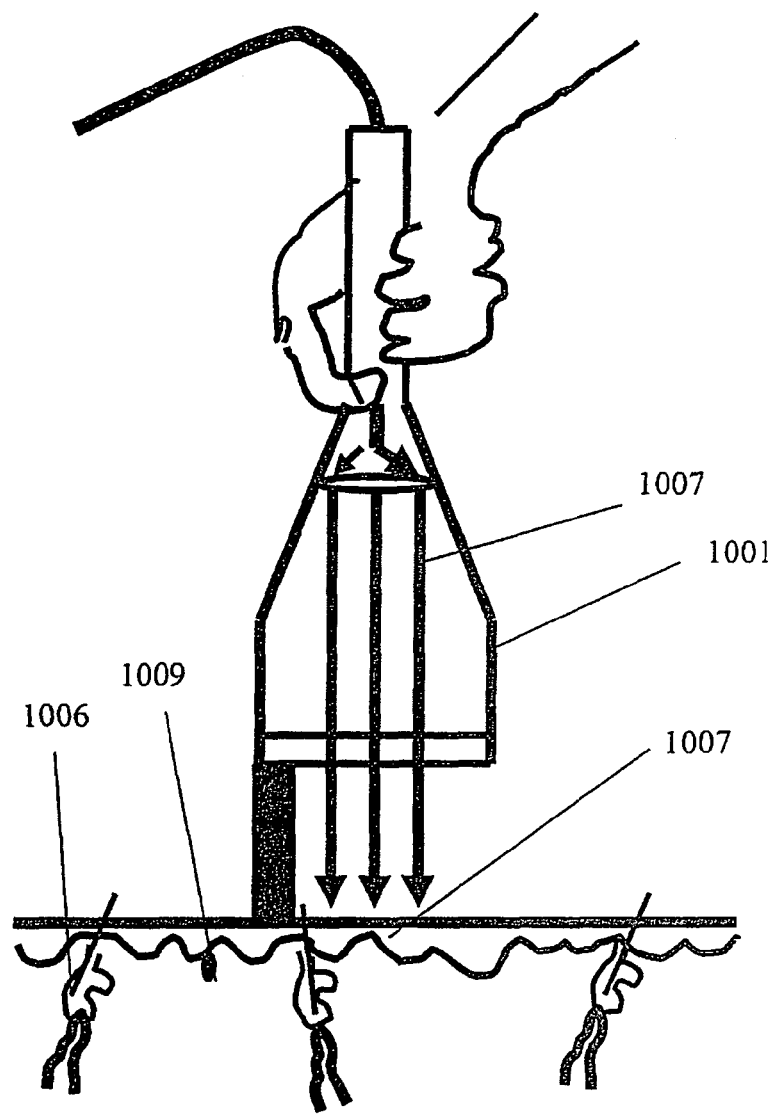
FIG. 1 is a schematic drawing which illustrates the propagation of an intense pulsed laser beam from a handpiece to a skin target according to a prior art method.

FIG. 1 illustrates the propagation of an intense pulsed laser beam the wavelength of which is in the visible or near infrared region of the spectrum, i.e. shorter than 1800 nm, from the distal end of a handpiece to a skin target according to a prior art method. Handpiece 1001 comprises transmitting element 1002, such as a lens or a window, which transmits monochromatic beam 1007 emitted from the laser unit and impinges skin target 1004. The beam penetrates skin target 1004 and selectively impinges a subcutaneous skin structure to be thermally injured, such as collagen bundle 1005, blood vessel 1009, or hair follicle 1006. In this method, external pressure or vacuum is not applied to the skin.

Figure 2:
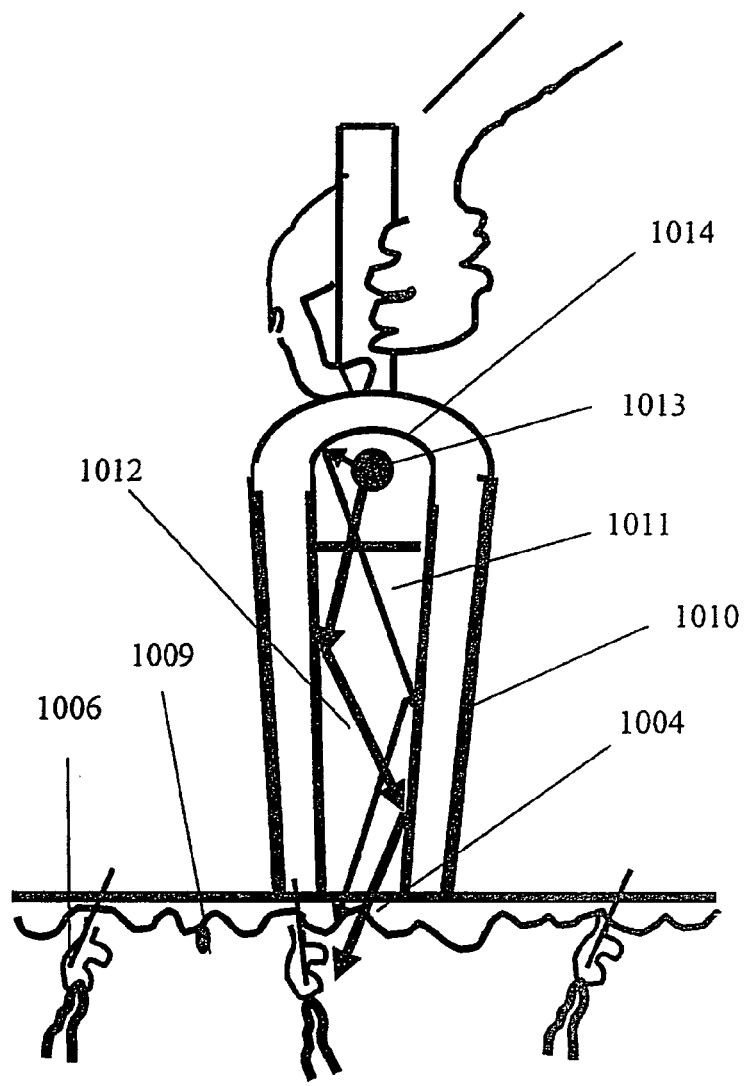
FIG. 2 is a schematic drawing which illustrates the propagation of an intense pulsed non-coherent light beam from a handpiece to a skin target according to a prior art method.

FIG. 2 illustrates a prior art non-coherent intense pulsed light system from which light is fired to a skin target for e.g. treatment of vascular lesions, hair removal, or photorejuvenation. Handpiece 1010 comprises light guide 1011 which is in contact with skin target 1004. Beam 1012, which is generated by lamp 1013 and reflected from reflector 1014, is non-coherent and further reflected by the light guide walls. In some handpieces, such as those produced by Deka (Italy), a transmitting element is utilized, rather than a light guide. Chilling gel is often applied to the skin when such a light system is employed. In this method, external pressure or vacuum is not applied to the skin, and the handpiece is gently placed on the skin target, so as to avoid removal of the gel layer, the thickness of which is desired to remain at approximately 0.5 mm.

Figure 3:
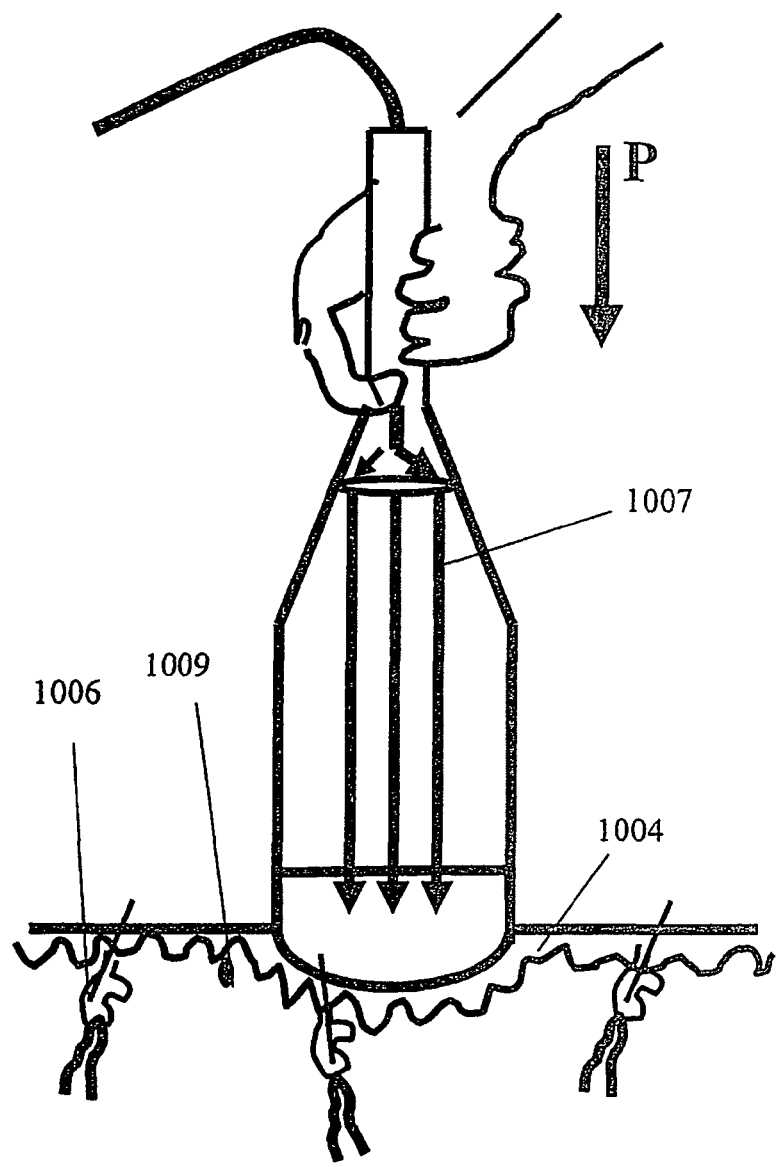
FIG. 3 is a schematic drawing of a prior art treatment method by which pressure is applied to a skin target, in order to expel blood from those portions of blood vessels which are in the optical path of subcutaneously scattered light.

FIG. 3 illustrates a prior art laser system similar to those of U.S. Pat. Nos. 5,595,568 and 5,735,844, which employs an optical component 1022 at the distal end thereof in contact with skin target 1004. Pressure is applied to skin target 1004, in order to expel blood from those portions of blood vessels 1025, as schematically illustrated by the arrows, which are in the optical path of subcutaneously scattered light, thereby allowing more monochromatic light to impinge hair follicle 1006 or collagen bundle 1005. Concerning hair removal, melanin is generally utilized as an absorbing chromophore.

Figure 4:
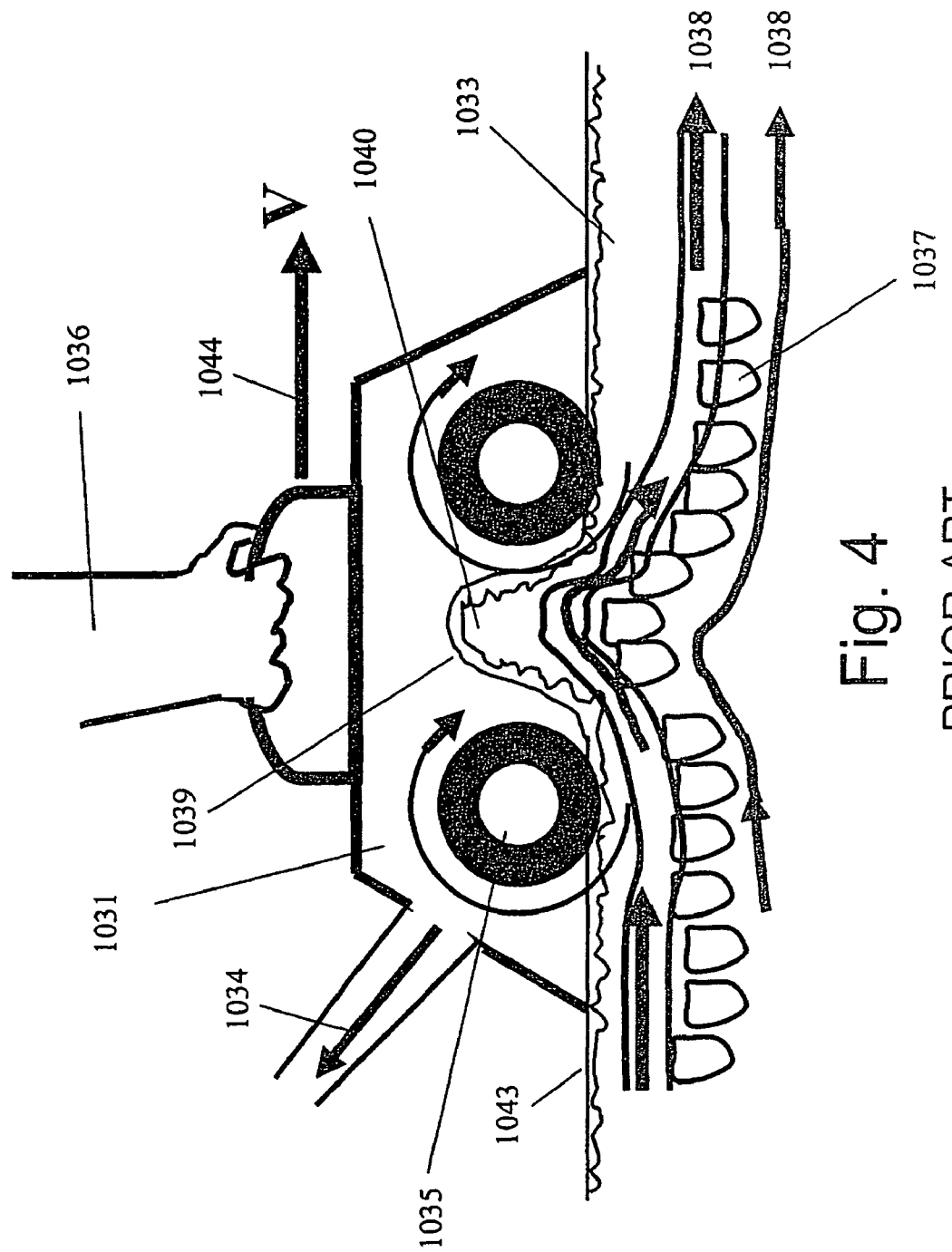
FIG. 4 is a schematic drawing of a prior art vacuum-assisted rolling cellulite massage device.

FIG. 4 illustrates a prior art device 1031, such as that produced by LPG (France), which is in pressing contact with skin 1033 in order to perform a deep massage of cellulite adipose layer 1037. Device 1031 is formed with a convex surface 1039 in a central region of its planar skin contacting surface 1043. Device 1031 stimulates the flow of lymphatic fluids in their natural flow direction 1038 in order to remove toxic materials from the adjoining tissue. The stimulation of lymphatic fluid flow is achieved by applying a vacuum to the interior of device 1031 so that air is sucked therefrom in the direction of arrow 1034 of the skin. The application of the vacuum draws skin toward convex surface 1039 and induces the temporary formation of skin fold 1040, which is raised in respect to adjoining skin 1033. Due to the elasticity of skin, skin fold 1040 returns to its original configuration, similar to the adjoining skin, upon subsequent movement of device 1031, while another skin fold is formed. As device 1031 is moved by hand 1036 of a masseur in direction 1044 of the device, similar to natural flow direction 1038, the lymphatic fluids flow in their natural flow direction. However, the lymphatic fluids will not flow if device 1031 were moved in a direction opposite to direction 1044. Wheels 1035 enable constant movement of device 1031.

In some cellulite massage devices, such as those produced by Deka (Italy) or the Lumicell Touch (USA), a low power continuous working infrared light source with a power level of 0.1-2 W/cm$^2$ provides deep heating of the cellulite area and additional stimulation of lymphatic flow. Such a light source is incapable of varying the temperature by more than 2-3° C., since higher temperatures would be injurious to the tissue and cause hyperthermia. Consequently these massage devices are unable to attain the temperatures necessary for achieving selective thermal injury of blood vessels, hair follicles or for the smoothening of fine wrinkles. Due to the movement of the device, the amount of optical energy, e.g. by means of an optical meter, to be applied to the skin cannot be accurately determined.

Figure 5:
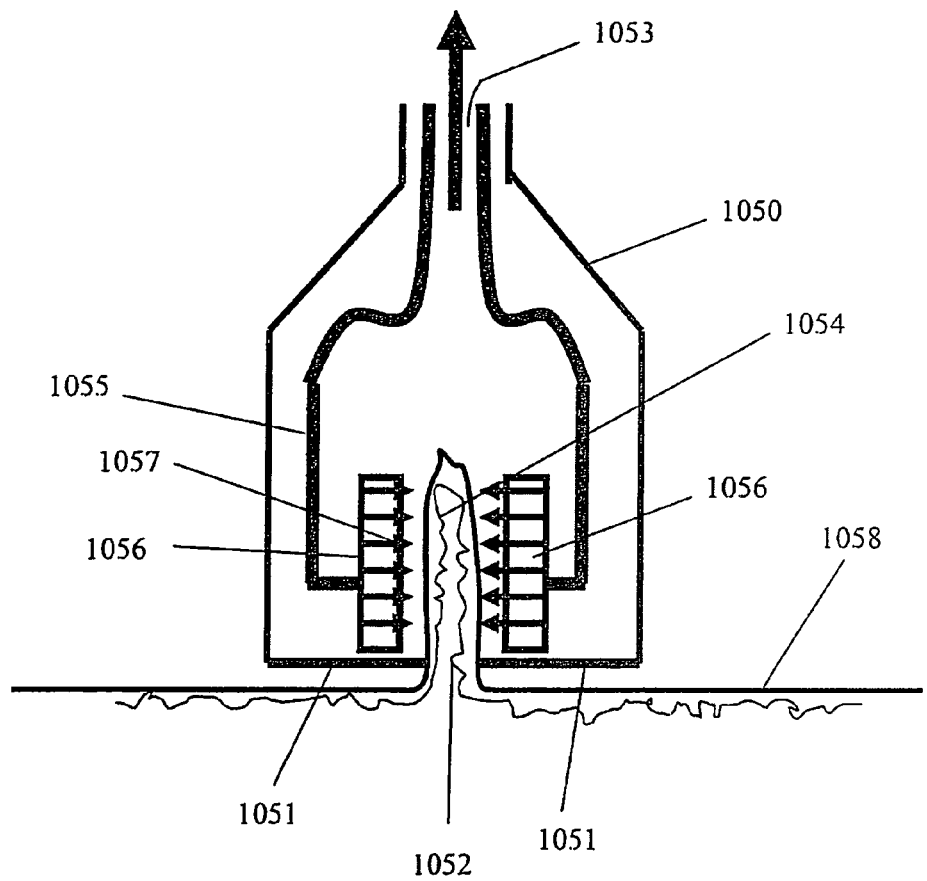
FIG. 5 is a schematic drawing of a prior art vacuum-assisted hair removal device adapted to reduce the blood concentration within a skin fold formed thereby, in order to illuminate two opposed sides of the skin fold and consequently remove melanin-rich hair shafts.

FIG. 5 illustrates a prior art hair removal device, similar to the device of U.S. Pat. No. 5,735,844, which is provided with a slot 1052 within a central region of skin contacting surface 1051 of handpiece 1050. When handpiece 1050 is placed on skin surface 1058 and a vacuum is applied to the handpiece via opening 1053, skin fold 1054 is formed. A narrow slot 1052 induces formation of a correspondingly longer skin fold 1054. Optical radiation is transmitted to the two opposed sides 1056 of skin fold 1054 by a corresponding optical fiber 1055 and optical element 1057. Upon application of the vacuum, skin fold 1054 is squeezed to prevent blood flow therethrough. This device is therefore intended to reduce the concentration of blood within skin fold 1054, in order to increase illumination of melanin-rich hair shafts, in contrast with the apparatus of one embodiment of this invention by which blood concentration is increased within the slight vacuum-induced skin protrusion so as to induce increased light absorption, as will be described hereinafter. Furthermore, this prior art device, due to the reduced concentration of blood within skin fold 1054, is not suitable for treatment of vascular lesions, photorejuvination, or the method of hair removal which is aided by the absorption of optical energy by blood vessels that surround or underly hair follicles (as opposed to the method of hair removal which is aided by the absorption of optical energy by melanin).

Although the application of a vacuum to a skin surface has been employed in the prior art to supplement skin treatments performed by means of optical energy, many significant differences between prior art apparatus for a vacuum-assisted light-based skin treatment to that of the present invention are evident:

a) The prior art application of vacuum is intended to remove smoke or vapors caused by the light-based ablation of a skin surface. By the apparatus of the present invention, in contrast, the optical energy does not interact with the skin surface, but rather is targeted to subcutaneous skin structures without producing smoke or vapors.

b) In order to remove smoke and vapors produced by a prior art light-based skin treatment, a flushing process is required whereby the produced smoke and vapors are purged and replaced by clean air. A low vacuum level is therefore generated, since if a high level vacuum were generated, the treatment handpiece would be prevented from being lifted and displaced from one skin target to another. In contrast, a high vacuum level of approximately 0 atmospheres is generated in the method of the present invention to sufficiently draw the skin into the vacuum chamber and to therefore facilitate the treatment of a skin disorder, yet the treatment handpiece may be quickly repositioned from one skin target to another.

c) Since smoke or vapor removal by means of prior art apparatus prevents the same from adhering to the distal window of a light source, the vacuum application by prior art apparatus should immediately follow each light treatment pulse. The apparatus of one embodiment of the present invention, in contrast, stimulates an increase in blood vessel concentration by applying the vacuum in order to increase light absorption, and therefore the vacuum needs to be applied prior to the firing of the treatment beam.

d) Prior art apparatus does not provide means to temporarily modulate the vacuum level. In contrast, the apparatus of the present invention has control means for modulating the applied vacuum level, by which the optical absorptivity of a skin target may be adjusted in order to effect a desired treatment.

e) Evacuation of skin ablation and of smoke or debris by means of prior art apparatus precludes employment of a protective gel layer over the skin, since the gel forms a barrier between the skin surface and the ambient air. Even if a prior art apparatus were conducive to the application of gel, no provision is made to prevent obstruction of the vacuum pump. In contrast, the apparatus of the present invention allows for the application of gel to the skin prior to a vacuum-assisted non-ablative treatment, since the light-based treatment is subcutaneous, and furthermore, provides means for preventing the obstruction of the vacuum pump.

f) With respect to apparatus of the prior art which is intended to induce blood expulsion from local skin tissue, the treatment beam is limited, to a laser beam of approximately 5 mm. If the treatment beam were significantly larger, e.g. 40 mm, blood expulsion would not be uniform and instantaneous, and therefore blood may remain in the skin tissue after a laser beam has been fired. In contrast, the apparatus of the present invention is suitable for performing skin treatments when the treatment beam is 40 mm, and furthermore is suitable for performing skin treatments by means of an IPL unit having a beam diameter which is significantly larger than that of a laser unit.

g) Prior art vacuum-assisted light-based skin treatment devices are known only to reduce the concentration of blood within a skin target, in order to increase the exposure of the skin target to the treatment light. The apparatus of the present invention, however, employs a vacuum chamber overlying the skin target, as will be described hereinafter, which does not necessarily expel blood from the epidermis of the skin target, but rather increases the blood volume fraction within the skin target.

Figure 22:
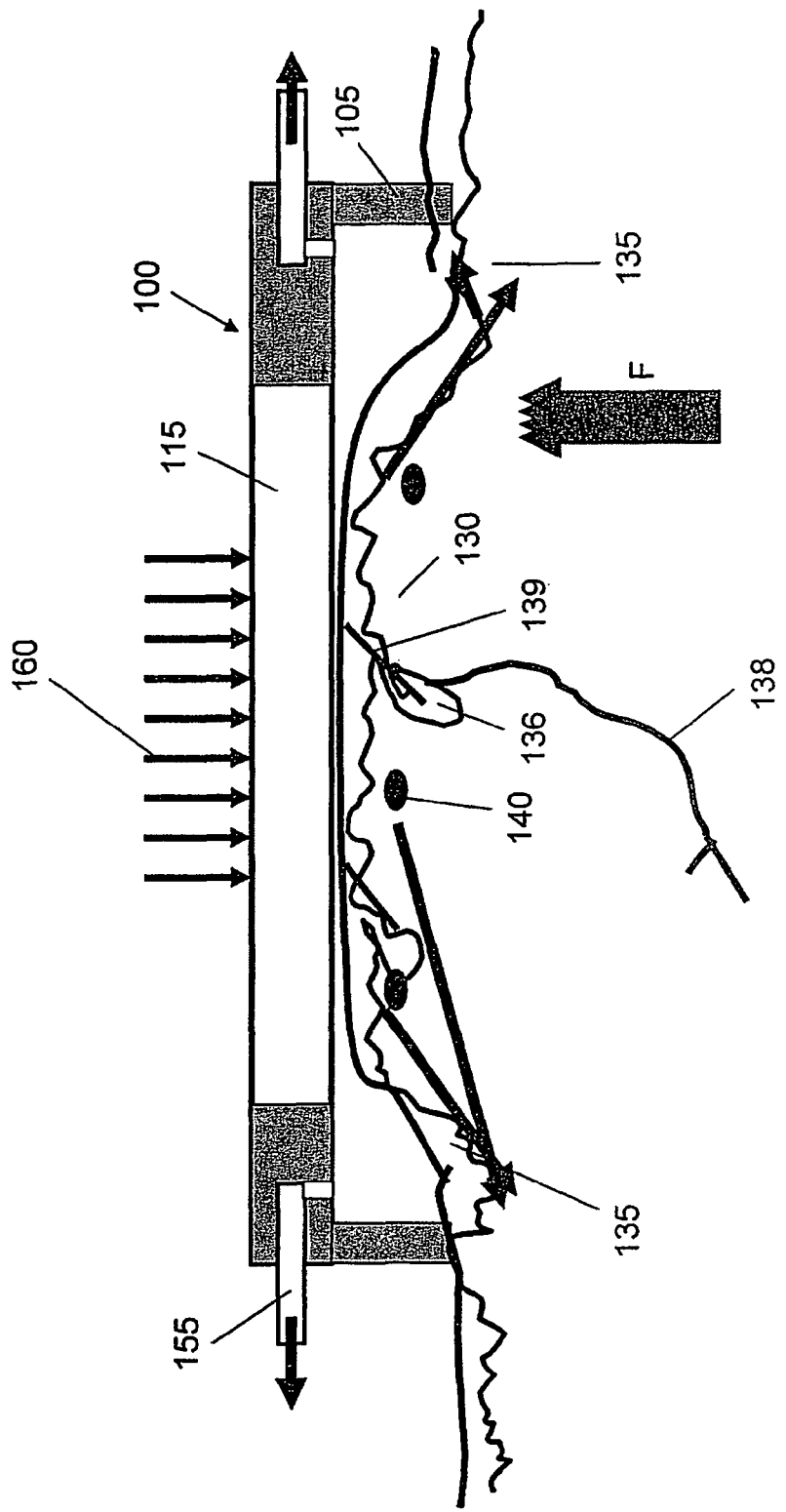
FIG. 22 schematically illustrates a vacuum chamber which is configured to induce the expulsion of blood from a skin target to a peripheral skin area.
Figure 23:
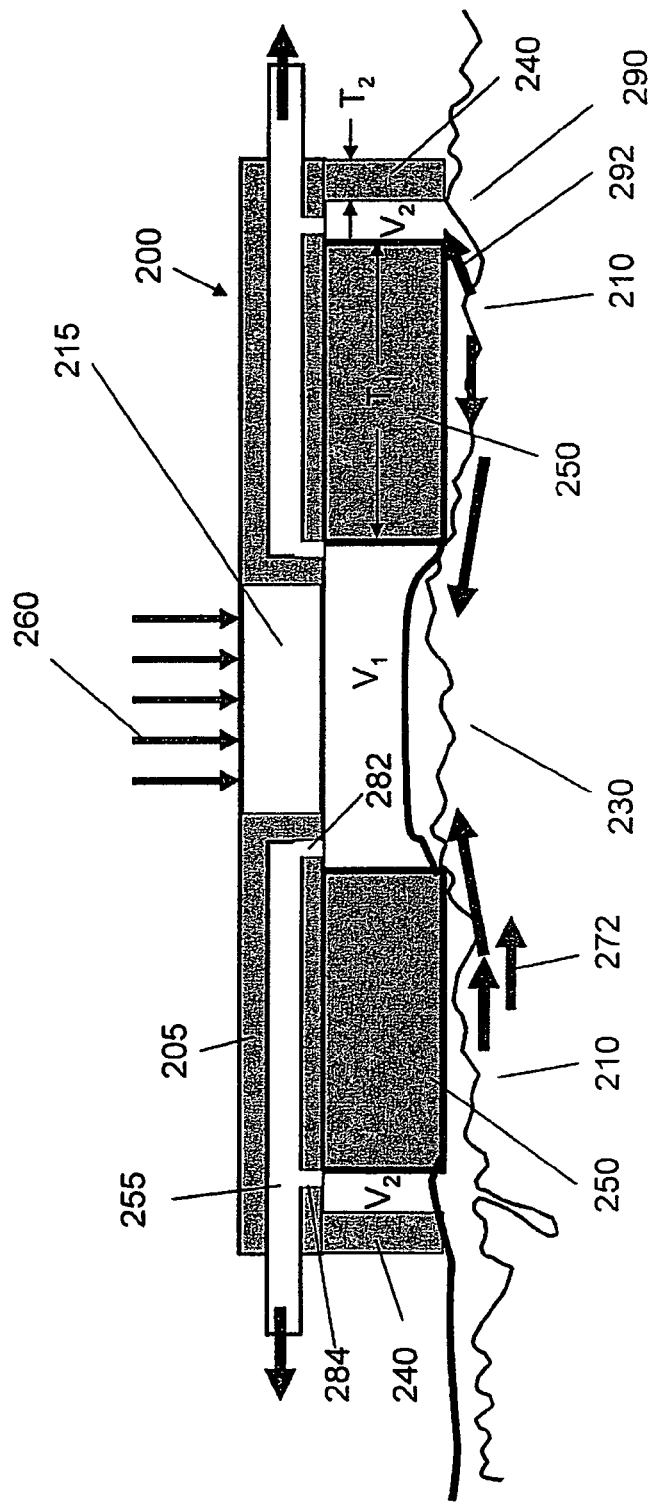
FIG. 23 schematically illustrates a vacuum chamber which is configured to induce blood transfer from a peripheral skin area to a skin target.

FIGS. 22 and 23 illustrate two vacuum chamber configurations, respectively, which induce different blood transfer effects. In FIG. 22, vacuum chamber 100 is configured to induce the expulsion of blood 140 from skin target 130 to peripheral skin area 135, as indicated by the direction of the arrows, while vacuum chamber 200 of FIG. 23 is configured to induce blood transfer from peripheral skin area 210 to skin target 230, as indicated by the direction of the arrows.

The direction of blood transfer is dependent on the ratio of the skin target diameter to the thickness of the vacuum chamber walls. In FIG. 22, vacuum chamber 100 has thin walls 105 which serve to squeeze blood while peripheral skin area 135 slides under walls 105 as skin target 130 is drawn proximally. As walls 105 are thinner or sharper, the localized pressure under the walls is increased, resulting in a more effective squeezing of blood in the same direction as the skin sliding direction and outwardly from walls 105. On the other hand, as shown in FIG. 23, relatively thick support elements 250 of vacuum chamber 200 induce blood transfer towards skin target 230. Due to the increased thickness of support elements 250, the frictional force applied by support elements 250 onto the underlying skin surface is increased relative to that applied by walls 105 of FIG. 22, and therefore peripheral skin area 210 is prevented from sliding under support elements 250. As support elements 250 press on the underlying skin surface, albeit by a localized pressure less than applied by walls 105 of FIG. 22, the corresponding blood vessels are squeezed and blood is forced to flow towards skin target 230.

Apparatus for Controlling Depth of Light Absorption

Figure 6:
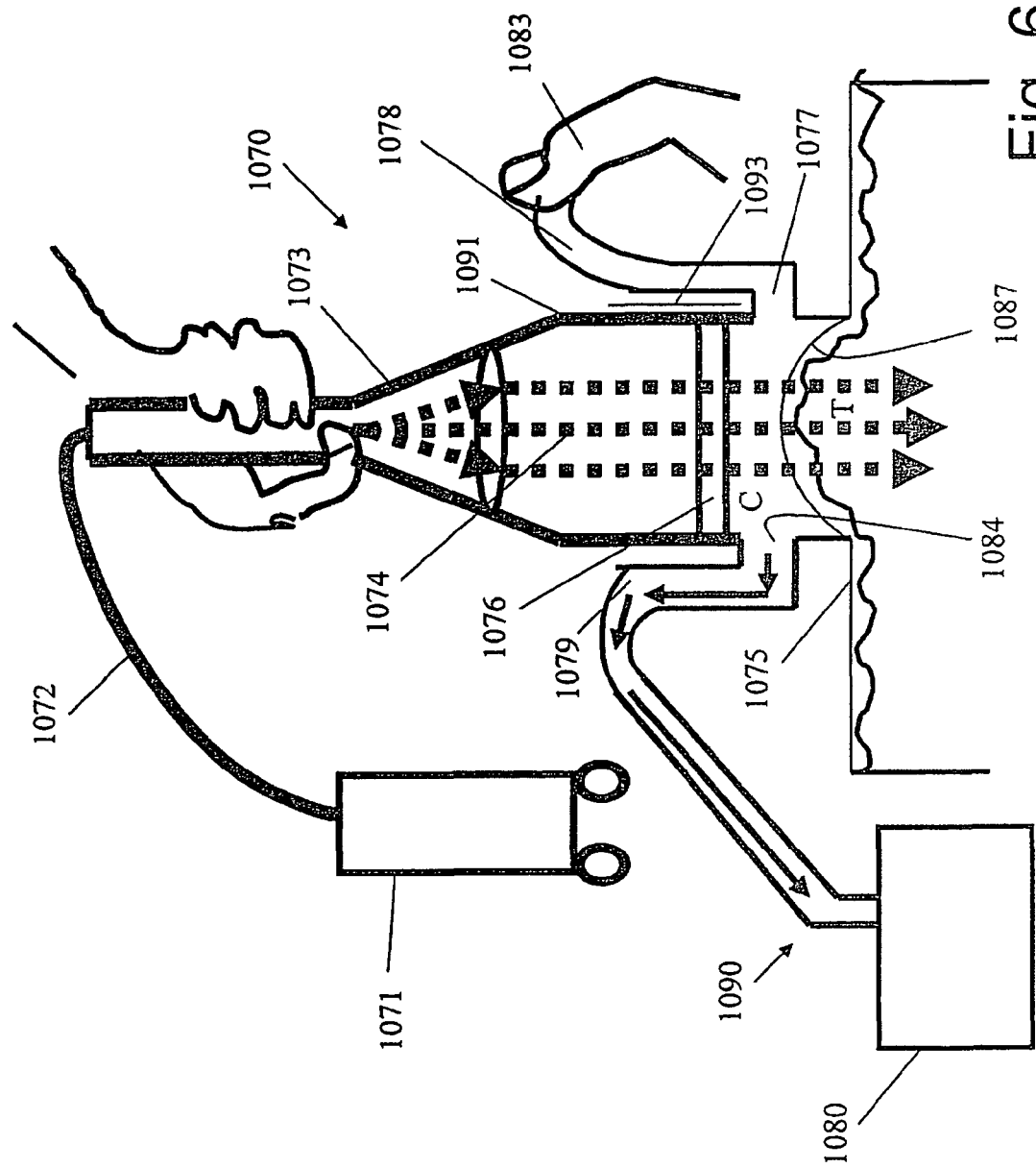
FIG. 6 is a schematic drawing of apparatus in accordance with one embodiment of the present invention, employing a manually occluded U-shaped evacuation chamber.

FIG. 6 illustrates the apparatus according to an embodiment of the invention, which is generally designated by numeral 1070. Apparatus 1070 comprises light source 1071, handpiece 1073 provided with transmitting element 1076 at its distal end, an evacuation unit which is designated by numeral 1090, and preferably a pressure indicator (not shown) for indicating the pressure within the vacuum chamber.

Evacuation unit 1090 comprises vacuum pump 1080, vacuum chamber C, and conduits 1078 and 1079 in communication with chamber C. Vacuum chamber C, which is placed on skin surface 1075, is formed with an aperture (not shown) on its distal end and is provided with a transmitting element 1076 on its proximate end. Vacuum chamber C is integrally formed with handpiece 1073, such that cylindrical wall 1091 is common to both handpiece 1074 and vacuum chamber C. Element 1076 is transparent to beam 1074 of intense pulsed monochromatic or non-coherent light which is directed to skin target T. Element 1076 is positioned such that beam 1074 is transmitted in a direction substantially normal to skin surface 1075 adjoining skin target T. The ratio of the maximum length to maximum width of the aperture, which may be square, rectangular, circular, or any other desired shape, ranges from approximately 1 to 4. Since the aperture is formed with such a ratio, skin target T is proximately drawn, e.g. 1 mm from skin surface 1075, and is slightly deformed, as indicated by numeral 1087, while increasing the concentration of blood in skin target T. Likewise, employment of an aperture with such a ratio precludes formation of a vacuum-induced skin fold, which has been achieved heretofore in the prior art and which would reduce the concentration of blood in skin target T.

Wall 1091 is formed with openings 1077 and 1084 in communication with conduits 1078 and 1079, respectively. The two conduits have a horizontal portion adjacent to the corresponding opening, a vertical portion, and a long discharge portion. Openings 1077 and 1084 are sealed with a corresponding sealing element 1093, to prevent seepage of fluid from the vacuum chamber. Conduit 1079 is also in communication with vacuum pump 1080, which draws fluid, e.g. air, thereto at subatmospheric pressures. U-shaped vacuum chamber C is therefore defined by transmitting element 1076 of the handpiece, slightly deformed skin surface 1087, wall 1091 and conduits 1078 and 1079.

A suitable light source is a pulsed dye laser unit, e.g. produced by Candela or Cynosure, for the treatment of vascular lesions, which emits light having a wavelength of approximately 585 nm, a pulse duration of approximately 0.5 microseconds and an energy density level of 10 J/cm$^2$. Similarly any other suitable high intensity pulsed laser unit, such as a Nd:YAG, pulsed diode, Alexandrite, Ruby or frequency doubled laser, operating in the visible or near infrared region of the spectrum may be employed. Similarly, a laser unit generating trains of pulses, such as the Cynosure Alexandrite laser, the Lumenis "Quatim" IPL or Deka "Silkapill". The emitted light is transmitted via optical fiber 1072 to handpiece 1073. Handpiece 1073 is positioned such that transmitting element 1076 faces skin surface 1087. Beam 1074 propagating towards slightly protruded skin surface 1087 is substantially normal to skin surface 1075.

Following operation of vacuum pump 1080, air begins to become evacuated from vacuum chamber C via conduit 1079. Occluding conduit 1078, such as by placing finger 1083 of an operator on its outer opening increases the level of the vacuum within chamber C to a pressure ranging from 200 to 1000 millibar. The application of such a vacuum slightly draws skin target T towards chamber C without being pressed, as has been practiced heretofore in the prior art, thereby increased the concentration of blood vessels within skin target T. The efficacy of a laser unit in terms of treatment of vascular lesions is generally greater than that of the prior art, due to the larger concentration of blood vessels in skin target T, resulting in greater absorption of the optical energy of beam 1074 within bodily tissue.

The operator may fire the laser following application of the vacuum and the subsequent change in color of skin target T to a reddish hue, which indicates that the skin is rich in blood vessels. The time delay between the application of the vacuum and the firing of the laser is based on clinical experience or on visual inspection of the tissue color.

Figure 7:
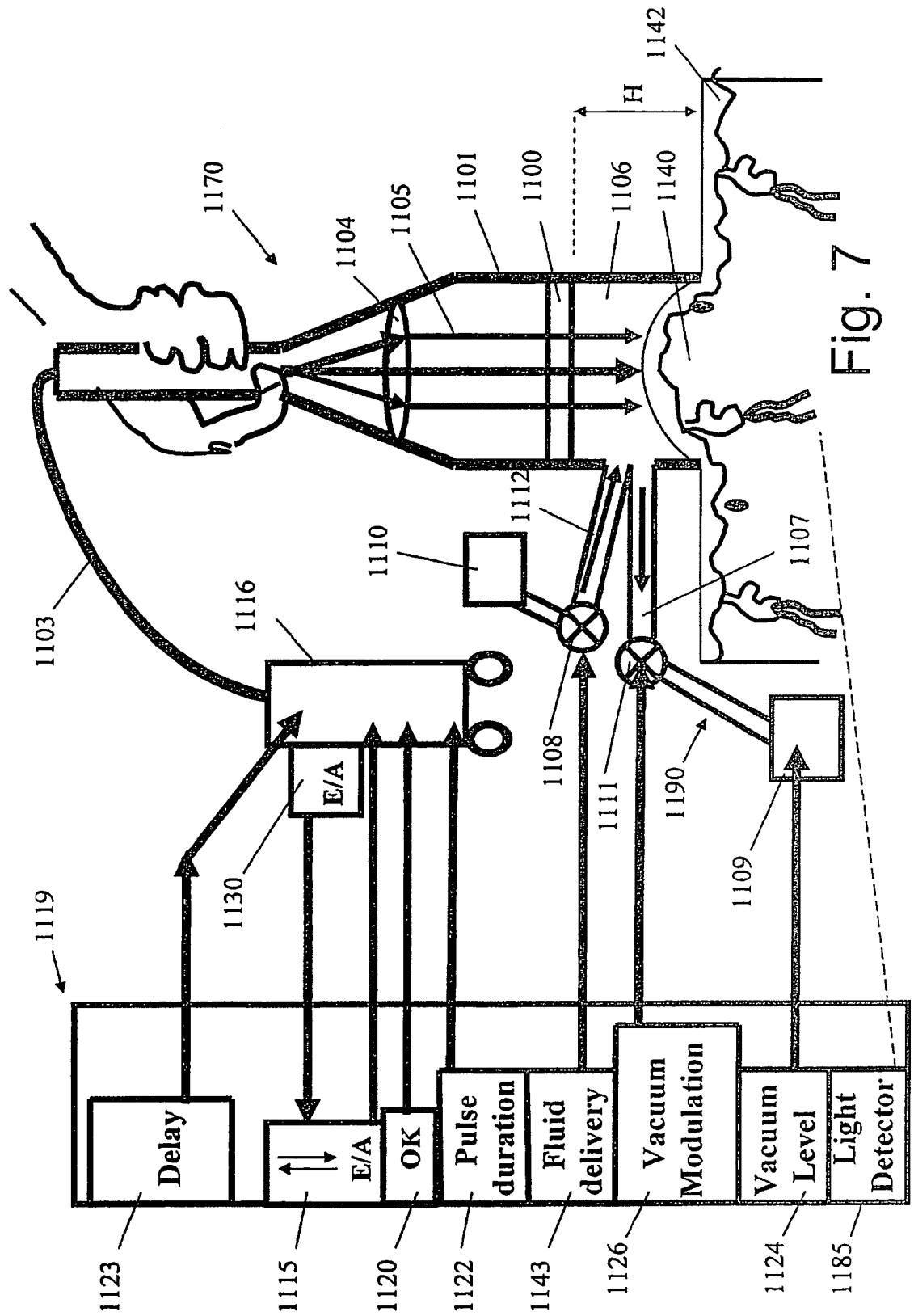
FIG. 7 is a schematic drawing of apparatus in accordance with another embodiment of the present invention, employing an electronically controlled evacuation chamber.

FIG. 7 illustrates another embodiment of the present invention wherein the operation of the vacuum pump and of the pulsed laser or non-coherent light source is electronically controlled. The depth of light penetration within the tissue may be controlled by controlling the time delay between application of the vacuum and the firing of the pulsed light. If the time delay is relatively short, e.g. 10 msec, blood vessel enrichment will occur only close to the surface of the skin at a depth of approximately 0.2 mm, while if the delay is approximately 300 msec, the blood vessel enrichment depth may be as great as 0.5-1.0 mm.

Apparatus 1170 comprises handpiece 1101, laser system 1116, evacuation unit 1190 and control unit 1119.

Laser system 1116 includes a power supply (not shown), a light generation unit (not shown), and power or energy detector 1130 for verifying that the predetermined energy density value is applied to the skin target. Handpiece 1101 held by the hand of the operator is provided with lens 1104, which directs monochromatic beam 1105 transmitted by optical fiber 1103 from laser system 1116 to skin target area 1140. Transmitting element 1100 defining vacuum chamber 1106 is generally in close proximity to skin surface 1142, at a typical separation H of 1-2 mm and ranging from 0.5 to 4 mm, depending on the diameter of the handpiece. The separation is sufficiently large to allow for the generation of a vacuum within chamber 1106, but less than approximately one-half the diameter of the window 1100, in order to limit the protrusion of skin target 1140 from the adjoining skin surface 1142. By limiting the separation of element 1100 from skin surface 1142 while maintaining the vacuum applied to skin target 1140, formation of a skin fold is precluded while more blood may be accumulated in a smaller skin thickness. Therefore a significant local rise in the temperature of a blood vessel, which ranges from 50-70° C., is made possible.

Evacuation unit 1190 comprises vacuum chamber 1106 which is not U-shaped, miniature vacuum pump 1109 suitable for producing a vacuum ranging from 200-1000 millibar, conduit 1107 and control valve 1111 through which subatmospheric fluid is discharged from chamber 1106, and miniature pressurized tank 1110 containing, e.g. 100 ml, which delivers air through conduit 1112 and control valve 1108 to chamber 1106. If so desired, a transmitting element need not be used, and vacuum chamber 1106 defined by lens 1104 will have an accordingly larger volume.

Control unit 1119 comprises the following essential elements:

a) Display 1115 of the energy density level of the monochromatic light emitted by laser system 1116 and a selector for selecting a predetermined energy density.

b) Confirmation indicator 1120 which verifies that the selected energy density is being applied to the skin. Control circuitry deactivates the laser power supply if a beam having an energy density significantly larger than the predetermined value is being fired.

c) Display 1122 concerning the pulse structure, such as wavelength, pulse duration and number of pulses in a train.

d) Control circuitry 1123 for selecting the time delay between operation of vacuum pump 1109 and laser system 1116.

e) Selector 1124 for controlling the vacuum level in vacuum chamber 1106 by means of pump 1109.

f) Control circuitry 1126 for controlling the vacuum duty cycle by regulating the operating cycle of vacuum pump 1109, the open and close time of control valve 1111, the average vacuum pressure, the vacuum modulation frequency, and the repetition rate.

g) Control circuitry 1143 for delivering fluid from positive pressure tank 1110 by controlling the duty cycle of control valve 1108.

h) Light detector 1185 for sensing whether light is impinging onto skin target 1140.

Tank 1110, in which air having a pressure ranging from 1-2 atmospheres is contained, provides a fast delivery of less than 1 msec of air into chamber 1106, as well as a correspondingly fast regulation of the vacuum level therein by first opening control valves 1108 and 1111 and activating vacuum pump 1109. After a sufficient volume of fluid, e.g. 1 ml, is delivered to chamber 1106, control valve 1108 is closed. Control circuitry 1126 and 1143 then regulate the operation of the control valves so to maintain a predetermined level of vacuum. Upon achieving the predetermined vacuum level, control circuitry 1123 fires laser system 1116 after the predetermined time delay, which may range from 1-1000 msec.

Control unit 1119 may also be adapted to increase the pressure in vacuum chamber 1106 to atmospheric pressure (hereinafter in "a vacuum release mode") following deactivation of the pulsed light beam source, to allow for effortless repositioning of the vacuum chamber to another skin target. In order to achieve a fast response time between the deactivation of the light source and the pressure increase within the vacuum chamber prior to repositioning the vacuum chamber to another skin target, light detector 1185 is employed to detect the light emitted by the treatment light source. When the light detector ceases to detect light emitted by the light source, a suitable command is transmitted to control unit 1119, whereupon the latter generates a command to open control valve 1111, in order to increase the vacuum chamber pressure. Alternatively, the vacuum within the vacuum chamber may be released by depressing a pneumatically or electrically actuated button located on the handpiece, following deactivation of the light source. Employment of a light detector which triggers the release of the vacuum in the vacuum chamber in order to allow for the speedy repositioning of the treatment handpiece has particular significance in conjunction with fast treatment systems such as the hair removal "Light Sheer" diode system produced by Lumenis, which operates at a fast rate of 1 pulse per second.

Figure 8:
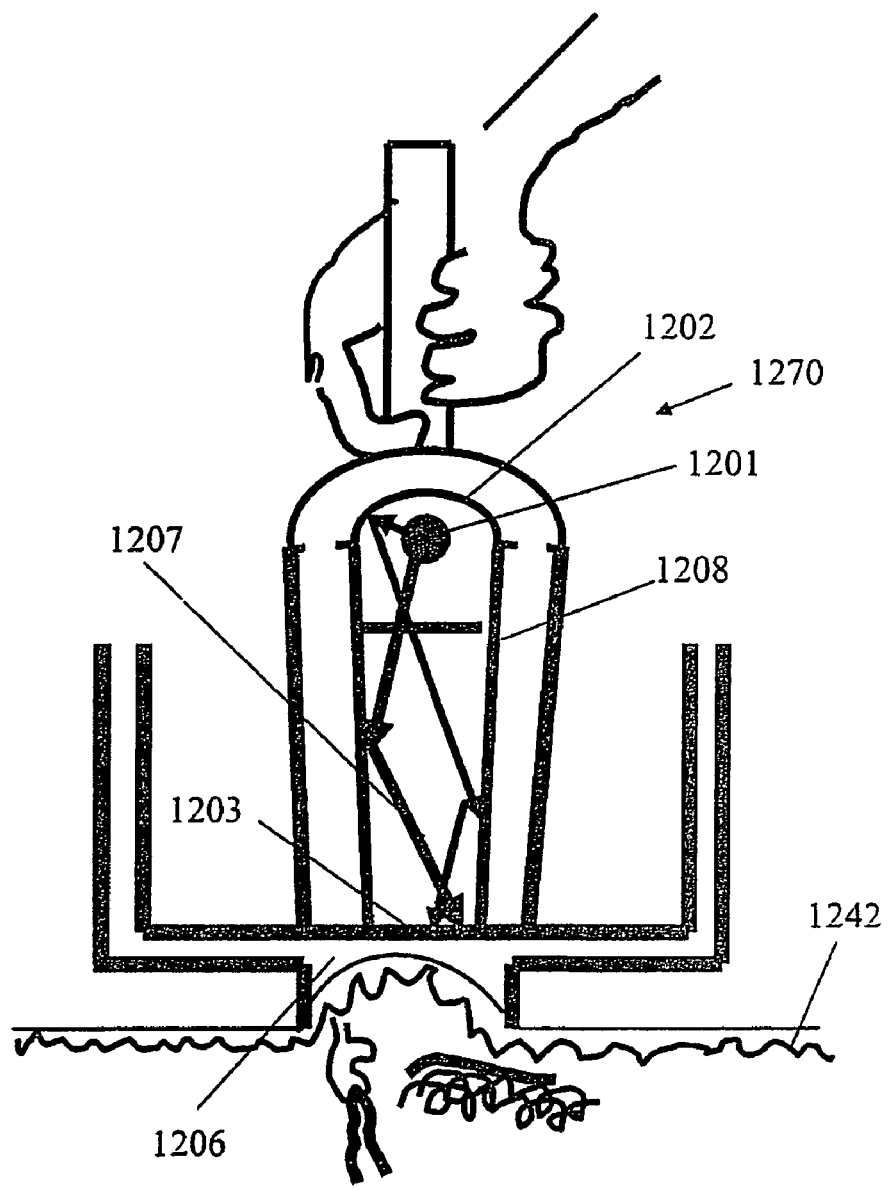
FIG. 8 is a schematic drawing of apparatus in accordance with the present invention, employing an intense pulsed non-coherent light source.

FIG. 8 illustrates apparatus 1270, which comprises a non-coherent intense pulsed light system similar to that described with respect to FIG. 2 and provided with Xe flashlamp 1201, such as one manufactured by Lumenis, Deka, Palomar, or Syneron. Reflector 1202 reflects the emitted light 1207 to light guide 1208. Distal end 1203 of light guide 1208 is separated 1-2 mm from skin surface 1242 to allow for the generation of a vacuum in vacuum chamber 1206 without compromising treatment efficacy by limiting the protrusion of the skin target from the adjoining skin surface 1242.

FIGS. 15a-b illustrate another embodiment of the invention wherein apparatus 1670 comprises a vacuum chamber 1601 which is attached to intense pulsed light guide 1602.

FIG. 15a schematically illustrates vacuum chamber 1601 prior to attachment to the light guide, and FIG. 15b schematically illustrates the attachment of vacuum chamber 1601 to light guide 1602. Vacuum chamber 1601 has walls 1608, side openings 1605 formed in walls 1608, and proximate cover 1612 formed with a proximate aperture 1607 having dimensions substantially equal to the cross section of light guide 1602. Attachment means 1604 facilitates the attachment of vacuum chamber 1601 to light guide 1602 or to any element adapted to protect the light guide. Attachment means 1604 preferably also seals the interface between cover 1612 and light guide 1602, to prevent the infiltration of air into vacuum chamber 1601 after the generation of a vacuum therein. Transmitting element 1625 of light guide 1602 also serves to prevent an increase in vacuum chamber pressure. Once vacuum chamber 1601 is attached to light guide 1602, the vacuum chamber may be placed on a selected skin surface 1603. After a vacuum is generated within chamber 1601, skin target 1606 is drawn into the interior of vacuum chamber 1601, whereupon pulsed light beam 1620 may be fired towards skin target 1606. Vacuum chamber 1601 may be advantageously attached to the distal end of any existing IPL or laser source, to convert the light source into an apparatus for enhancing the absorption of light in targeted skin structures, in accordance with the present invention. This embodiment is particularly useful when the distal end of the light source is provided with an integral skin chilling device.

Figure 9:
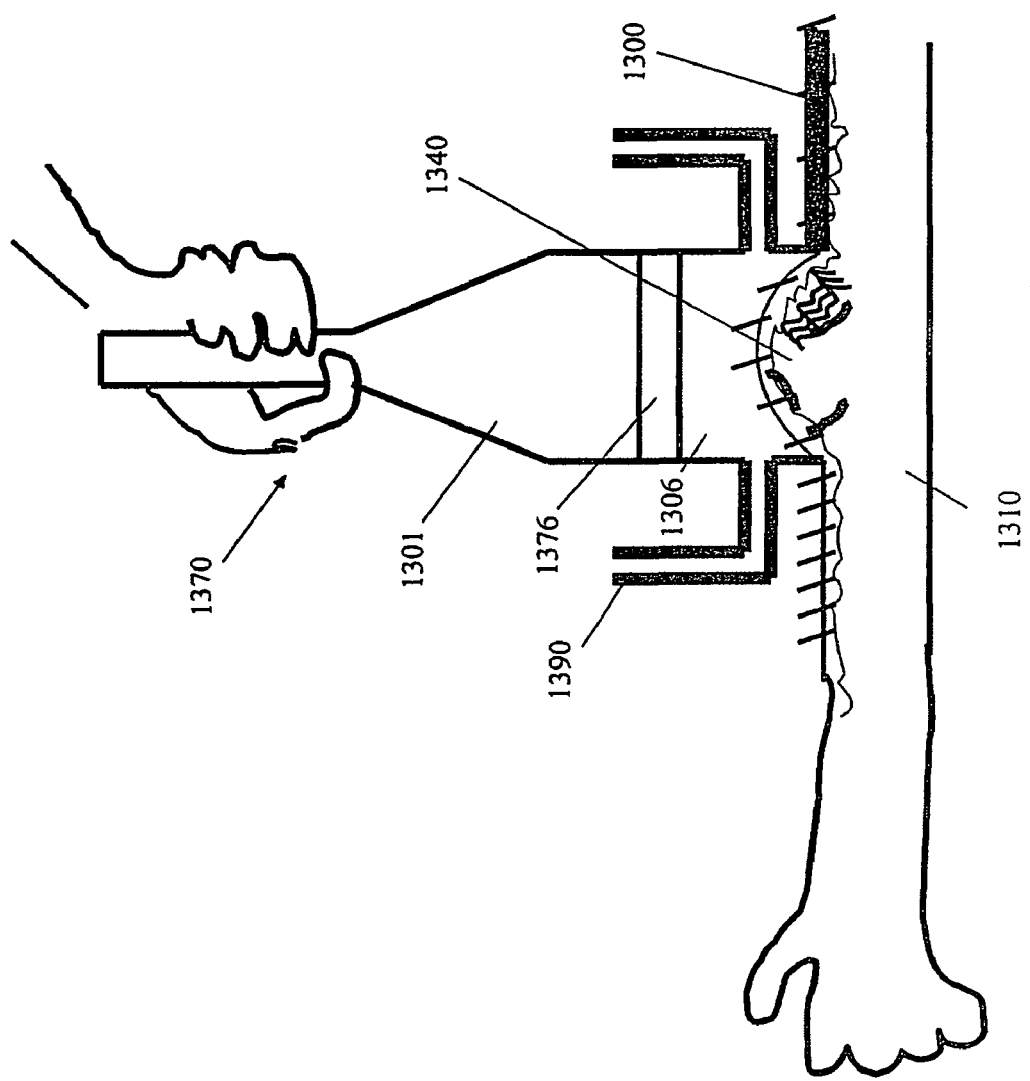
FIG. 9 is a schematic drawing of apparatus in accordance with the present invention, which is provided with a skin chiller.

FIG. 9 illustrates the placement of apparatus 1370 onto arm 1310. Apparatus 1370 comprises handpiece 1301, evacuation unit 1390, and skin chiller 1300 for cooling the epidermis of arm 1310, which is heated as a result of the impingement of monochromatic light thereon. Skin chiller 1300 is preferably a metallic plate made of aluminum, which is in contact with the epidermis and cooled by a thermoelectric cooler. The temperature of the plate is maintained at a controlled temperature, e.g. 0° C. The chilled plate is placed on a skin region adjacent to skin target 1340. The epidermis may be chilled prior to the light treatment by other suitable means, such as by the application of a gel or a low temperature liquid or gas sprayed onto the skin target.

It will be appreciated that the utilization of a U-shaped vacuum chamber 1306 for the evacuation of vapors which condense on transmitting element 1376 is particularly advantageous when a skin chiller in permanent contact with the handpiece outer wall is employed. Such a skin chiller results in condensation of vapors on the transmitting element that would not be evacuated without employment of an evacuation unit in accordance with the present invention. Alternatively, the skin chiller may be releasably attached to the vacuum chamber.

Figure 10:
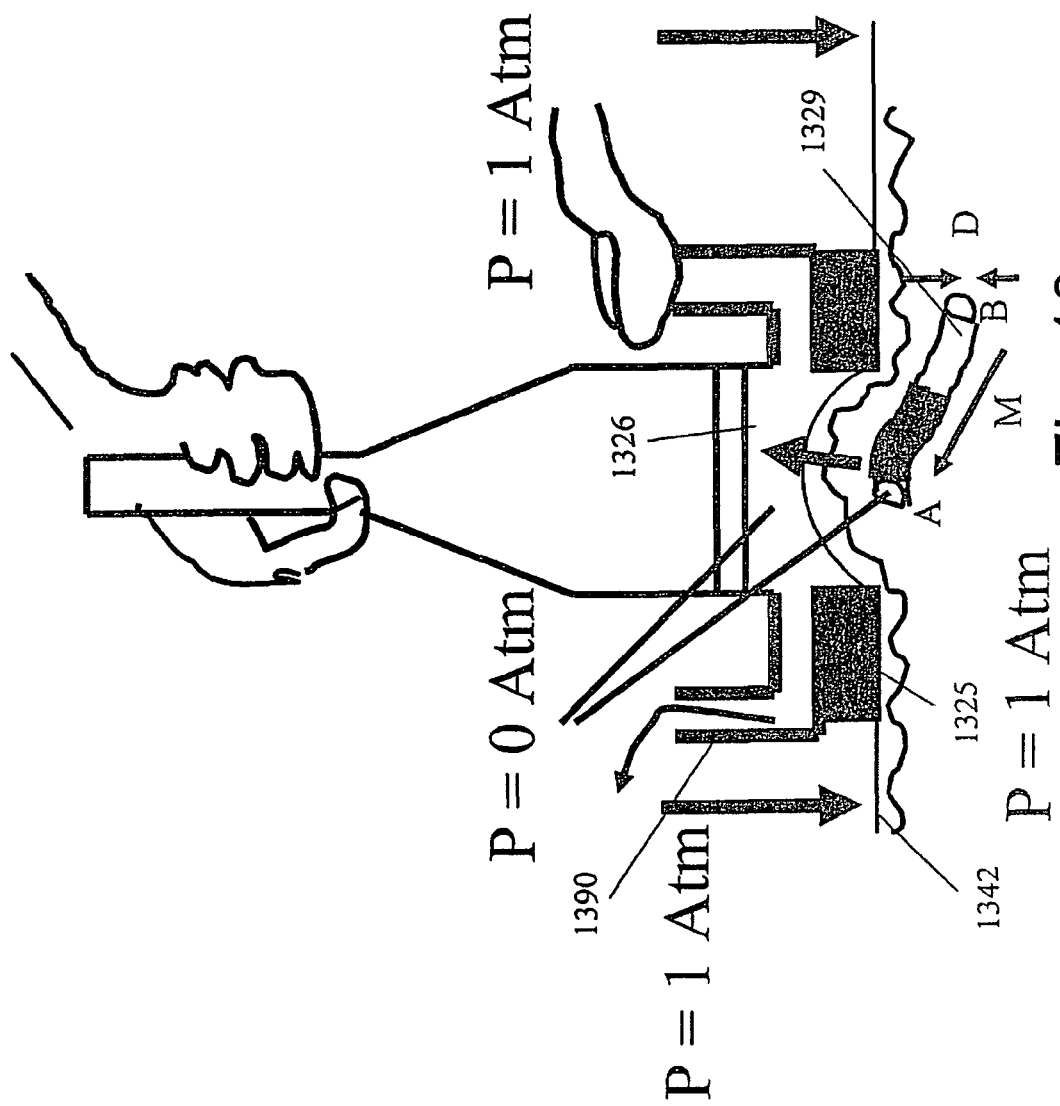
FIG. 10 is a drawing which schematically illustrates the effect of applying a subatmospheric pressure to a vacuum chamber in order to increase the blood concentration in skin drawn towards the vacuum chamber.

FIG. 10 schematically illustrates the effect of applying a subatmospheric pressure to a skin target, in accordance with the present invention, in order to enhance the absorption of light by blood vessels within the skin target. For clarity, the drawing illustrates the effect with respect to a single blood vessel; however, it should be appreciated that many blood vessels contribute to the effect of increased blood transport whereby a plurality of blood vessels are drawn to the epidermis, resulting in increased absorption of the optical energy. The protrusion of the skin target relative to the adjoining skin surface is also shown in disproportionate fashion for illustrative purposes.

The increase in light absorption within blood vessels due to the application of a vacuum in the vicinity of a skin target depends on the vacuum level, or the rate of vacuum modulation, and the skin elasticity which is reduced with increased age. As shown, blood vessel 1329 of diameter D is in an underlying position relative to vacuum chamber 1326. By applying a vacuum by means of evacuation unit 1390, blood flow is established in blood vessel 1329 in the direction of arrow M, due to a difference of pressures between points A and B closer and farther from vacuum chamber 1326, respectively. If the blood vessel is a vein, the flow will be established in only one direction, due to the influence of the corresponding vein valve.

According to the Hagen-Poisseuille equation concerning the flow of viscous fluids in tubes, the discharge from a tube and consequently the duration of flow therethrough depends on a pressure gradient along the tube, the fourth power of the diameter of the tube, and the length thereof. For example, diameters of 100 microns are common for capillaries adjacent to the papillary dermis at a depth of approximately 200 microns and 500-micron blood vessel diameters can be found in the hair bulb at a depth of 3 mm. A typical blood vessel length is approximately 1-2 cm. It will be appreciated that although the blood vessel diameters generally increase with depth, the pressure gradient along the blood vessel is smaller at deeper layers of the skin. As a result, for a given pressure, such as the application of a zero millibar vacuum, each depth from the skin surface corresponds to a characteristic time response for being filled by blood. As a result, modulation of the vacuum by opening and closing control valve 1111 (FIG. 7) controls the flow of blood through blood vessels and consequently controls the degree of light absorption by a blood vessel at a given depth from skin surface 1342. In a realistic situation wherein a plurality of blood vessels are located within a skin target, each skin layer is characterized by a different modulation frequency which typically ranges between 100 Hz for upper layers and 1 Hz for the deep layers under the hair follicles. By opening control valves 1108 and 1111 (FIG. 7) by a varying frequency, the operator may modulate the vacuum applied to the skin target and thereby vary the blood richness of different skin layers.

The operator typically determines an instantaneous modulation frequency of control valves 1108 and 1111 by visually inspecting the skin target and viewing the degree of redness thereat in response to a previous control valve modulation frequency. In addition to improving the treatment efficacy, an increased degree of redness within the skin target advantageously requires a lower energy density of intense pulsed light for achieving blood coagulation or blood heating resulting in the heating of the surrounding collagen. Alternatively, an errythema, i.e. skin redness, meter, e.g. produced by Courage-Hazaka, Germany, may be employed for determining the degree of redness, in order to establish the necessary energy density for the treatment.

For example, a modulation frequency as high as 40 Hz or the firing of a Dye laser unit approximately 1/40 seconds after application of a vacuum may be necessary for applications of port wine stains. In contrast, a delay of approximately a half second for fine wrinkle removal and of approximately 1 second for hair removal may be needed for a depth of 1-3 mm under the skin surface.

Figure 11:
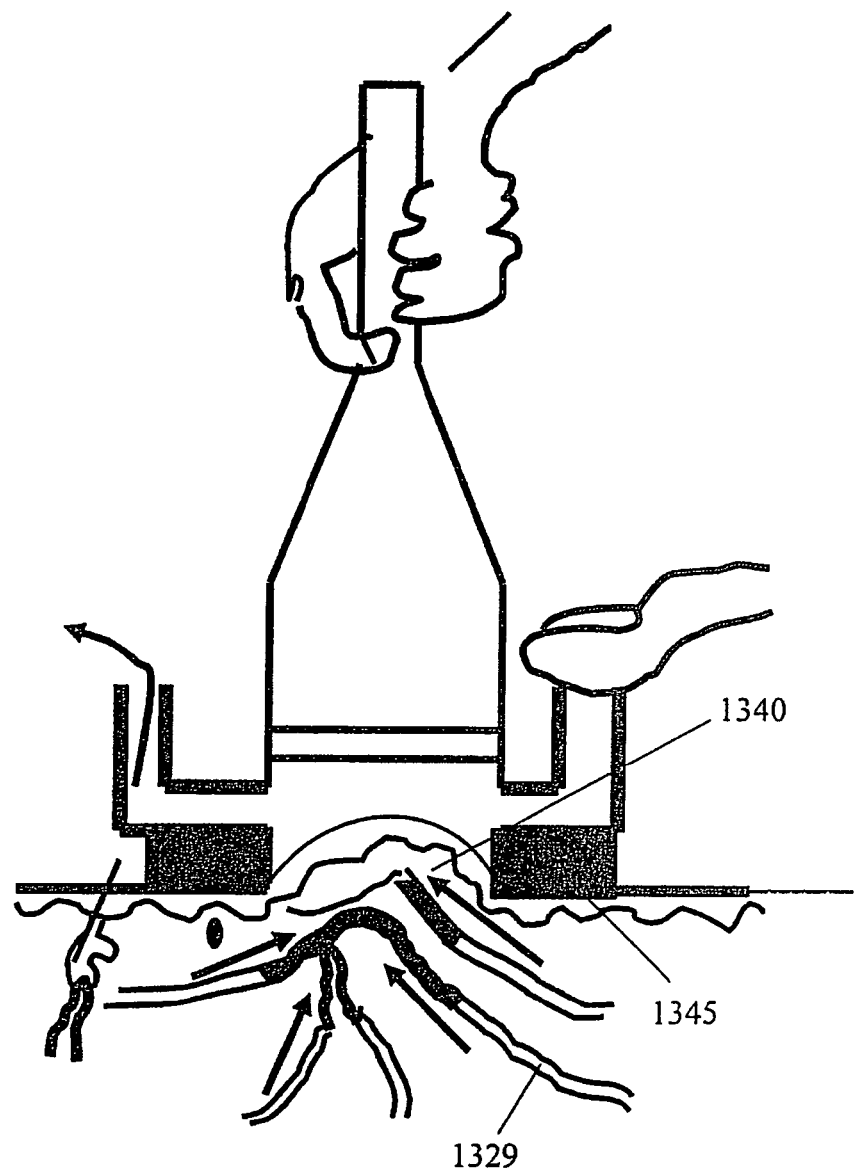
FIG. 11 is a drawing which schematically illustrates the increased concentration of a plurality of blood vessels in a skin target following application of a vacuum to a vacuum chamber, resulting in increased redness of skin and enhanced absorption of light.

FIG. 11 illustrates the concentration of a plurality of blood vessels 1329 in a skin target 1340, which results in the increase of redness of skin and enhanced absorption of light with respect to the hemoglobin absorption spectrum and scattering properties of skin. Light absorption is enhanced by a larger number of blood vessels per unit volume due to the correspondingly larger number of light absorbing chromophores. The beneficial effect of vacuum assisted absorption by Dye lasers or any yellow light, which is strongly absorbed by hemoglobin, is more pronounced on white or yellow skin not rich in blood vessels, such as that of smokers.

Such types of skin suffer from enhanced aging and require photorejuvenation, the efficacy of which is improved with the use of the present invention. Enhanced absorption of light is also advantageously achieved when infrared lasers and intense pulsed light sources are employed.

Figure 12:
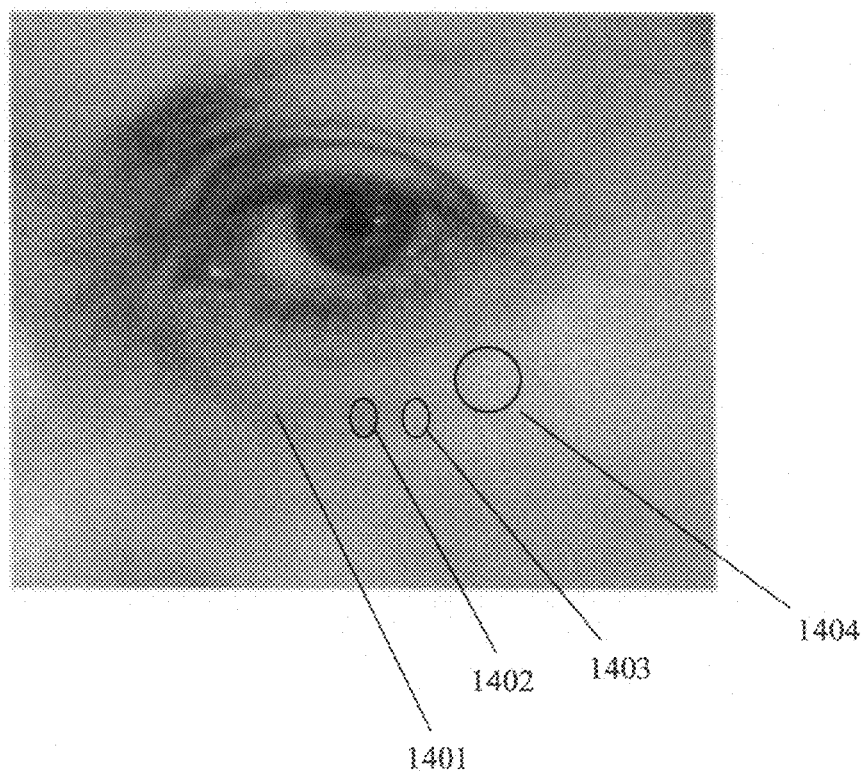
FIG. 12 is an enhanced photograph illustrating the change in skin skin color to a pinker color following the application of a vacuum in accordance with the present invention prior to treatment of a fine wrinkle.

FIG. 12 is an enhanced photograph illustrating the treatment of a fine wrinkle 1401 by means of a vacuum assisted handpiece according to the current invention, which was taken one-half of a second after the application of a vacuum. Circles 1402-4 indicate the sequential change in color of the treatment spots. The color in spot 1403 has become lighter than spot 1402. Spot 1404 has become pinker than spots 1402 and 1403 due to the higher blood fraction.

FIG. 23 illustrates another embodiment of the invention, by which blood vessel concentration within a skin target is increased by selecting the thickness of the supporting elements of the vacuum chamber. Vacuum chamber 200 placed on skin target 230 comprises cover 205, transmitting element 215 centrally retained within cover 205, relatively thin annular leg 240 having a thickness of $T_2$ positioned below cover 205 at the outer periphery thereof, relatively thick annular support element 250 of thickness $T_1$ separated from leg 240 and positioned below cover 205 at skin area 210 adjoining skin target 230, and conduits 255 formed within cover 205 by which the vacuum is applied to the vacuum chamber. Each conduit 255 is provided with an inner inlet 282 and an outer inlet 284. Each inner inlet 282 communicates with volume $V_1$ interior to annular support element 250 and each outer inlet 284 communicates with volume $V_2$, which has a significantly smaller volume than volume $V_1$ and is formed between support element 250 and surrounding annular leg 240.

When a vacuum is applied to vacuum chamber 200, the pressure differential between the surrounding ambient air pressure and the generated vacuum within the vacuum chamber urges vacuum chamber 200 to be in pressing relation with the skin adjoining skin target 230. The resultant force associated with the pressure differential acts on both legs 240 and on support elements 250. Since a vacuum is applied onto the two sides of support element 250 via volumes $V_1$ and $V_2$, the resultant force transmitted to underlying skin area 210 by support element 250 produces a substantially uniform squeezing pressure. By virtue of thin vacuum volume $V_2$, legs 240 serve as a means to stabilize vacuum chamber 200, which is particularly useful on a skin area that is not completely planar, such as in the vicinity of a bone.

The wide area pressure applied by support element 250 onto skin area 210 directs the expelled blood towards skin target 230 as well as towards leg 240. Air evacuated from volume $V_1$ through inner inlets 282 causes skin target 230 to be proximally drawn and blood to be transported from peripheral skin area 210 towards skin target 230. Support element 250 therefore induces inward blood transport from peripheral skin areas 210 to skin target 230, as represented by arrow 272, resulting in a significant increase in the blood volume fraction within skin target 230. After the blood concentration within skin target 230 has sufficiently increased, light beam 260 is suitable for treating vascular lesions with a wavelength well absorbed by the blood vessels within the skin target, and therefore an energy density less than that of the prior art is fired. The depth of light absorption within skin target 230 can be controlled by changing the thickness T of support elements 250.

Air evacuated from volume $V_2$ through a corresponding outer inlet 284 causes skin area 290 underlying corresponding volume $V_2$ to be drawn drawn proximally. Skin area 290 is then pressed by the edge of support element 250 so that blood, as represented by arrow 292, is outwardly transported from support element 250 to leg 240. By inducing outward transport of blood, the blood volume fraction and therefore the depth of light absorption within skin target 230 may be further controlled.

It will be appreciated that the blood concentration within skin target 230 can be increased solely by the pressure applied by support element 250, without use of legs 240. Likewise, support elements 1325, 1345, and 1502 illustrated in FIGS. 10, 11, and 13, respectively, induce blood transport towards the skin target without need of additional legs.

Figure 13:
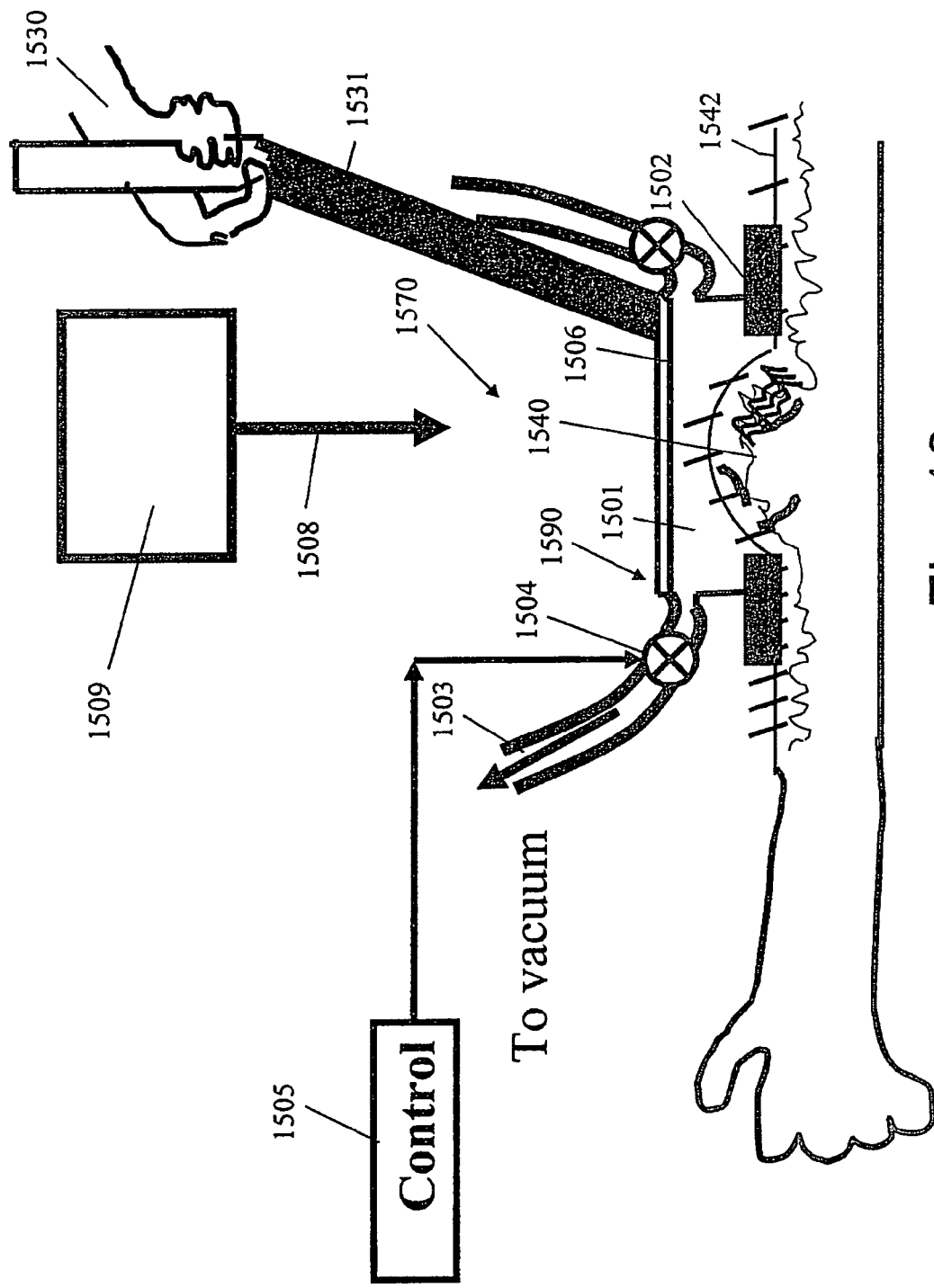
FIG. 13 is a schematic drawing of another embodiment of the invention, illustrating propagation of intense pulsed light from an external light source to a transparent modulated vacuum chamber.

FIG. 13 illustrates apparatus 1570 which increases blood vessel concentration within a skin target without use of a handpiece. Apparatus 1570 comprises evacuation unit 1590 having a transparent vacuum chamber 1501 and a transmitting element 1506, which is made of a thin, transparent polymer such as polycarbonate or of glass, which is transparent to visible or near infrared light. Vacuum chamber 1501 has a diameter of 5-20 mm and a height of approximately 1-3 mm, in order to avoid excessive protrusion of the skin. Chamber 1501 is preferably cylindrical, although other configurations are also suitable. A soft silicon rim (not shown) is adhesively affixed to the periphery of the chamber 1501, in order to provide good contact with skin surface 1542. Conduit 1503 in communication with control valve 1504 allows for the evacuation of vacuum chamber 1501 by means of a miniature vacuum pump (not shown) and control unit 1505. After chamber 1501 is placed on skin target 1540, pulsed beam 1508 from any existing intense pulsed laser or light source 1509 which operate in the visible or near infrared regions of the spectrum may propagate therethrough and effect treatment of a skin disorder. Vacuum chamber 1501 and conduit 1503 are preferably disposable. When vacuum chamber 1501 is disposable, transmitting element 1506 is insertable within a suitable groove formed within the housing of vacuum chamber 1501. Vacuum chamber 1501 may be hand held or may be releasably attachable to the handpiece of light source 1509. When hand held, vacuum chamber 1501, control unit 1505, and a display (not shown) may be integrated into a single device. The treatment may therefore be performed with the use of two hands, one hand, e.g. hand 1530, holding the integrated vacuum chamber device by means of handle 1531 and the other holding the treatment light source. The advantage of this apparatus is its low price and its ability to interact with any intense pulsed laser or non-coherent light source which is already installed in a health clinic.

The absorption of visible intense pulsed light in blood vessels when vacuum is applied to a skin target may be enhanced by the directing electromagnetic waves to the skin target. Radio frequency waves operating in the range of 0.2-10 Mhz are commonly used to coagulate tiny blood vessels. The alternating electrical field generated by a bipolar RF generator, such as produced by Elman, USA or Synron, Canada, follows the path of least electrical resistance, which corresponds to the direction of blood flow within blood vessels. A monopolar RF may also be employed, such as manufactured by Thermage, USA.

FIG. 14 illustrates apparatus 1870 which comprises intense pulsed laser or intense pulsed light source 1821, RF source 1811, and evacuation unit 1890. Evacuation unit 1890 comprises vacuum chamber 1801, which is placed on skin surface 1802 to be treated for vascular lesions, miniature vacuum pump 1805, and control valve 1804 for regulating the level of the vacuum in chamber 1801. Transmitting element 1806 is positioned in such a way that beam 1820 generated by light source 1821 propagates therethrough and impinges skin surface 1802 at an angle which is substantially normal to the skin surface.

RF source 1811 is a bipolar RF generator which generates alternating voltage 1807 applied to skin surface 1802 via wires 1808 and electrodes 1809. Alternatively, the RF source is a monopolar RF generator with a separate ground electrode. Electric field 1810 generally follows the shape of blood vessels 1813, which are the best electrical conductors in the skin. Due to the concentration of blood vessels 1813 in the epidermis, the depth of which below skin surface 1802 depending on the vacuum level and the frequency of vacuum modulation, the combined effect of optical energy in terms of beam 1820 and pulsed RF field 1810 heats or coagulates the blood vessels. Control valve 1804 is regulated by means of control unit 1812. A first command pulse 1 of control unit 1812 controls valve 1804 and a second command pulse 2 controls a delayed radio frequency pulse as well as a delayed light source pulse.

Pain Alleviation

When a vacuum chamber is placed on a skin target, the apparatus provides an additional advantage in terms of the capability of alleviating pain that is normally caused during e.g. the treatment of hair with intense pulsed monochromatic or non-coherent light.

Figure 16:
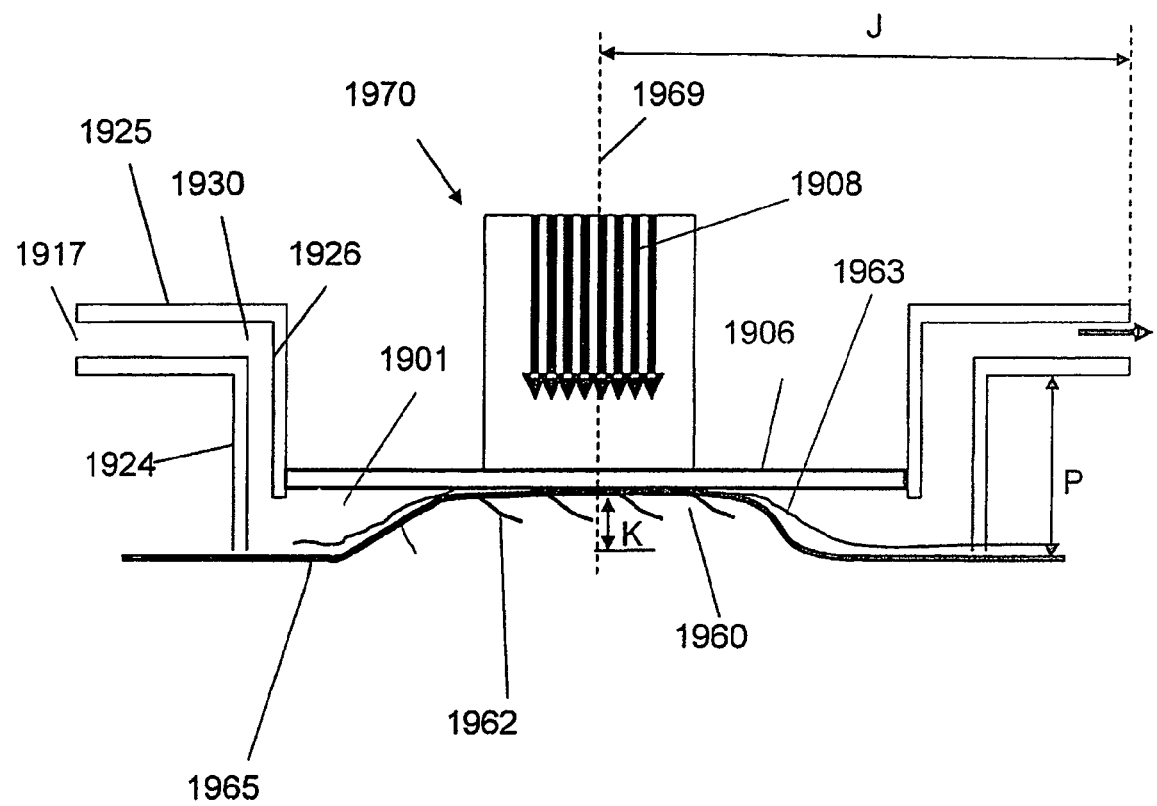
FIG. 16 is a schematic drawing of apparatus in accordance with another embodiment of the invention, which is suitable for alleviating pain during a light-based skin treatment.

As shown in FIG. 16, apparatus 1970 is configured so as to bring skin target 1960, when a vacuum is applied, in contact with transmitting element 1906, e.g. made from sapphire, which is secured to the proximate end of vacuum chamber 1901. The Applicant has surprisingly discovered that the immediate sharp pain which is normally sensed during a light-based skin treatment is alleviated or eliminated when a skin target contacts, and is flattened by, the transmitting element. The level of the applied vacuum is suitable for drawing skin target 1960 towards vacuum chamber 1901 by a slight protrusion of K, e.g. 2-4 mm, with respect to adjoining skin surface 1965, a distance which is slightly greater than the gap between transmitting element 1906 and the distal end of outer wall 1924 of vacuum chamber 1901. During generation of pulsed beam 1908 from any suitable intense pulsed laser or light source propagating through transmitting element 1906, whereby e.g. hair follicles 1962 located under the epidermis of skin target 1960 are treated by the generated optical energy, skin target 1960 is drawn to be in contact with transmitting element 1906. As skin target 1960 is drawn by the vacuum into vacuum chamber 1901 and contacts transmitting element 1906 by means of the resulting proximally directed force, the pain signals generated by the nervous system during the heating of hair follicles 1962, or of any other suitable targeted skin structure, of the patient are inhibited. Accordingly, the synchronization of an optimal delay between the application of the vacuum and firing of the light treatment pulse is a key factor in pain reduction, in order to ensure that skin target 1960 is in contact with transmitting element 1906 for a sufficiently long nerve inhibiting duration when pulsed beam 1908 is fired. Pain reduction is noticeable with use of this apparatus even when the energy level of the light directed to skin target 1960 is increased, an effect which normally causes an increase in immediate sharp pain.

It will be appreciated that the application of a suitable vacuum over a skin surface which causes the latter to be flattened by a flat solid surface is physiologically not equivalent to the application of positive pressure over the skin.

Applying a positive pressure onto a skin surface compresses and squeezes the same. Bones located under the skin surface apply a reactive force and therefore contribute to the degree of skin compression, as well as to the squeezing of blood vessels and of nerves bundles. The physiological reaction to the pressing of skin depends on the skin thickness, and particularly, on the distance of the bones from the skin surface.

In contrast, bones underlying a skin surface drawn by a vacuum applied thereto are not influential during a skin flattening procedure. Since the underlying bones do not apply a reactive force as the connective tissue overlying these bones is drawn towards the vacuum chamber, the physiological processes of connective tissue associated with a vacuum induced skin flattening procedure are different than those of connective tissue which is compressed as a result of the application of positive pressure thereto. The applicants are not aware of any published clinical studies which describe the effects of a vacuum induced skin flattening procedure. Any clinical results of a study regarding the application of positive pressure over a skin surface are not expected to be clinically relevant to those obtainable with respect to a vacuum induced skin flattening procedure.

Pain alleviation was evaluated according to a modified McGill pain questionnaire. The McGill pain questionnaire is well known to pain specialists, and is described by R. Melzack, "The McGill Pain Questionnaire: Major Properties and Scoring Methods," Pain 1 (1975), pp. 277-299. The sensed pain associated with 45 skin targets following a light-based treatment of vacuum-induced flattened skin was compared to the pain associated with light-based treatments conducted without skin flattening. A dramatic pain reduction, from an average of pain level 4, which is indicative of a very painful treatment, to an average of pain level 2, which is indicative of a lack of pain, was revealed.

The applicants have found that an applied vacuum level of at least 150 mmHg, and preferably at least 400 mmHg, is generally needed to alleviate pain. A lower vacuum level, such as of 50 mmHg, which is suitable for blood expulsion, has been found to be not sufficient for the alleviation of pain.

Figure 47:
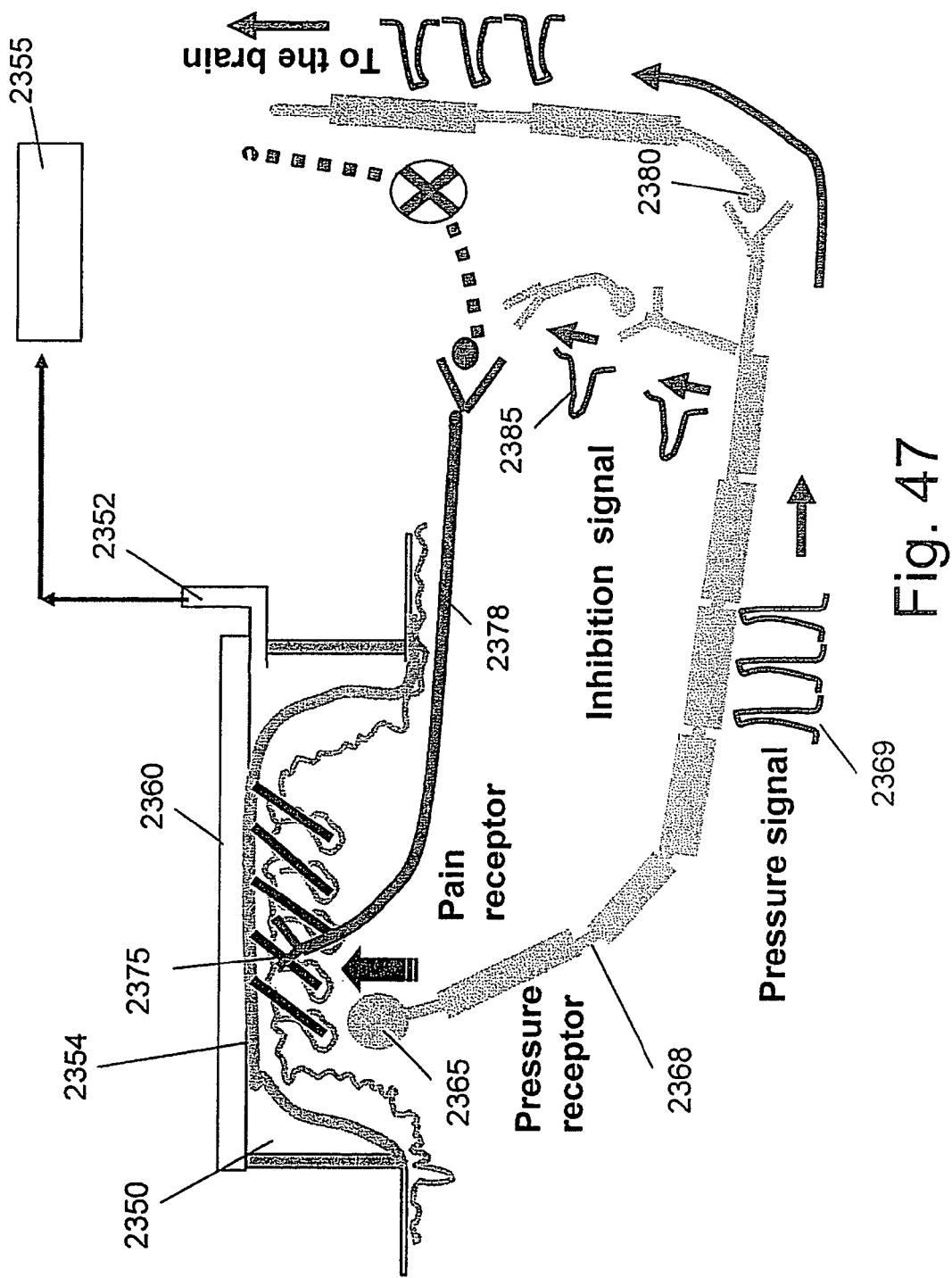
FIG. 47 schematically illustrates a portion of the nervous system that is involved in the generation of a pain inhibiting signal as a skin target is flattened following the application of a suitable vacuum level thereto.

The applicants, have also found that a contributory factor to the level of vacuum-assisted pain reduction is the surface area of the transmitting element. Without wishing to be limited by any particular theory, the inventors believe that the relationship between the level of vacuum-assisted pain reduction and the surface area of the transmitting element is reflected in FIG. 47. As schematically illustrated, a transmitting element 2360 of a sufficiently large area ensures that a correspondingly large number of pressure receptors 2365 will be compressed. During operation of vacuum pump 2355, which is adapted to evacuate air from vacuum chamber 2350 via conduit 2352, skin target 2354 is drawn towards, and flattened by, transmitting element 2360. Pressure receptors 2365 sense the compression of skin target 2354 as it is flattened by transmitting element 2360, and fast conducting myelinated pressure nerve 2368 located within skin target 2354 transmits a generated pressure signal 2369 to the spinal cord. Pressure signal 2369 functions as an inhibition signal 2385 within the spinal cord at a synaptic connection 2380 to the brain, thereby inhibiting the pain signal, which is normally transmitted to the brain via the spinal cord through slower non-myelinated pain nerve 2378 after being sensed by pain receptor 2375 as a result of the relatively high increase in temperature during a skin treatment performed by means of electromagnetic energy such as laser or IPL light, from being transmitted to the brain. If the area of transmitting element 2360 is not sufficiently large, fewer pressure receptors 2365 will be compressed and a pain sensation will be felt due to the transmission of the corresponding pain signal to the brain from pain nerves which are not gated by pressure receptors. Pain reduction has been found to be noticeable when the transmitting element has an area of at least 100 mm², such as one that has a length of 20 mm and a width of 40 mm.

The applicants have also surprisingly found that the pain signals cease to be inhibited when the duration of the applied vacuum is longer than a predetermined value. When the duration of the applied vacuum is longer than a value ranging from approximately 0.1-6 seconds, the compression of the drawn skin against the transmitting element does not provide a pain inhibiting effect. An upper limit of the vacuum applying duration is a significant parameter, and prior art vacuum-assisted skin treatment devices are not capable of effectively inhibiting pain transmission, particularly due to the lack of control means for automatically releasing the applied vacuum within the aforementioned duration range. A skin treatment performed with the use of electromagnetic energy is liable to very painful if a pain inhibition signal is not generated during the treatment, i.e. the vacuum chamber, if one exists, is not suitable for drawing skin in compressing fashion against a transmitting element, or the vacuum applying duration is longer than approximately 6 seconds and the delay between the generation of the vacuum and that of the treatment energy directed to the skin target is significantly greater than 6 seconds.

Vacuum chamber 100 illustrated in FIG. 22 is also configured to alleviate the pain resulting from the firing of light beam 160 onto skin target 130. When a vacuum is applied onto vacuum chamber 100 via conduits 155, skin target 130 is drawn and contacts transmitting element 115. Instead of sensing immediate sharp pain during impingement of each treatment pulse with a skin area 136 of skin target 130, the magnitude of proximally directed force F resulting from the applied vacuum causes nerve 138 surrounding a corresponding hair bulb and extending to skin area 136 to be pressed onto transmitting element 115 for a sufficient duration to inhibit the pain sensation. Light beam 160 is of a wavelength which is well absorbed by hair follicles 139. By optimizing the time delay between application of the vacuum and the firing of light beam 160, the pain sensation is sufficiently inhibited and the energy density of light beam 160 need not be decreased.

The apparatus for alleviating pain during vacuum-assisted light-based treatments of the skin may include a control device (not shown) for adjusting the vacuum level generated by the vacuum pump, as well as the time delay between the application of the vacuum and the firing of light beam. The control device preferably has a plurality of finger depressable buttons, each of which is adapted to set the vacuum pump and light source at a unique combination of operating conditions so as to generate a predetermined vacuum level within vacuum chamber 100 and to result in a predetermined time delay between the operation of the vacuum pump and the firing of light beam 160, and a display to indicate which button was depressed. The apparatus may also comprise control valves in electrical communication with the control device for evacuating air into vacuum chamber during a vacuum applying mode and for introducing air therein during a vacuum release mode, respectively. The health professional is aware of the anticipated pain level that a patient generally senses when one of these buttons is depressed. If the pain threshold of a patient is relatively low or if the application of the vacuum by the vacuum chamber onto the skin target is annoying, the health professional may change the combination of operating conditions by depressing a different button. Alternatively, the pain threshold of a patient may be objectively determined by an electrical measurement of a muscle reflex in response to pain.

As skin target 130 is pressed onto transmitting element 115 during the application of the vacuum, blood is displaced from skin target 130 to peripheral skin area 135. Although the blood fraction volume in peripheral skin area 135 is increased, the latter is nevertheless liable to be damaged by the treatment light, which may diffuse subcutaneously from skin target 130 to skin area 135. To counteract the potential thermal injury to skin area 135, heat absorbing gel (not shown in the figure) is applied to skin target 130 prior to application of the vacuum and is subsequently squeezed to peripheral skin area 135 by means of transmitting element 115. The displaced gel therefore advantageously protects peripheral skin area 135 from being injured by subcutaneously diffused treatment light.

Figure 43:
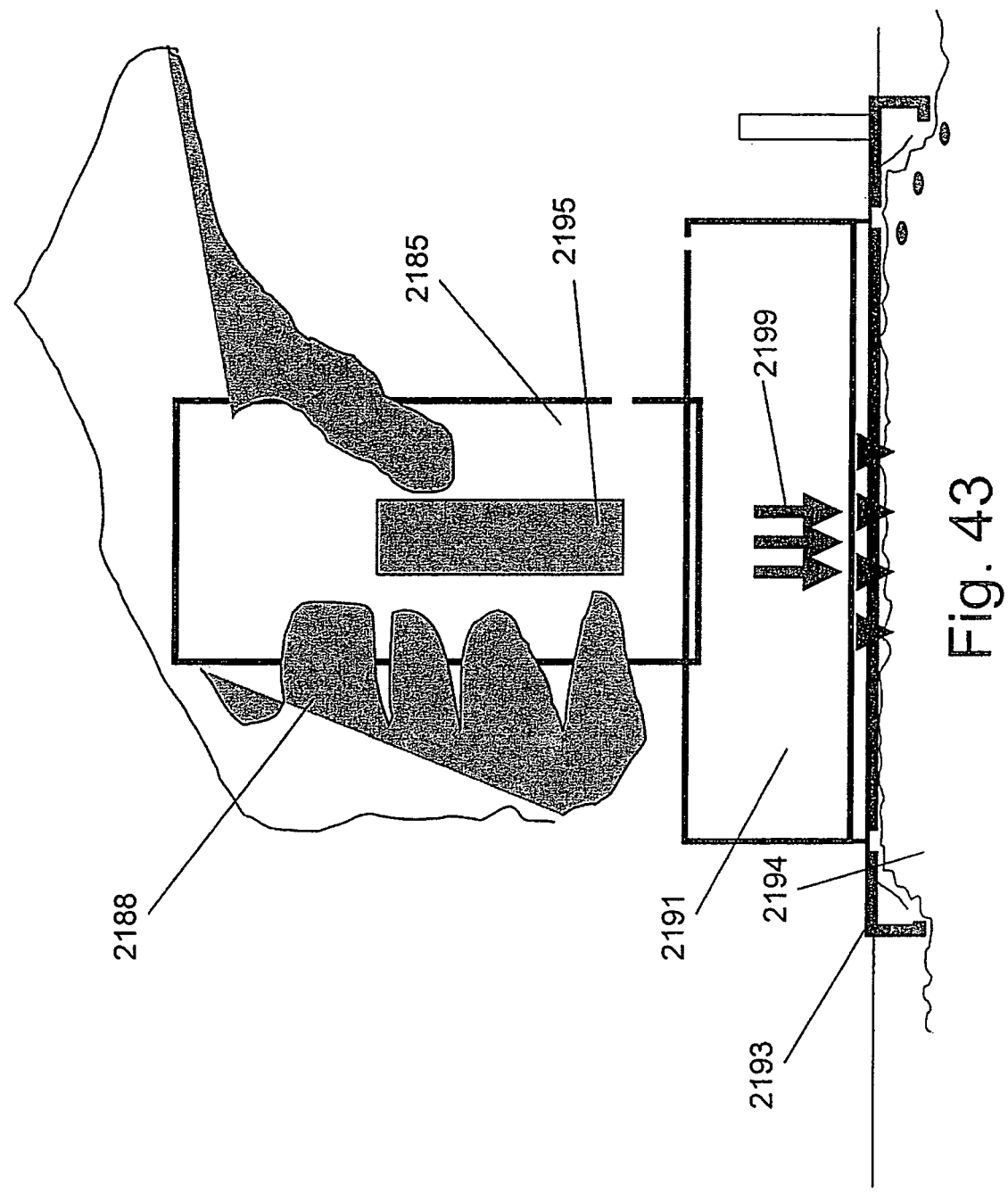
FIG. 43 schematically illustrates a treatment handpiece held by one hand which comprises a light source and a vacuum chamber.

FIG. 43 illustrates a treatment handpiece 2185 which comprises a light source 2195 and is held by a hand 2188. The treatment light 2199 propagates through transmitting element 2191 and pain inhibiting vacuum chamber 2193, which draws and flattens skin 2194 in order to inhibit the transmission of pain.

Figure 28:
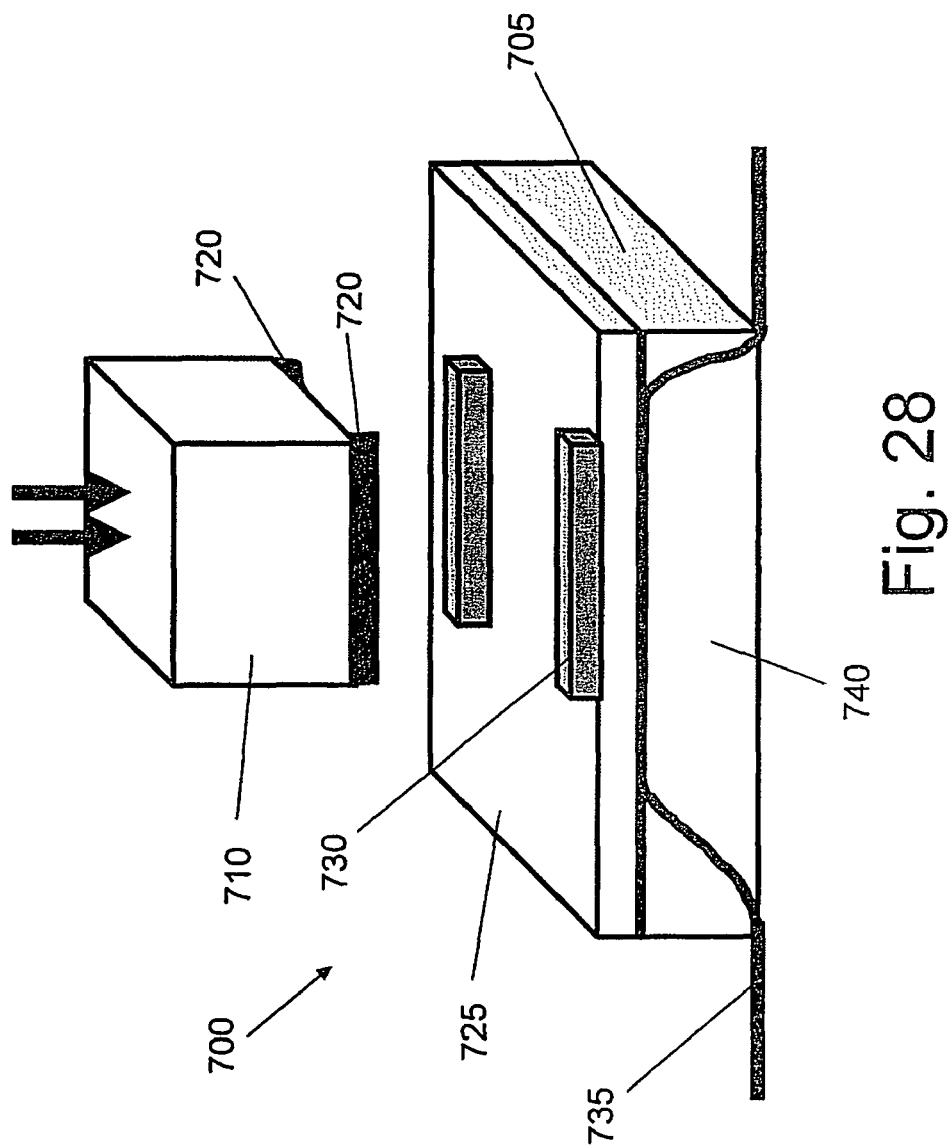
FIG. 28 is a schematic perspective view of a sapphire transmitting element that is suitable for transmitting both light and RF waves to a skin target.

FIG. 28 illustrates another embodiment of the invention which is suitable for pain alleviation. Apparatus 700 comprises vacuum chamber 705 and IPL treatment light source 710, e.g. one produced by Syneron USA, which is provided with an RF source at the distal end thereof in the form of two electrodes 720. When transmitting element 725 of vacuum chamber 705 is made of sapphire, which has electrical insulating properties, the RF waves are prevented from propagating to skin target 735. To allow sapphire to be a suitable transmitting element for apparatus 700, two metallic conducting electrodes 730 are welded in two slits, respectively, formed in the sapphire transmitting element 725. The slits in sapphire transmitting element 725 may be formed by ultrasonic drilling or by precision abrasive drilling, such as with bits produced by American Precision Dicing Inc, USA, Rotem, Israel, or KPE, Israel. Exemplary dimensions of the electrodes are a width of 2 mm, a length of 17 mm long, and a depth of 2 mm deep, so as to be compatible with a diode laser such as produced by Syneron so that the electrodes of the diode laser may be placed on electrodes 730 of the sapphire transmitting element. Electrodes 730 are positioned to be within the propagation path of electrodes 720 integrally formed in light source 710. Suitable means, such as a magnetic rod (not shown), may be used to ensure the quick centering of light source 710 with respect to electrodes 730 of sapphire transmitting element 725. During application of the vacuum, skin target 740 contacts the sapphire transmitting element 725 and electrodes 730 transmit RF waves to skin target 740.

Figure 29:
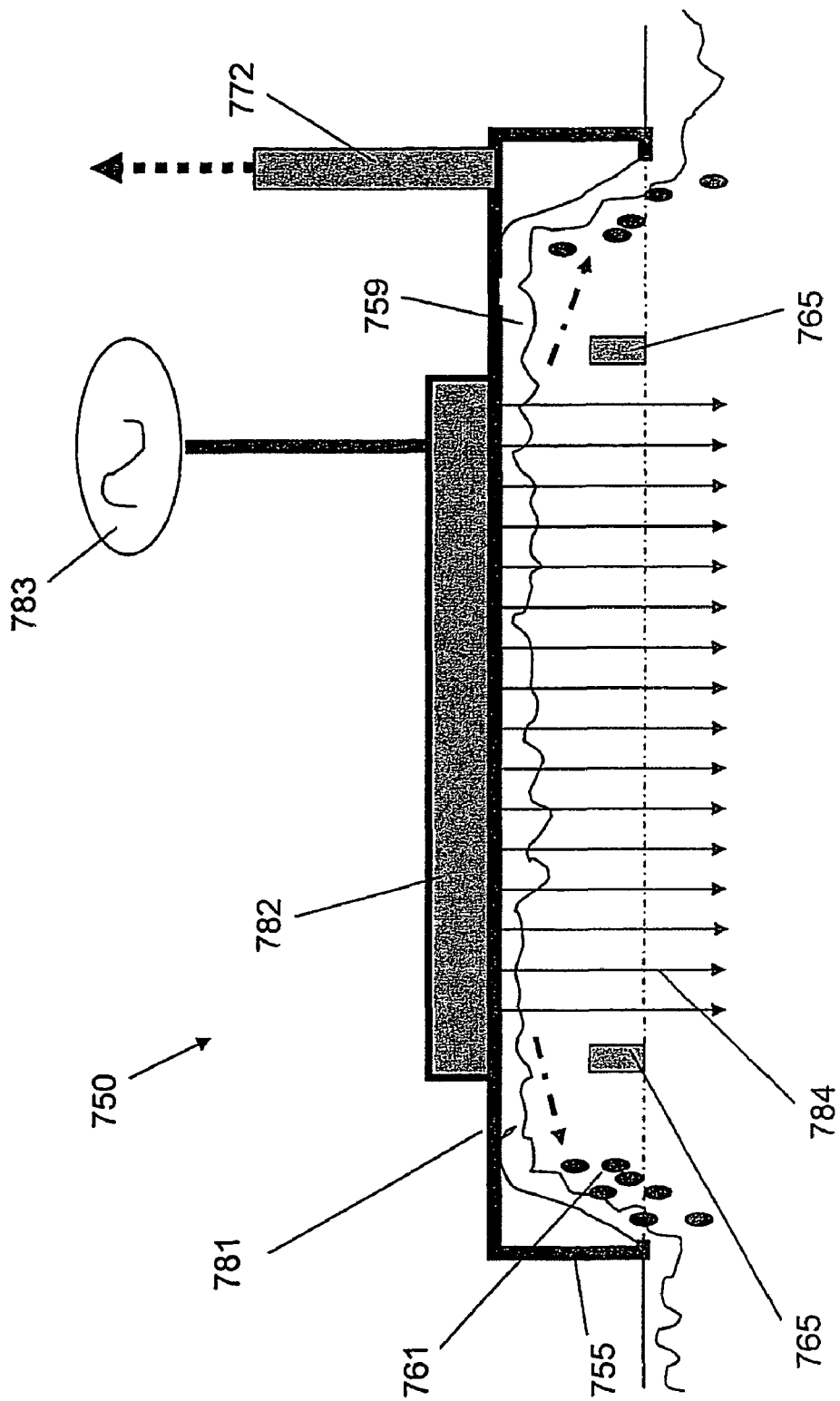
FIG. 29 schematically illustrates a large sized vacuum chamber used for pain alleviation in conjunction with a monopolar RF source.
Figure 30:
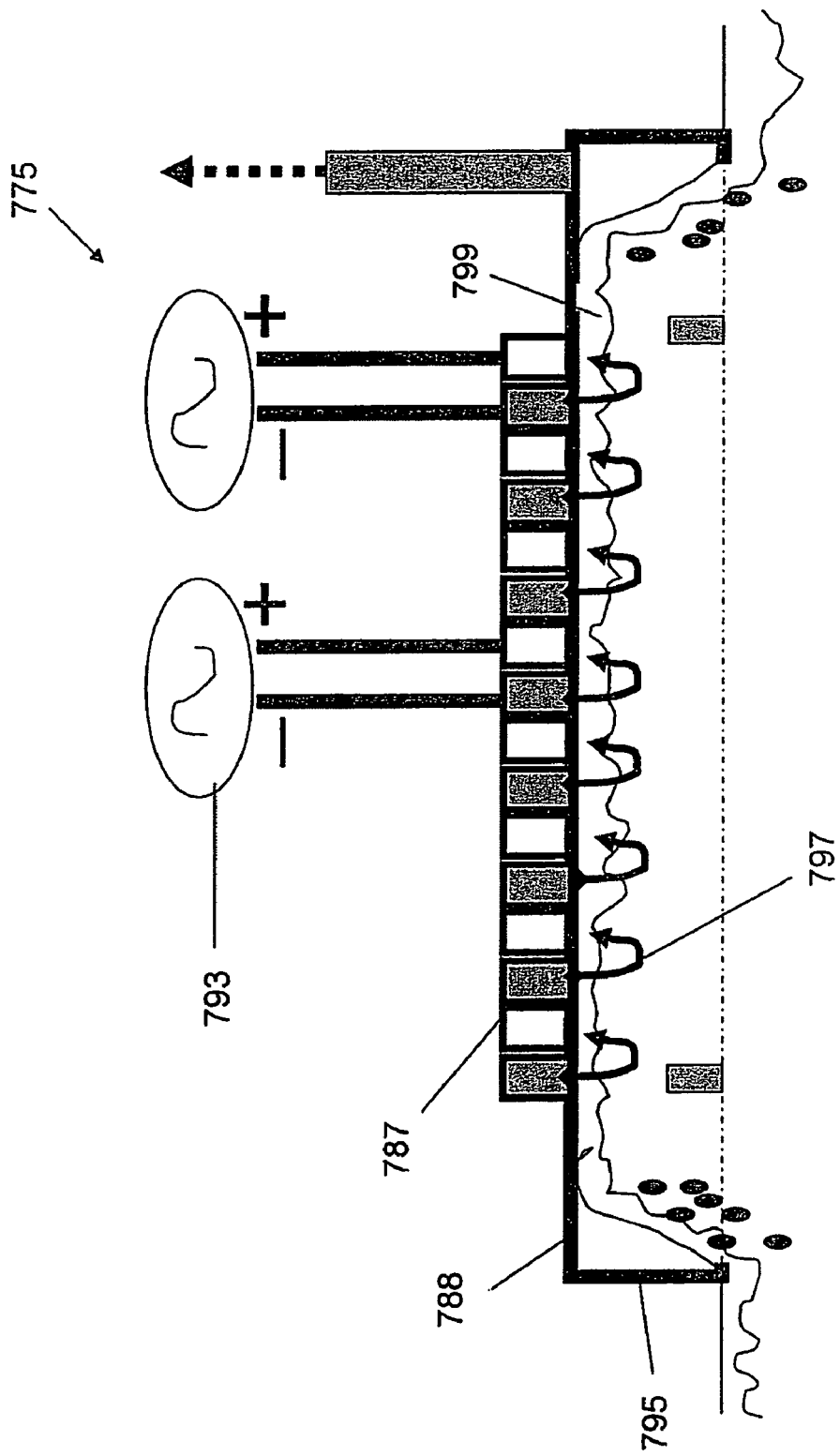
FIG. 30 schematically illustrates a large sized vacuum chamber used for pain alleviation in conjunction with a bipolar RF source.

FIGS. 29 and 30 illustrate another embodiment of the invention wherein a large sized vacuum chamber is used for pain alleviation in conjunction with a RF-based skin treatment. The apparatus of FIG. 29 employs a monopolar RF source, while the apparatus of FIG. 30 employs a bipolar RF source. Each of these RF sources is used for different types of treatment. A monopolar RF source is generally employed when deep skin tightening is needed, such as for skin of the abdomen or legs with cellulite. A bipolar RF source is generally employed for more superficial skin tightening such as with respect to facial treatments. If so desired, the RF-based skin treatment may be supplemented by a light-based treatment.

As shown in FIG. 29, apparatus 750 comprises RF source 783, vacuum chamber 755, vacuum chamber cover 781, and transmitting element 782 positioned within vacuum chamber cover 781. Air is evacuated through duct 772 during the generation of a vacuum within chamber 755. Markers 765 located on a side of vacuum chamber 755 and separated by a distance substantially equal to the length of transmitting element 782 assist in the relocation of the vacuum chamber to a desired position while displacing the handpiece containing the vacuum chamber from one skin target to another. By being sufficiently conspicuous, markers 765 provide a visual association with the location of the previous skin target.

Transmitting element 782, which is capable of being in contact with drawn skin 759, may be made from a transparent material coated with a transparent conductive coating, such as produced by Edmund Optics Inc., USA, Melles Griot Inc., USA, or Ophir Optics, Inc., USA, or may be a metallic element. Transmitting element 782 is able to conduct monopolar field 784 generated by RF source 783 through drawn skin 759. Monopolar field 784, which may be generated at an energy density ranging from 1 J/cm$^2$ to 50 J/Cm$^2$ and a frequency ranging from 0.4 MHz to 1 GHz, is perpendicular to the surface of drawn skin 759 and terminates at a return electrode placed on a bodily portion such as the back, as well known to those skilled in the art. For example, monopolar field 784 may be generated at an energy density of 2.4 J/cm$^2$ and a frequency of 2.4 MHz.

Vacuum chamber 755 is configured to induce blood expulsion from the skin target when a vacuum is applied within vacuum chamber 755 above the the skin target. When blood 761, which has relatively low electrical resistance, is expelled in response to the generation of a vacuum of approximately 100 torr, waves of RF energy 783 are able to propagate through the connective tissue or the fatty tissue therebelow of drawn skin 759, rather than being directed through the blood vessels if blood were not expelled. The path of minimal resistance for the flow of electrical current of RF field 784 is therefore not directed through the expelled blood 761, but rather through the connective tissue perpendicular to the upper skin surface. The large proportion of RF energy 783 which is absorbed within drawn skin 759 is able to uniformly heat the collagen-rich reticular dermis and promote skin contraction for the removal of wrinkles. Depending on the depth penetration, which is a function of the frequency of RF source 783 as well known to those skilled in the art, RF field 784 may impinge upon the cellulite or fat level which is disposed below the reticular dermis and cause skin contraction at the cellulite depth or the softening of fat. When a higher-level vacuum of approximately 400 torr is generated, pain signals are inhibited and the treatment is painless.

FIG. 30 illustrates apparatus 775 which comprises a vacuum chamber 795 that is suitable for effecting vacuum-assisted treatments in conjunction with a bipolar RF source 793. An array of electrode pairs 787 suitable for inducing bipolar field 797 generated at a frequency ranging from 0.2-4 MHz is positioned on the cover 788 of vacuum chamber 795, and the number of electrode pairs 787 may vary from 1 to 100, depending on the size of cover 788 and the depth of treatment. A bipolar field 797 generated at an energy density of 30 J/cm$^2$ and a frequency of 450 KHz is suitable. Cover 788 may be opaque to monochromatic light when RF source 793 is the sole source of energy that is used for the treatment of a skin disorder. Cover 788 may be transparent to monochromatic light when a skin treatment is effected by means of bipolar RF source 793 in addition to a pulsed light source Vacuum chamber 795 is adapted to expel blood to the periphery thereof, and the connective tissue within drawn skin target 799 is therefore able receives the majority of the energy of RF field 797, which normally would be diverted to the blood vessels located with skin target 799 constituting paths of least electrical resistance without influence of the blood expelling vacuum chamber, so as to achieve an efficacious treatment. A prior art treatment, such as one conducted by Syneron, Israel which utilizes the blood flow path in order to heat portions of the tissue, as explained by N. Sadick et al, "Selective Electro-Thermolysis in Aesthetic Medicine: A Review", Lasers in Surgery and Medicine 34:91-97 (2004), is not capable of inhibiting pain by the skin flattening technique of the present invention. Similarly, a prior art technique carried out by means of the Aluma produced by Lumenis, USA, and described by M. Goldman in "Treatment of Wrinkles and Skin Tightening using Bipolar Vacuum-Assisted Radio Frequency Heating of the Dermis", Lumenis, whereby skin is drawn in response to a small vacuum level of 28 mmHg between two parallel electrodes parallel to the skin is not capable of inhibiting pain by the skin flattening technique of the present invention.

Figure 35:
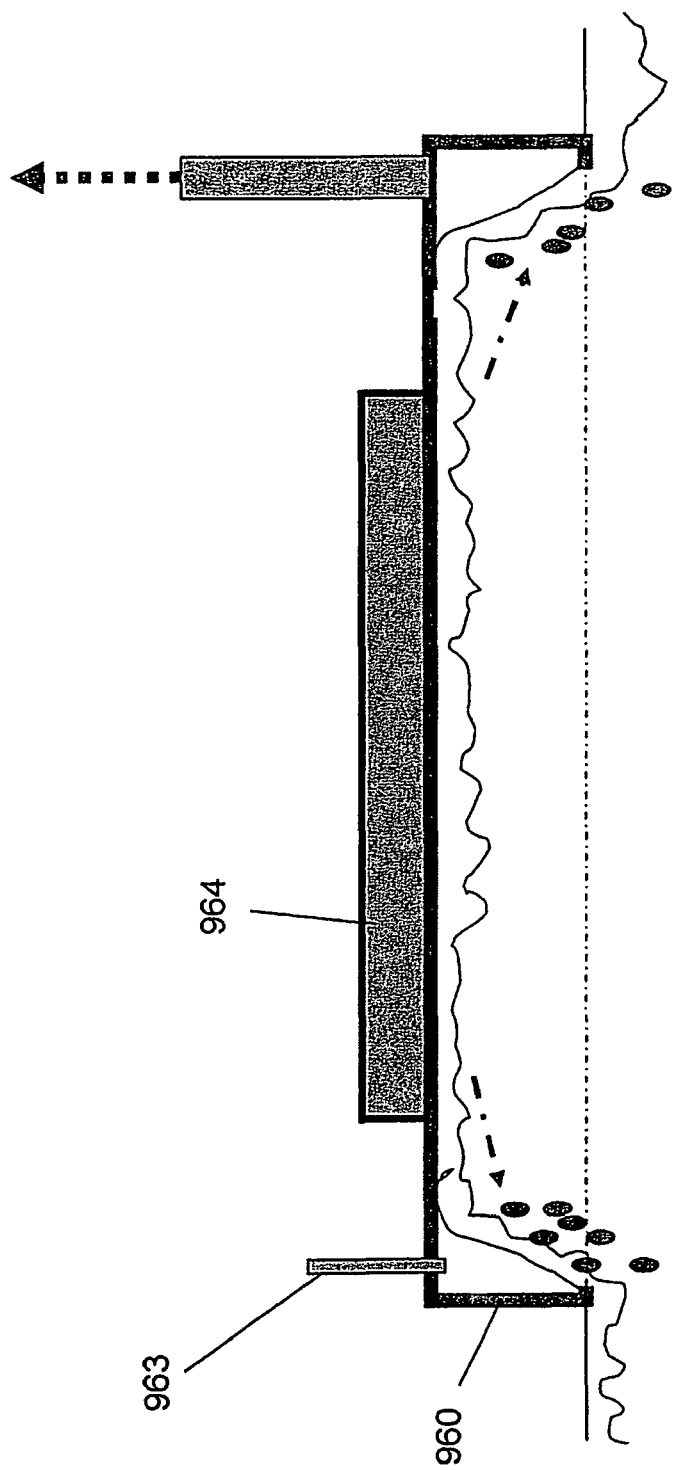
FIG. 35 schematically illustrates a vacuum chamber provided with a pressure sensor.

FIG. 35 illustrates a vacuum chamber 960 which is suitable for a pain inhibiting dermatological treatment by means of an electromagnetic source applied through transmitting element 964. Vacuum chamber 960 is provided with pressure sensor 963 for measuring the air pressure therewithin, so as to determine whether the applied vacuum level is sufficient to inhibit the transmission of pain signals. Pressure sensor 963 may also be used in a closed loop control system whereby the vacuum pump speed is varied in response to the detected vacuum level, in order to achieve a desired level of pain inhibition. The operator normally sets the target pressure level within vacuum chamber to a value ranging between 400-600 mmHg.

Figure 42A:
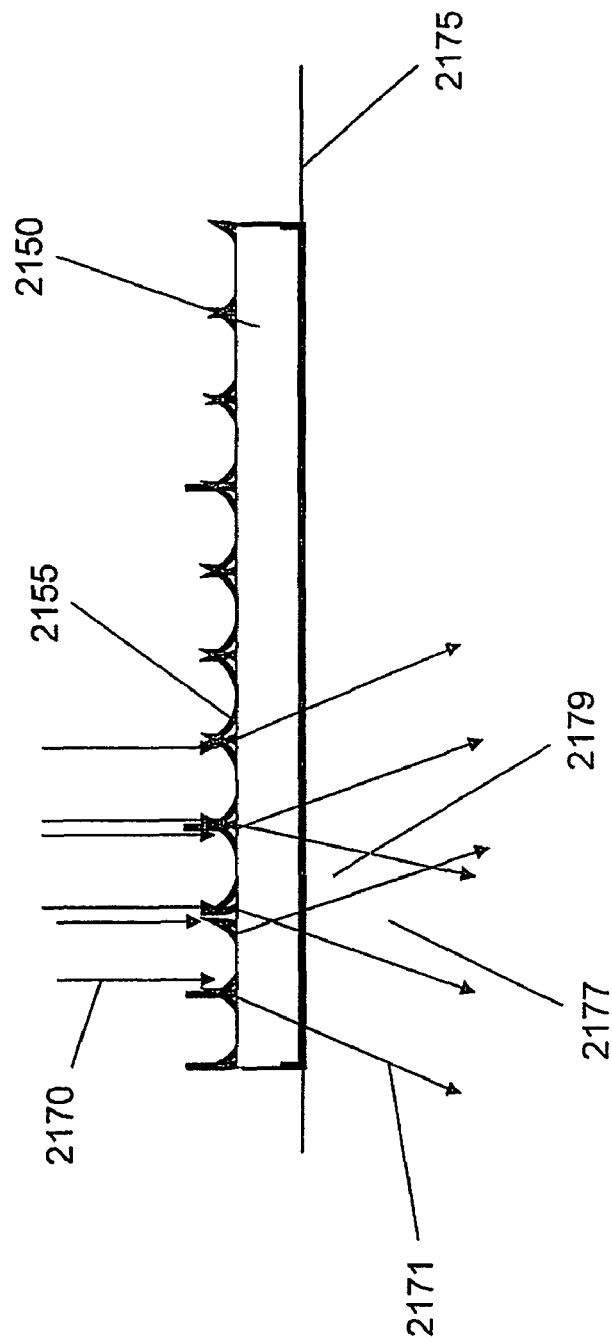
FIG. 42a schematically illustrates a side view of an array of diverging lenses, for an improved rate of healing for tissue that has been treated by laser treatment light.
Figure 42B:
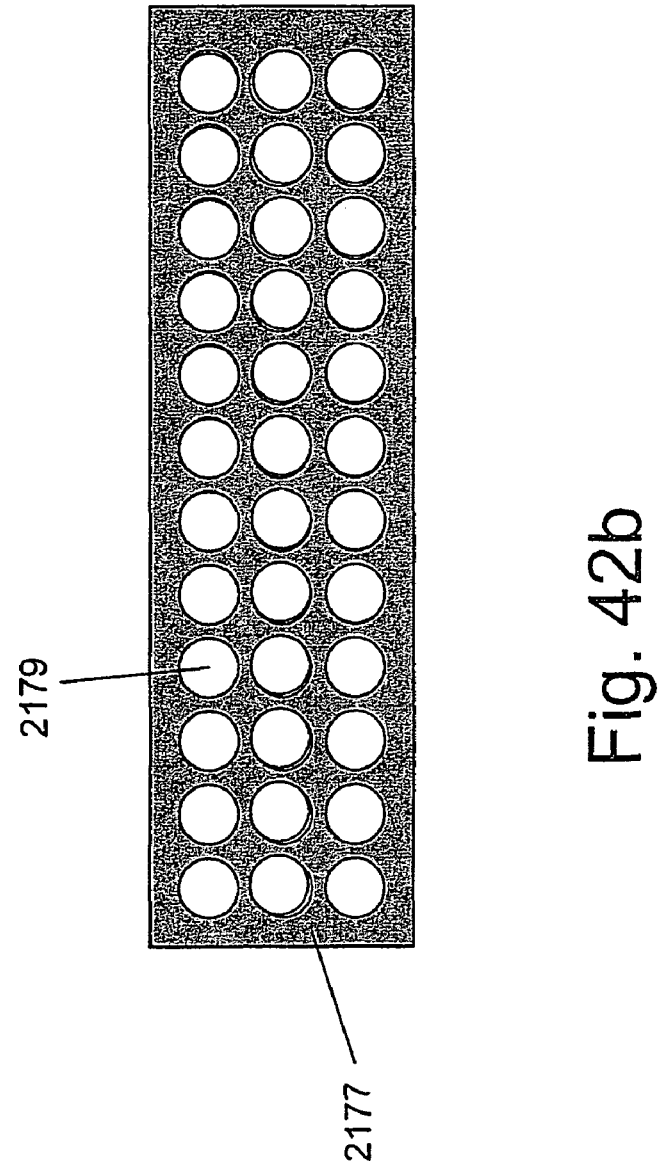
FIG. 42b schematically illustrates in plan view the energy distribution of the treatment light transmitted through the array of lenses of FIG. 42a onto the underlying skin surface.

FIGS. 42a and 42b illustrate an additional embodiment of the present invention wherein an array of divergent lenses is provided, for an improved rate of healing for tissue that has been treated by laser treatment light. The relatively high vacuum level that is generated in order to achieve pain inhibition provides an additional advantage in terms of limiting the degree of scattering by the treatment light. If a relatively high vacuum level were not generated within the vacuum chamber, the treatment light would be scattered to a greater degree by the molecules and collagen bundles within the skin, and an array of divergent lenses would further increase the degree of scattering so that the treatment light would not be efficacious.

As shown in FIG. 42a, the proximal face of transmitting element 2150 of the vacuum chamber has an array of small concave lenses 2155. Lenses 2155 are divergent so that treatment light 2170 which is substantially perpendicular to skin surface 2175 generates ray of light 2171 that are oblique with respect to skin surface 2175. Due to the divergence of exit rays 2171, regions of higher energy density 2177 resulting from constructive overlap of the exit rays and regions of lower energy density 2179 resulting from the lack of overlap of the exit rays are produced. Transmitting element 2150 is advantageous in that a skin target underlying regions of lower energy density 2179 achieve a faster rate of healing due to the reduced thermal damage thereat. On the other hand, increased treatment efficacy is achieved in regions of higher energy density 2177.

FIG. 42b schematically illustrates in plan view the energy distribution of the treatment light transmitted through the array of lenses 2155 onto the underlying skin surface. The regions of lower energy density 2179 are shown as white circles, and the regions of higher energy density 2177 are shown are shown as grey regions surrounding a corresponding white circle.

The diameter of lenses 2155 may vary from 0.5 mm to 3 mm. The negative focal length may be 1-5 times the diameter of the lens. The array is a dense array, such as a hexagonal array of lenses arranged such that each lens is tangential to six adjacent lenses. For 1-mm diameter lenses, the lens density is approximately 1 lens/mm$^2$. Lenses 2155 may be produced from plastic, glass or sapphire and purchased from a large number of lenslet array manufacturers. They may also be produced as a holographic element from HoloOr Ltd., Israel.

An array of lenses 2155 is particularly suitable for skin tightening. When a laser beam generated by an Alexandrite laser having a wavelength of 755 nm or generated by an Nd:YAG laser having a wavelength of 1064 nm wavelength is transmitted through transmitting element 2150 into the flattened skin, the skin target from which blood vessels have been expelled supports a deeper penetration of light and a larger absorption thereof by collagen. Another suitable laser is one identical to a laser produced by DDC Technologies, Inc., USA. Each of these lasers may be operated for a duration of 0.5-5 seconds in order to heat the skin to a temperature of approximately 55° C. at a depth of approximately 1-2 mm. The average laser power is 80 W and the energy density is approximately 15-50 J/cm$^2$.

Figure 19:
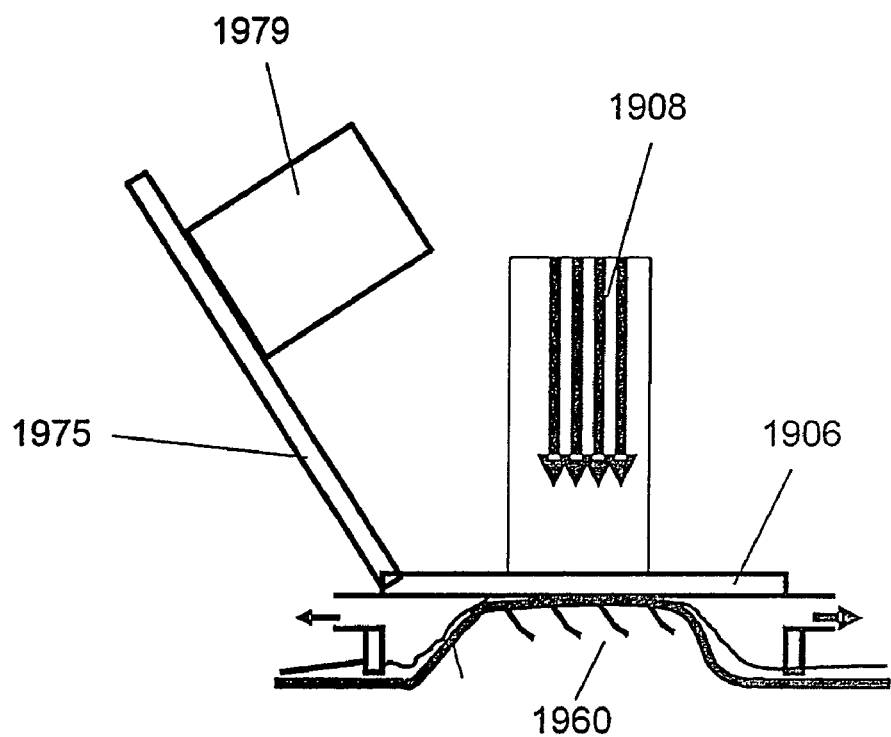
FIG. 19 is a schematic drawing of an exemplary skin cooling device, which is suitable for the apparatus of FIG. 16.

FIG. 19 illustrates an exemplary skin cooling device which is suitable for the pain alleviating apparatus of the present invention. Since the vacuum chamber is configured so as to ensure that a skin target contacts the transmitting element when a vacuum is applied, as described hereinabove, skin cooling is optimized when transmitting element 1906 is directly cooled. Accordingly, thermally conducting plate 1975, which is cooled by thermoelectric chiller 1979, or alternatively by means of a chilling liquid flowing over the conducting plate, contacts transmitting element 1906, in order to conduct the heat generated by the treated skin target 1960 from the transmitting element. The treatment handpiece is provided with chiller 1979 so as to prevent an increase in temperature of the epidermis, which may be damaged if the skin is relatively dark, e.g. Fitzpatrick skin type 4-6. In order to improve the compactness of the skin cooling device, plate 1975 is positioned obliquely with respect to transmitting element 1906 without interfering with the propagation of light beam 1908. It will be appreciated that pain alleviation is achieved by application of a vacuum, which brings the skin in contact with the transmitting element, and not by means of the chiller. As described in Example 8 hereinbelow, pain relief was noticeable during experimentation performed in conjunction with vacuum-assisted, light-based treatments without employment of a skin chiller.

Figure 45:
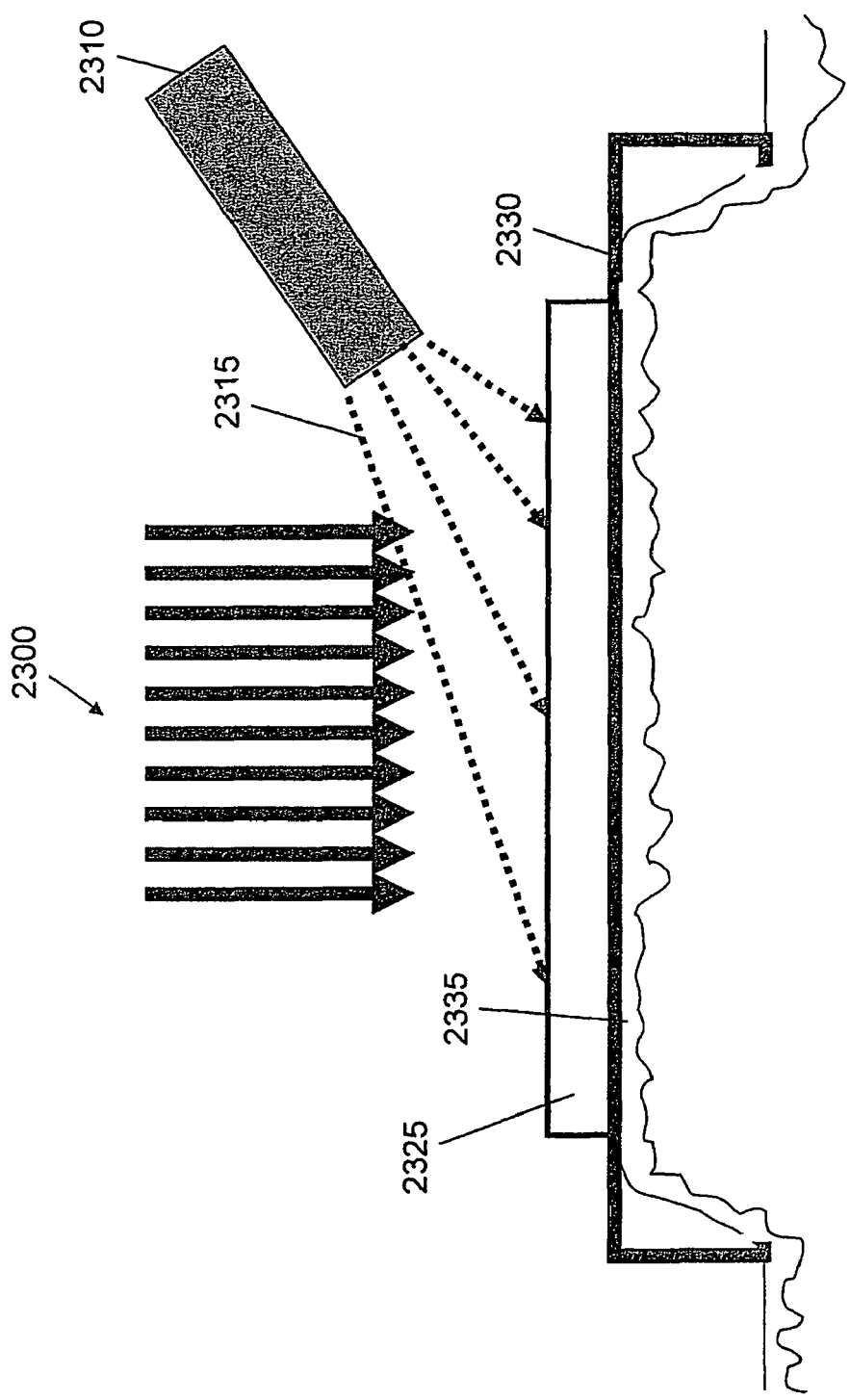
FIG. 45 schematically illustrates a skin chiller that emits a skin chilling spray.

As shown in FIG. 45, the transmitting element may be alternatively cooled by applying a low temperature spray, such as produced by Dermachill, USA, to the transmitting element. Apparatus 2300 comprises pressurized can 2310, from which chilling vapors 2315 are sprayed onto transmitting element 2325 of vacuum chamber 2330, in order to chill transmitting element 2325 and underlying flattened skin target 2335. Such a chiller, which is provided with the Alexandrite laser produced by Candela Corporation, USA, chills the skin directly so that the epidermis achieves a very low temperature of less than 0° C. Due to the very low temperature of the epidermis, the effect of a chilling operation is noticeable for a period on the order of milliseconds rather than seconds, and therefore the chilling operation effectively protects the epidermis without chilling deeper skin regions. By selecting a transmitting element 2325 of a sufficiently thin thickness, the chiller is capable of chilling skin target 2335 as if transmitting element 2325 were not present. A transmitting element 2325 having a width of 150-500 microns and made from highly thermally conductive material such as sapphire is capable of chilling the skin with a spray which is regularly applied on uncovered skin. Epidermal chilling by the spray is made possible when the thermal relaxation time of a sapphire transmitting element is equal to, or less than, the thermal relaxation time of the epidermis, which is approximately 0.5 msec. Thin sapphire transmitting elements, e.g. having a thickness of 0.5 mm and a diameter of 1 inch may be obtained from Esco Products Inc., USA.

Apparatus for Preventing Gel-Caused Obstruction

The apparatus may be advantageously provided with means to prevent the obstruction of the vacuum chamber conduits by heat releasing gel applied to the skin target prior to the treatment. As shown in FIGS. 24A and 24B, gel 185 is squeezed to the periphery of vacuum chamber 180 after application of a vacuum. When vacuum chamber 180 is displaced from skin area 190 to skin area 192, further gel is squeezed and accumulates, as shown in FIG. 24B. The gel is eventually aspirated into the vacuum chamber conduits, causing a significant risk of obstruction thereto when a large-diameter treatment beam normally associated with an IPL unit is used and necessitating the employment of a correspondingly large-diameter vacuum chamber. Without emptying means to prevent passage of the gel, a large quantity of gel is liable to be drawn through the conduits and to the vacuum pump, eventually resulting in the malfunction of the latter and in less efficacious treatments. Also, aspirated gel tends to contaminate the vacuum chamber, and the cleaning or sterilization of the vacuum chamber prior to the treatment of another patient is difficult.

Referring back to FIG. 16, vacuum chamber 1901 has two passageways 1930 through which air is evacuated therefrom. Each passageway 1930, which is in fluid communication with the interior of vacuum chamber 1901, is defined by outer wall 1924, vertical portion 1926, and cylindrical horizontal wall 1930 connected to both outer wall 1924 and vertical portion 1926. The distal end of vertical portion 1926 is connected to transmitting element 1906, vertically spaced above, and interiorly spaced from, the distal end of outer wall 1924 placed on skin surface 1965, and is connected to vertical portion 1926 of passageway 1930. The top of horizontal passageway wall 1930 is vertically spaced above outer wall 1924, and vacuum chamber 1901 is therefore considered to be U-shaped. Each horizontal wall 1930 terminates with an opening 1917, which is separated from the distal end of outer wall 1924 by P and is laterally separated from centerline 1969 of vacuum chamber 1901 by J. While the gel may be drawn by the applied vacuum or may laterally slide from skin target 1960 after being pressed by transmitting element 1906, dimensions P and J are selected so as to ensure that the volume of the passageways 1930 and of the chamber interior between wall 1924 and the adjacent surface of drawn skin target 1960 is sufficiently large to prevent the obstruction of corresponding opening 1917 by gel 1963. For example, a vacuum chamber having a height K of 2 mm, a wall opening diameter of 3 mm, a separation P of 10 mm from the opening to the distal end of the wall, and a lateral separation J of 20 mm from the vacuum chamber centerline to the opening is sufficient to prevent obstruction of the opening by gel.

Figure 17:
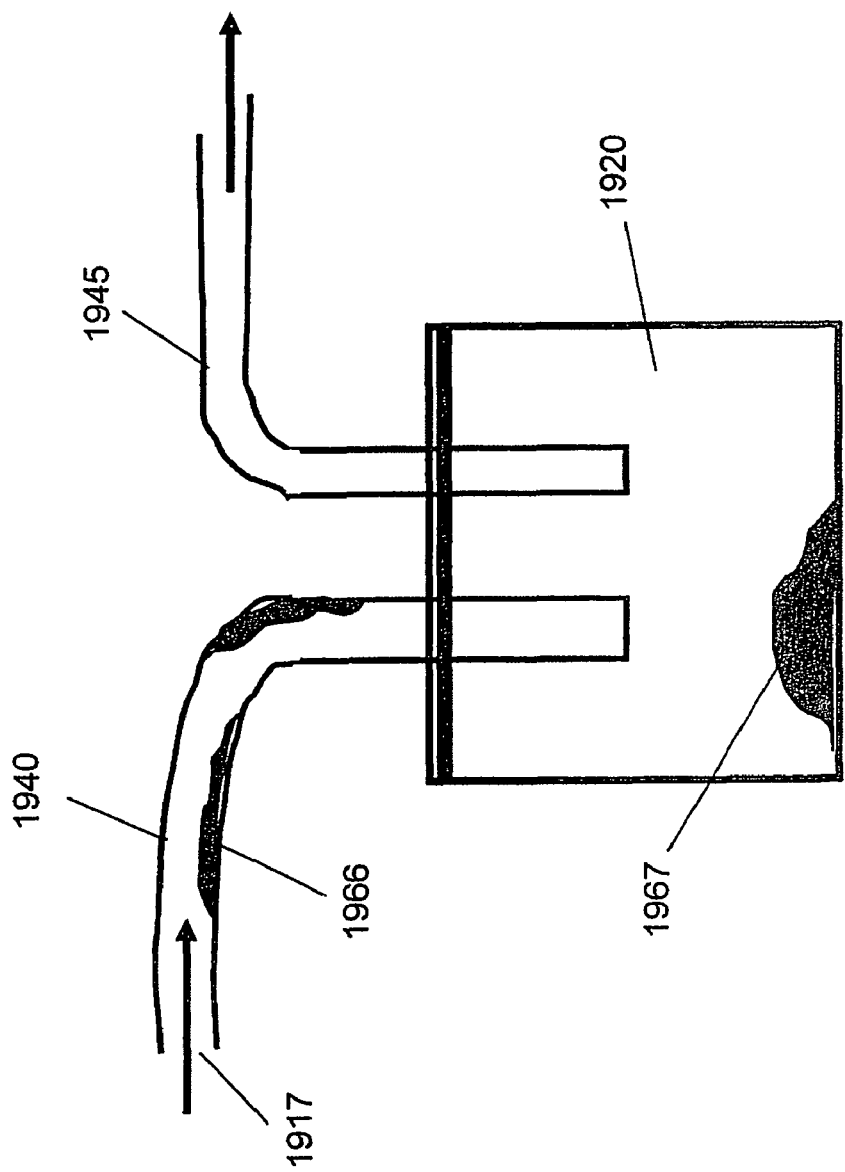
FIG. 17 is a schematic drawing of an exemplary trap, for preventing the passage of gel to a vacuum pump.

FIG. 17 illustrates another arrangement for preventing vacuum pump suction of gel. The arrangement includes trap 1920, conduit 1940 through which gel and air are drawn from the vacuum chamber to trap 1920, and conduit 1945 through which air is drawn from trap 1920 to the vacuum pump, all of which may be disposable. Air evacuated from the vacuum chamber through opening 1917 flow through conduits 1940 and 1945 until introduced to the inlet port of the vacuum pump. The gel which is evacuated from the vacuum chamber collects within trap 1920. Trap 1920 is periodically emptied so that the accumulated gel does not rise above the inlet of conduit 1945. Trap 1920 and conduits 1940 and 1945 are preferably made from a plastic hydrophilic material, to urge the gel to cling to the walls thereof rather than to be drawn through the conduits to the vacuum pump. As shown, gel 1966 clings to the walls of conduit 1940 and gel 1967 is collected on the bottom of trap 1920. The conduits may be suitably sized to prevent the passage of gel to the vacuum pump. For example, the diameter of conduit 1940 at the vacuum wall opening is 30 mm and narrows to a diameter of 10 mm at the discharge to trap 1920, and the diameter of conduit 1945 at the inlet side is 5 mm and is 10 mm at the discharge side in the vicinity of the vacuum pump inlet port.

Other arrangements for preventing vacuum pump suction of gel may also be employed. For example, the gel may be bound to a suitable ion exchange resin introduced into trap 1920 and thereby be prevented from being drawn through conduit 1945. If so desired, a filter may be provided at the inlet of conduits 1940 and 1945.

Alternatively, gel may be prevented from exiting the vacuum chamber by increasing the diameter of conduit 1940 at the vacuum wall opening. Consequently, the inwardly directed force acting on the gel which has laterally slid from a drawn skin target by means of the atmospheric air introduced to the vacuum chamber via conduit 1940 during a vacuum release mode is sufficient to prevent the gel from exiting the vacuum chamber. A hydrophobic coating, such as silicon or teflon, may be applied onto the vacuum chamber walls, so that the gel will be prevented from adhering to the vacuum chamber walls, particularly during a vacuum release mode. Instead of adhering to the vacuum chamber walls, the gel falls to the skin surface. Advantageously, gel is therefore not transported to another skin target during the repositioning of the handpiece, but rather assumes the shape of the distal end of the vacuum chamber walls. If the distal end of the vacuum chamber walls is circular, for example, the gel that falls to the skin surface during a vacuum release mode is also circular, indicating to the health professional that is supervising the treatment that the given skin surface has already been impinged by the treatment light.

Figure 18:
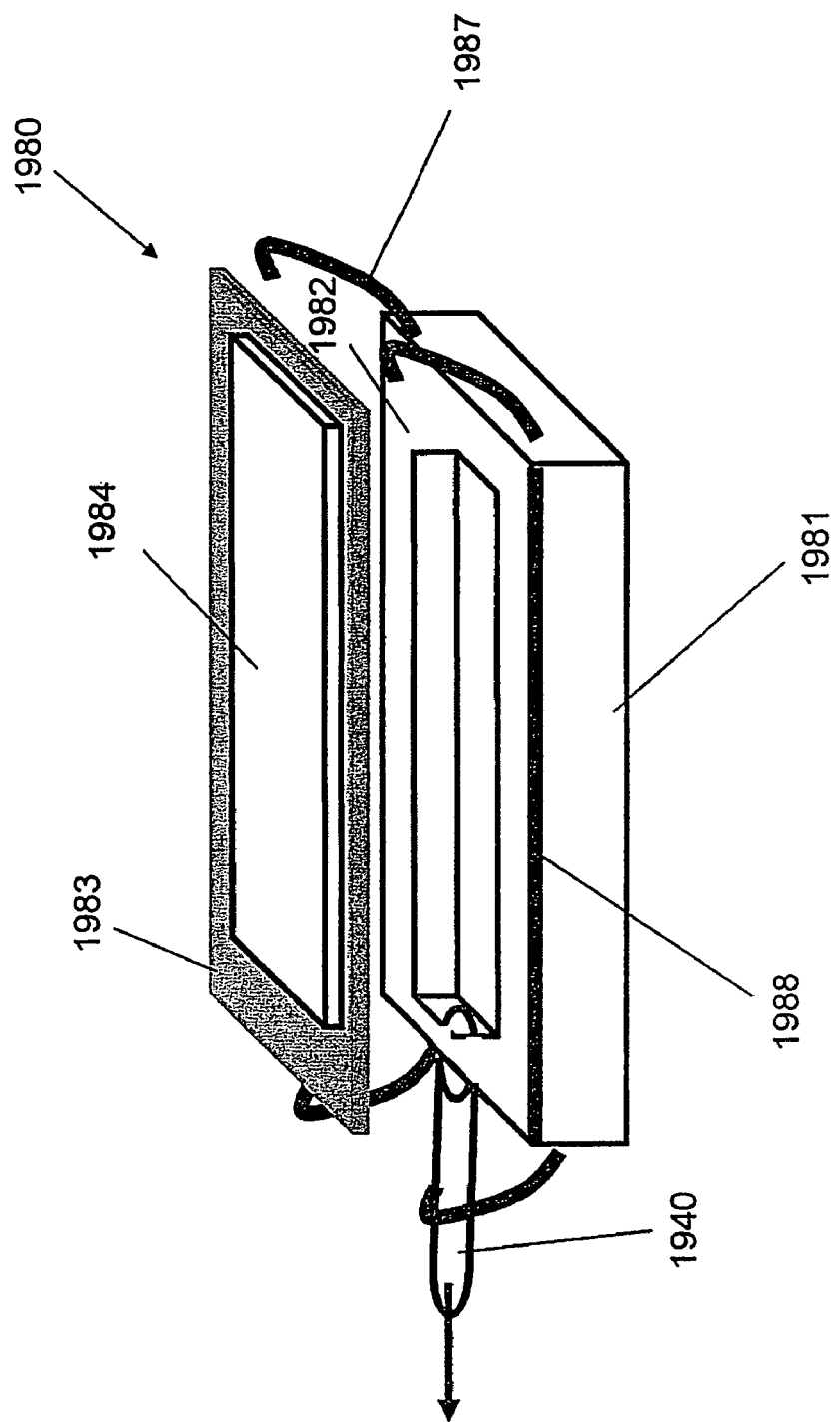
FIG. 18 is a schematic perspective drawing of apparatus in accordance with another embodiment of the invention, illustrating a detachable upper portion of a vacuum chamber.

In FIG. 18, apparatus 1980 comprises a vacuum chamber having a detachable upper portion, so that the gel retained by the vacuum chamber interior walls may be removed therefrom, such as by dissolving the gel with salt or with any other suitable dissolving agent. Apparatus 1980 comprises upper portion 1983 having an open central area, transmitting element 1984 attached to upper portion 1983, vacuum chamber walls 1981, vacuum chamber cover 1982 perpendicular to walls 1981 and suitably sized so as to support upper portion 1983, and a plurality of attachment clips 1987 pivotally connected to a corresponding vacuum chamber wall 1981 for detachably securing upper portion 1983 to vacuum chamber cover 1982. Thin compliant sealing element 1988 is preferably attached to the periphery of vacuum chamber cover 1982, to prevent infiltration of atmospheric air into the vacuum chamber. Conduit 1940 is shown to be in communication with the interior of the vacuum chamber.

Figure 25:
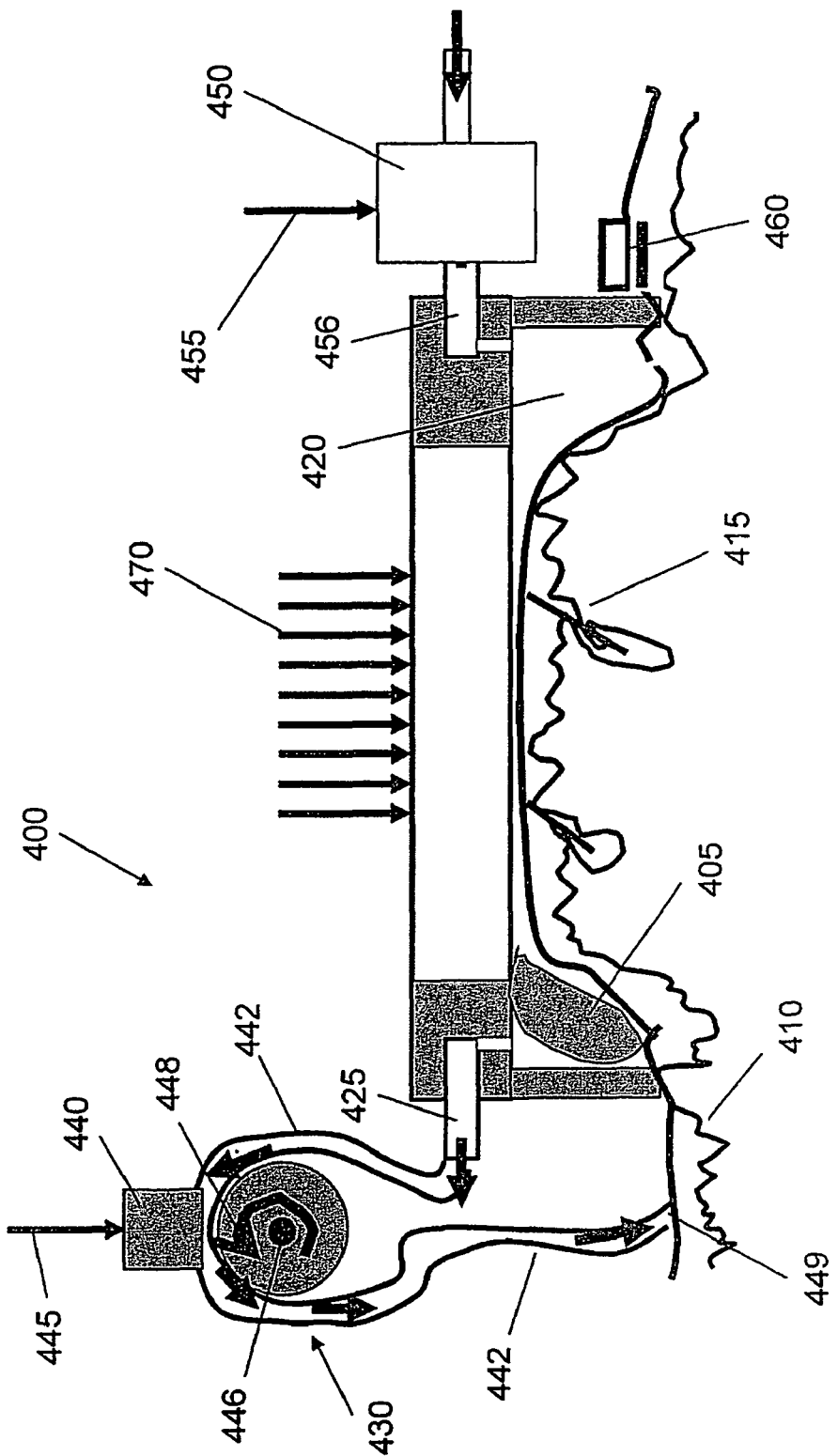
FIG. 25 schematically illustrates a vacuum chamber to which a vacuum is applied by means of a peristaltic pump.

FIG. 25 illustrates another embodiment of apparatus for preventing the obstruction of vacuum chamber conduits by heat releasing gel during vacuum-assisted light-based treatments of the skin. Apparatus 400 comprises vacuum chamber 420, peristaltic pump 430, vacuum controller 440, control valve 450, and micro-switch 460.

The vacuum applying mode is initiated upon transmission of signal 445 to controller 440, following which peristaltic pump 430 is activated. Peristaltic pump 430 comprises hose 442 connected to conduit 425 in communication with the interior of vacuum chamber 420 and rotatable hub 446, from which a plurality of shoes and/or rollers 448 (referred to hereinafter as "pressing elements") radially extend. As hub 446 rotates, the pressing elements sequentially squeeze a different region of hose 442 and a volume of fluid entrapped by two adjacent pressing elements is thereby forced to flow unidirectionally through hose 442 by a positive displacement action towards end 449 thereof. Consequently, when peristaltic pump 430 is activated, air is drawn from the interior of vacuum chamber 420 to generate a vacuum therein ranging from 0-1 atmospheres. If a considerable amount of gel 405 accumulates within the periphery of vacuum chamber 420, the gel is also forced to flow within hose 442 without causing any obstruction to the latter. The gel that is discharged from end 449 of hose 442 falls onto skin surface 410, indicating that an adjoining skin target 415 has undergone a light-based treatment.

Micro-switch 460, or any other suitable skin contact detector, is adapted to sense the placement of the handpiece or of vacuum chamber chamber 420, onto skin target 415. Micro-switch 460 generates signal 445 upon sensing the placement of vacuum chamber 420 on skin target 415. Control valve 450 is triggered by a light detector (not shown), which generates signal 455 upon detecting the termination of the light-based treatment pulse 470. Control valve 450 is opened after the generation of signal 455, to introduce atmospheric pressure air 452 to the interior of vacuum chamber 420 via passageway 456 and to thereby initiate the vacuum release mode. Signal 455 is also transmitted to controller 440, to deactivate peristaltic pump 430. The described automatic operation of peristaltic pump 430 therefore prevents the patient from suffering pain during the associated treatment. If so desired, the operation of peristaltic pump 430 may be manually overridden.

It will be appreciated that a peristaltic pump or a contact detector may be employed in conjunction with any other embodiment of the invention.

In another embodiment, the vacuum pump is an air pump. When air is evacuated from the vacuum chamber, a piston (not shown) which is normally closed by a spring is opened to allow air to be aspirated. During the vacuum release mode, the piston is set to its original position, returning air to the vacuum chamber and any aspirated gel to the skin surface.

Figure 27:
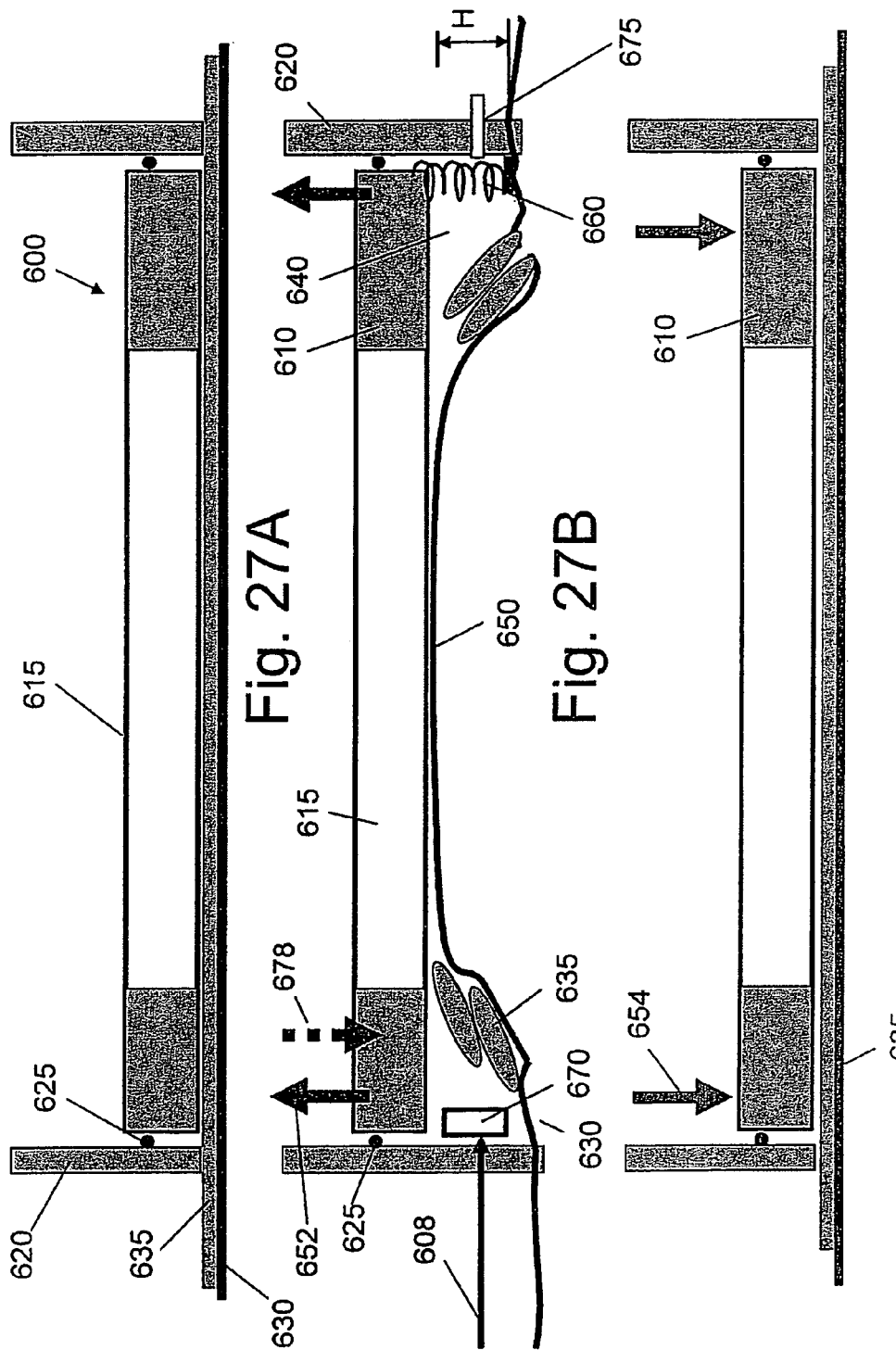
FIGS. 27A-C illustrate the production of a vacuum chamber by a vertically displaceable cover in three stages.

FIGS. 27A-C illustrate another embodiment of the invention wherein a vacuum pump is not needed for vacuum-assisted light-based treatments of the skin. Apparatus 600 comprises a vertically displaceable cover 610 to which transmitting element 615 is secured, chamber walls 620 in which vertically displaceable cover 610 is mounted, and sealing element 625 which is secured to the outer periphery of cover 610. Chamber walls 620 surround, and are of a similar shape as, cover 610.

When cover 610 is in its lowermost position, as shown in FIG. 27A, the cover is flush with skin surface 630 on which is applied a layer of gel 635.

In this position, air is prevented from infiltrating between cover 610 and skin target 630, e.g. by means of a sealing element externally affixed to walls 620. When a proximally directed force represented by arrows 652 is applied to cover 610, as shown in FIG. 27B, the cover is raised while sealing element 625 resiliently contacts walls 620. Apparatus 600 is configured such that distal displacement of cover 610 is prevented after having been raised, without application of a subsequent distally directed force. While cover 610 is raised, a vacuum chamber 640 is produced internally to chamber walls 620, due to the increased volume between cover 610 and skin surface 630 while air is prevented from infiltrating therein. The vacuum generated within vacuum chamber 640 as a result of the proximal displacement of cover 610 ranges from 0-1 atmospheres and is suitable for drawing skin target 650 towards the displaced cover 610 as shown, in order to be subsequently impinged by a treatment pulse. When a distally directed force represented by arrows 654 is applied to cover 610 following the light-based treatment, as shown in FIG. 27C, cover 610 returns to its lowermost position in preparation for displacement to the next skin target. Aeration tube 675 in communication with a manually operated or control valve (not shown) may be employed to quicken distal displacement of cover 610 during a vacuum release mode by introducing atmospheric air to vacuum chamber 640 upon conclusion of the skin target treatment.

Proximally directed force 652 or distally directed force 654 may be generated manually by means of handles (not shown) attached to cover 610, or electrically by means of a plurality of solenoids 670 and/or by means of a spring assembly 660 deployed around the periphery of cover 610, as well known to those skilled in the art to achieve balanced displacement of the cover. Solenoids 670 are mounted such that one side of a solenoid is mechanically connected to displaceable cover 610 and the other side thereof is connected to a chamber wall 620. When electrical actuation of cover 610 is employed, command 608 generated by skin contact sensor 460 (FIG. 25) is transmitted to spring assembly 660 or solenoids 670 after a predetermined time delay following contact between cover 610 and skin surface 630, causing cover 610 to be proximally displaced upward with a proximally directed lifting force 652 comparable to that of a piston. By properly controlling solenoids 670, height H of the drawn skin target 650 relative to the adjoining skin surface 630 can be adjusted. Height H of the drawn skin is generally increased as the treatment spot is increased. For example, height H may be 2 mm for a treatment spot of 40 mm, while height H may be 0.5 mm for a treatment spot of 3 mm. Alternatively, height H may be adjusted to ensure that skin target 650 contacts transmitting element 615 for pain alleviation.

At times, a sufficiently high vacuum level for effecting a light-based treatment may not be produced within vacuum chamber 640, due to a malfunction. If a health professional notices that the distance between skin target 650 and transmitting element 615 is greater than a predetermined distance for effective treatment with an IPL or laser, the automatic control of cover 610 may be overridden. By reversing the direction of current within solenoids 670, one-time distally directed force 678 may be generated which urges cover 610 towards skin surface 630.

When the distal end of the treatment light source is positioned on chamber walls 620, cover 610 has a relatively low weight of approximately 50 gm. However, if the treatment handpiece is positioned on cover 610 such that the combined weight of the cover and handpiece is approximately 1 kg, the capacity of solenoids 670 needs to be increased, in order to raise both the cover and handpiece and to produce a vacuum within chamber 640.

Apparatus 600 advantageously provides low power consumption and increased compactness. When the handpiece is positioned on chamber walls 620, solenoids 670 are energized by a battery without need of draining wall current and only when cover 610 is needed to be vertically displaced. The energy requirement for raising cover 610 to a height of 2 mm is approximately 0.5 J for a typical 500-pulse large area treatment on the back or legs. Therefore an inexpensive 1.5 V battery is suitable for more than 1000 treatments.

Apparatus 600 also advantageously prevents accumulation of gel. When skin target 650 is drawn during a vacuum applying mode as shown in FIG. 27B, gel 635 is displaced to a peripheral skin area within vacuum chamber 640. However, when cover 610 returns to its original lowermost position as shown in FIG. 27C, skin target 650 is retracted. Gel 635 is then substantially uniformly spread underneath cover 610, due to the pressure applied by cover 610. Similarly when apparatus 600 is repositioned to another skin target, gel 635 does not accumulate.

The proximally directed force may be supplemented by means of a vacuum pump, which may be needed if an excessive amount of gel is applied to skin surface 630 or if it desired to indicate that skin target 650 has undergone a light-based treatment as described hereinabove.

A Dual Air-Gel Vacuum Pump

Figure 31:
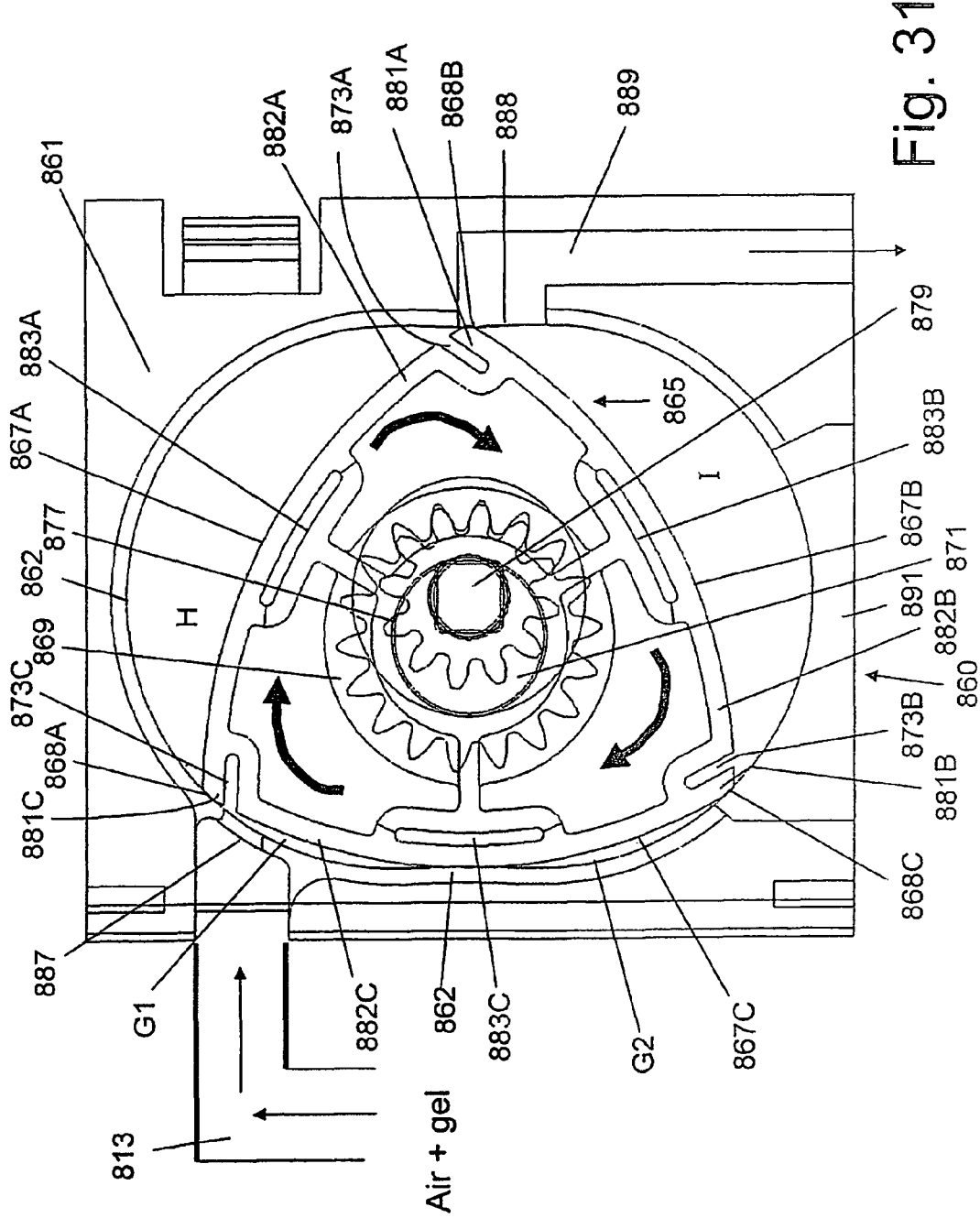
FIG. 31 illustrates a plan view of a Wankel type vacuum pump with its cover removed, according to one embodiment of the invention.

FIGS. 31 and 32 illustrate a dermatological pump capable of generating a vacuum level that is sufficient for efficacious light-based treatments and/or pain inhibition needs to reliably draw both air and gel, without leading to pump failure.

FIG. 31 illustrates a plan view of one embodiment of a vacuum pump in accordance with the present invention that is suitable for drawing both air and gel. The illustrated pump, which is shown when its cover is removed and is generally designated by numeral 860, is configured in similar fashion to a Wankel mechanism well known in the field of combustion engines, in which a triangular rotor rotates on an eccentric shaft inside an epitrochoidal casing. The pump comprises only 3-5 parts, resulting in simple and low cost production. Pump 860 has a low power consumption ranging from 1-10 W, e.g. approximately 5 W, so that it may be powered by an inexpensive battery, e.g. a rechargeable battery, housed within the treatment handpiece. The extremely low power consumption of the pump is made possible by virtue of the following factors: a) The pump, including its casing, rotor and covers, is made from a self-lubricating material, such as Acetal mixed with Teflon, e.g. having a friction coefficient of 0.05, which minimizes friction and therefore similarly reduces the power consumption. b) A thin layer of gel which is drawn by, and transferred within the various compartments of, the pump adds to the pump lubrication. c) The pump rotor is formed with slots, as will be described hereinafter, so that the rotor may conform to the shape of the casing and flex in response to gel pressurization, thereby reducing resistance to the rotation of the rotor.

Although the gel may provide lubrication for the pump when drawn from the vacuum chamber to the pump cavity, it is desirable that the pump be made from a self-lubricating material to prevent overheating or malfunction thereof since the skin may be covered with a very thin layer of gel, or may not be covered at all by gel, and therefore the pump may not be adequately lubricated.

In the prior art Wankel engines of U.S. Pat. Nos. 5,944,499, 6,106,250, and 6,158,992, each of the three faces of the triangular rotor is involved sequentially with the following four cycles: intake cycle, compression cycle, power cycle and exhaust cycle. Compressible fluids are introduced into an inlet port by the first face of the rotor during the intake cycle, defining a compartment of peak volume between the first face and the casing. At the same time, the second face is driven by the combustion forces and the third face forces out the exhaust gas through the exhaust port. During the compression cycle, the volume of said compartment significantly decreases, causing the introduced fluids to become significantly compressed, whereinafter the compressed fluids are ignited in the power cycle. If an incompressible fluid such as gel were introduced into a Wankel mechanism, the fluid would become excessively pressurized by the force applied by the rotor and the casing during the compression cycle, due to the small chamber volume. The pressurized fluid would then transmit its increased internal force to the rotor, and the apex at the junction of each face is liable to be damaged, e.g. resulting in the formation of a crack, due to the high stress concentration thereat. The pump cover or casing walls are liable to be damaged as well. Prior art Wankel mechanisms are therefore not suitable for reliably delivering incompressible fluids.

In contrast to a prior art Wankel mechanism, the Wankel type vacuum pump of the present invention is suitable for drawing both compressible fluids such as air and incompressible fluids such as gel. Since the rotor is eccentrically mounted, the compartments developed between a rotor face and the surrounding casing have a varying volume, and compressible fluids such as air may therefore be compressed within a compartment having a small volume. In order to accommodate the presence of pressurized gel in a pump compartment having a small volume, the rotor is advantageously formed with a slot in each face. The rotor is therefore able to flex during a compression-exhaust cycle when pressurized gel transmits its increased internal force thereto and thereby prevents rotor failure. The flexing of the rotor also limits the pressure of the gel, which would normally cause the pump cover to separate from the casing if the rotor were not configured with slots and to allow air of atmospheric pressure to infiltrate to the interior of the pump when generating a vacuum.

As shown in FIG. 31, pump 860 comprises casing 861 and triangular rotor 865. Rotor 865 has an outer profile of generally equilateral triangular shape with convexly curved faces 867A-C, and is provided with internal gear 869 secured to a central region of rotor 865 and defining cavity 871. Face 867A extends from apex 868A to 868B, and similarly face 867B extends from apex 868B to 868C and face 867C extends from apex 868C to 868A. Internal gear 869 is intermeshed with external gear 877, which is journaled about shaft 879 rotating internally to cavity 871, such that rotor 865 eccentrically rotates in the rotational direction indicated by the arrows, in a planetary manner about shaft 879 at a speed considerably less than that of shaft 879.

Rotor 865 is formed with end face slots 873A-C and central face slots 883A-C. Each of the end face slots 873A-C is formed in the vicinity of a corresponding apex 868A-C and is substantially perpendicular to the corresponding face 867A-C, causing a discontinuity in the face and dividing the same into two portions 881A-C and 882A-C wherein the shorter portion 881A-C is approximately one-tenth the length of the corresponding longer portion 882A-C. Each of the central face slots 883A-C is formed in rotor 865, adjacent to the centerline of the corresponding face 867A-C and substantially parallel thereto.

Casing 861 is formed with an epitrochoidal inner wall 862 defining a cavity in which rotor 865 rotates. Inner wall 862 is configured such that apexes 868A-C of rotor 865 are in contact with wall 862 throughout the eccentric angular displacement of rotor 865. To ensure that apexes 868A-C of rotor 865 are constantly in contact with inner wall 862 of casing 861, the circumferential length of each of the faces 867A-C is greater than, or equal to, the smallest gap of the rotor cavity between opposite portions of inner wall 862. Since casing 861 and rotor 865 are produced by injection molding to lower production costs, production discrepancies occur at times, e.g. with respect to the operation of the automated production facilities or with a mold formation, causing a discrepancy of up to 0.05 mm. End face slots 873A-C in the vicinity of corresponding apexes 868A-C are formed to ensure that apexes 868A-C on one hand will constantly contact inner wall 862, yet to allow the length of faces 867A-C to contract at regions of inner wall 862 whereat the gap of the rotor cavity is of a reduced dimension.

Three types of compartments G, H, and I, through which a controlled volume of air and gel is sequentially transferred within the pump, are defined by the volume of the cavity between inner wall 862 and a corresponding pair of apexes. Due to the shape of inner wall 862 in which a portion thereof inwardly protrudes, two compartments G are developed, G1 between central face slot 883C and apex 868C and G2 between central face slot 883C and apex 868A. It will be appreciated that other configurations are also suitable wherein only one compartment G is developed.

Compartments G, H, and I are sealed by a Teflon ring surrounding the top and bottom casing covers (not shown), by a Teflon disc having a thickness of approximately 0.1 mm interposed between rotor 865 and each of the top and bottom covers, and additionally by the contact between the apexes and inner wall 862 of the casing.

Pump 860 is operable under three cycles: the intake-expansion cycle, compression-exhaust cycle, and transfer cycle. Each of the compartments undergoes one of these cycles as the corresponding compartment volume changes. In the illustrated orientation of rotor 865, compartment G1 has the smallest volume and is the compartment in which a volume of atmospheric air is transferred in the transfer cycle, compartment H is the compartment in which a volume of air is expanded in the intake-expansion cycle, and compartment I is the compartment in which a volume of air and gel is exhausted in the compression-exhaust cycle. As rotor 865 rotates, air and/or gel are retained in the same compartment and sequentially undergo the compression-exhaust cycle, intake-expansion cycle, and transfer cycle while the volume of said compartment is varied due to the eccentric rotation of rotor 865. Accordingly, in the subsequent cycle to the orientation shown in FIG. 31, compartment I will be the compartment in which a volume of air is transferred in the transfer cycle, compartment G will be the compartment in which a volume of air is expanded in the intake-expansion cycle, and compartment H will be the compartment in which a volume of air and gel is exhausted in the compression-exhaust cycle.

Casing 861 is formed with an inlet 887 for each corresponding conduit of a vacuum chamber, through which air and gel are drawn from the interior of the vacuum chamber to the compartment in which a volume of air and gel is received in the intake-expansion cycle, and an outlet 888 through which the air and gel are discharged to exhaust tube 889 during the compression-exhaust cycle. The distal end of exhaust tube 889 is positioned above a corresponding treated skin site. The gel discharged from exhaust tube 889 is therefore directed to a skin area, indicating that said skin area has undergone a light-based vacuum-assisted treatment, so that the treatment handpiece needs to be repositioned to another skin site.

The expansion of air during the intake-expansion cycle generates the vacuum within the vacuum chamber. After atmospheric-pressure air is transferred within a compartment having a relatively small first volume, e.g. compartment G1, to inlet 887, the volume of the retaining compartment is increased to a second volume, and the pressure of the air is accordingly reduced to be subatmospheric. When this second volume communicates with inlet 887, a volume of air and gel is drawn from the vacuum chamber, due to the lower pressure of this second volume. With respect to the illustrated orientation of rotor 865 in FIG. 31, air and gel are drawn during the intake-expansion cycle from the vacuum chamber to an intake compartment larger in volume than compartment G1 until apex 868C advances beyond inlet 887. During the intake-expansion cycle, air and gel are received in the intake compartment, and the air received therein is incrementally expanded, so as to draw additional air and gel from the vacuum chamber. The continuous rotation of rotor 865 brings compartments I and H to be sequentially in communication with inlet 887, causing additional volumes of air from the vacuum chamber to expand, so that a vacuum of sufficient duration and level for drawing a skin area during a light-based vacuum-assisted may be generated. The evacuation rate of pump 860 may be increased by increasing the rotational speed of shaft 879.

Casing 861 is also provided with exhaust pipe 891 larger in size than exhaust tube 889. Continuous rotation of rotor 865 advantageously directs excessive gel which has not been discharged through exhaust tube 889 to exhaust pipe 891, to prevent the gel from returning to the vacuum chamber. Following additional rotation of rotor 865, air not discharged through exhaust tube 889 or exhaust pipe 891, which may be a volume of less than 5% of the volume of the illustrated compartment I of FIG. 31, is retained in compartment G2. As rotor 865 continues to rotate, the atmospheric-pressure air retained in compartment G2 is transferred to the vicinity of inlet 887, as represented by compartment G1. During the intake-expansion cycle, the transferred atmospheric-pressure air is mixed with the air drawn from the vacuum chamber and thereby limits the vacuum level generated during the intake-expansion cycle. The configuration of pump 860 whereby some atmospheric-pressure air remains in the pump cavity and is not discharged through exhaust tube 889 and exhaust pipe 891 advantageously provides means for limiting the vacuum level generated within the vacuum chamber to approximately 0.05-0.1 atmospheres, a vacuum level that is sufficient for efficacious light-based treatments and/or pain inhibition.

Figure 32A:
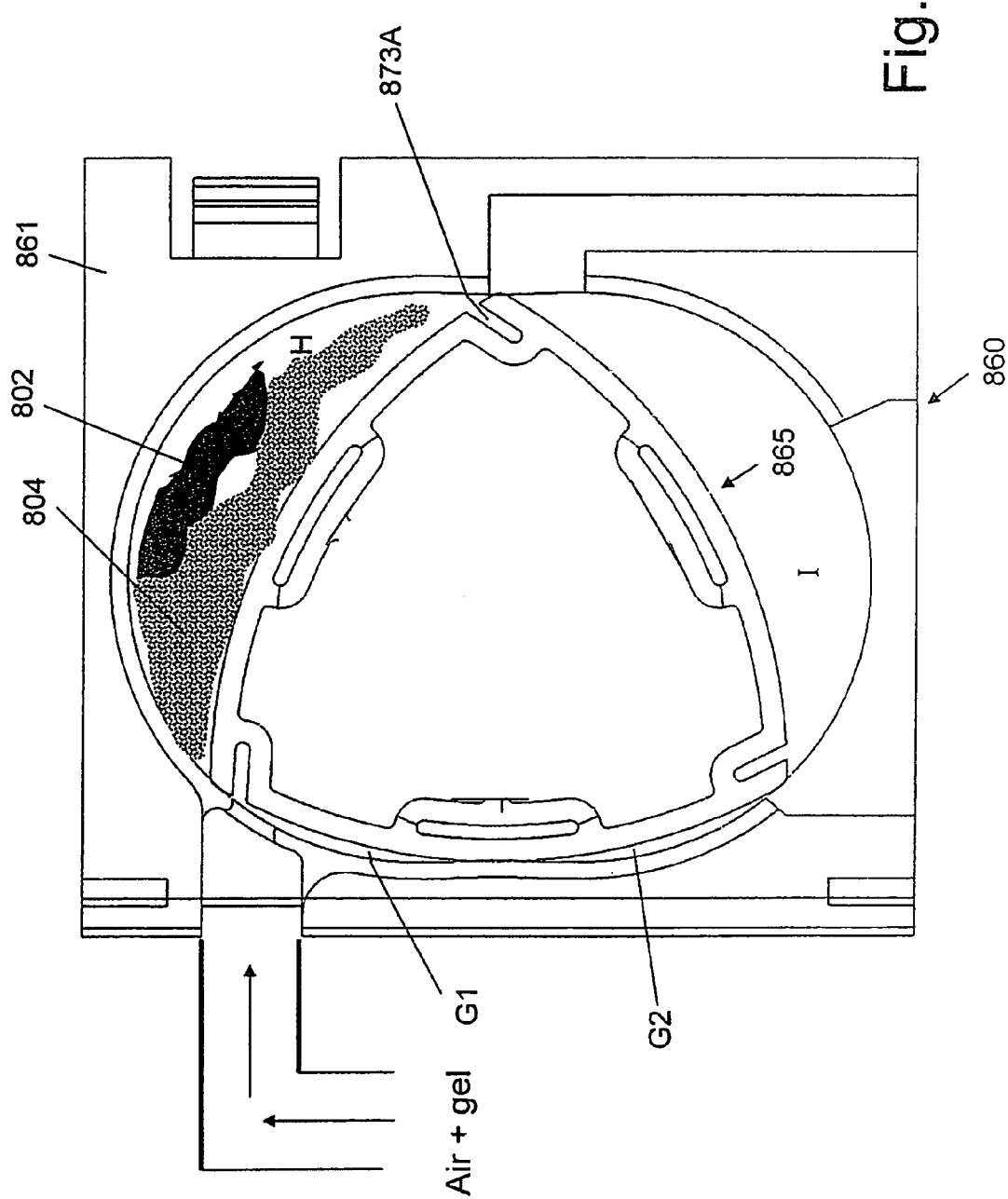
FIGS. 32a and 32b schematically illustrate the elastic deformation of a pump rotor as gel is transferred within the pump from an intake-expansion cycle to a compression-exhaust cycle.
Figure 32B:
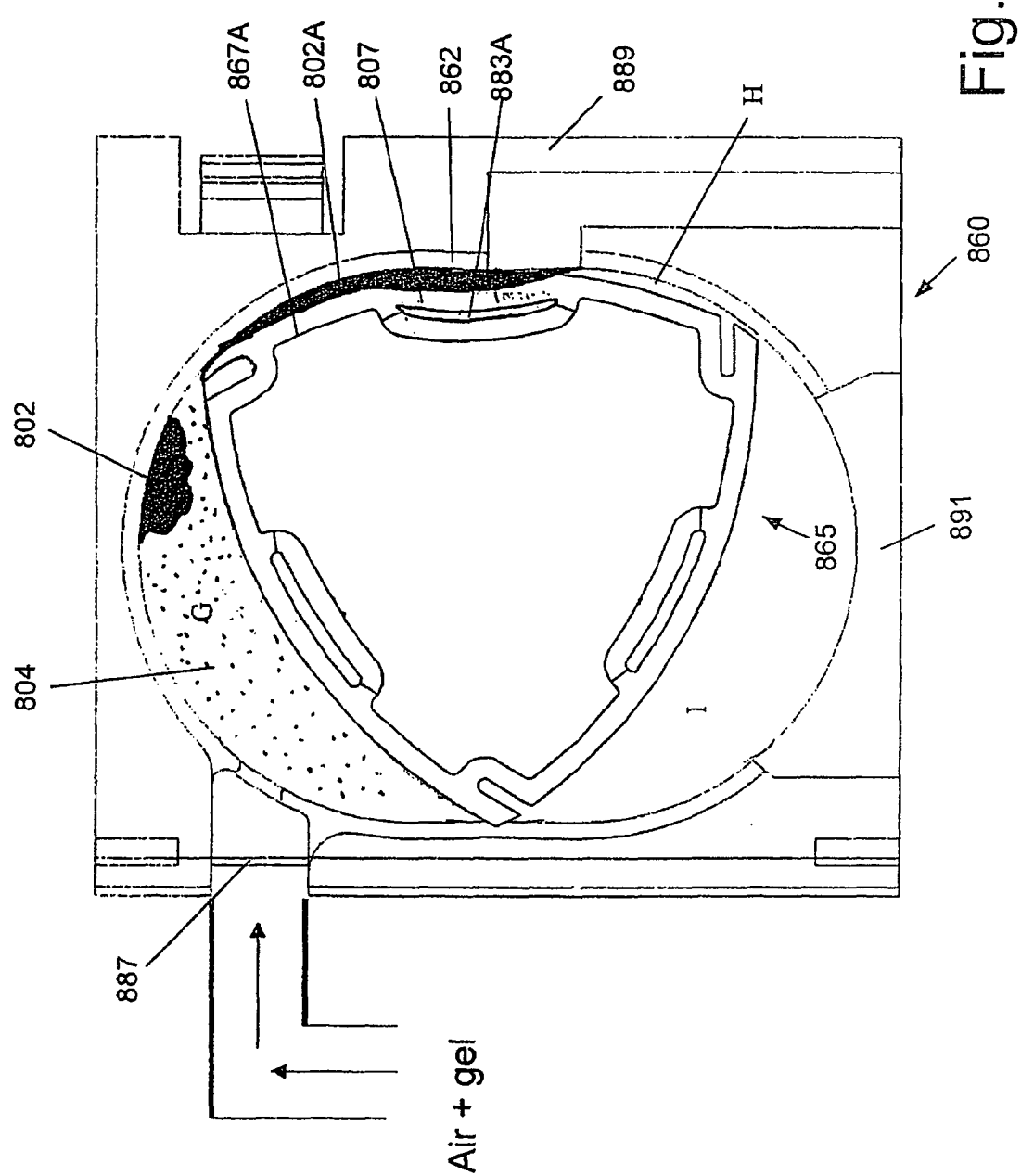

As described hereinabove, the pump is capable of evacuating gel from the vacuum chamber. FIGS. 32a and 32b schematically illustrate the elastic deformation of rotor 865 as gel is transferred within pump 860 from an intake-expansion cycle to a compression-exhaust cycle. The orientation of rotor 865 in FIG. 32a with respect to casing 861 is similar to that of FIG. 31. Upon completion of the intake-expansion cycle, gel 802 and expanded air 804 are retained in compartment H. After additional rotation of rotor 865, compartment G undergoes an intake-expansion cycle after corresponding compartments G1 and G2 completed a transfer cycle and compartment H undergoes a compression-exhaust cycle.

During the compression-exhaust cycle, the volume of compartment H is sufficiently reduced so as to compress the expanded air 804 (not shown). Due to the considerably reduced volume of compartment H, gel 802A is squeezed between inner wall 862 of casing 861 and face 867A of rotor 865, and therefore becomes pressurized by the opposed force applied thereto by inner wall 862 and face 867A to a very high pressure on the order of 10 atmospheres. Central face slot 883A affords face 867A with sufficient flexibility to prevent the degree of gel pressurization within compartment H during the compression-exhaust cycle. Portion 807 of face 867A in the vicinity of central face slot 883A is consequently inwardly flexed in reaction to the force applied by gel 802A. Since the degree of gel pressurization is limited, the pump cover remains in abutment with casing 861, preventing atmospheric-pressure air to infiltrate to the interior of the pump when generating a vacuum. Furthermore, elastically deformable rotor faces minimize wear of the polymer inner walls 862 of casing 861.

The compressed air and pressurized gel are discharged into exhaust tube 889. Upon further rotation of rotor 865, the pressure of the air and gel not discharged through exhaust tube 889, e.g. when a relatively large amount of gel is drawn to the pump cavity, is reduced. The remaining gel is discharged through exhaust pipe 891, while only a small percentage of the remaining air is not discharged through exhaust pipe 891, but rather is transferred towards inlet 887 during the transfer cycle.

Pump 860 may advantageously restore the pressure within the vacuum chamber to atmospheric pressure within less than 0.1 second, in order to allow the raising and subsequent repositioning of the treatment handpiece. Such a quick pressure restoration is made possible by reversing the rotational direction of rotor 865. The rotational direction of rotor 865 may be reversed by changing the polarity of the pump motor. When an electronic controller controls both the light source and the pump motor, the polarity of the pump motor may be automatically reversed following the transmission of a suitable command by an optical detector, which is adapted to detect the cessation of an optical treatment pulse.

A reversal in the rotational direction of rotor 865 allows atmospheric-pressure air to be delivered from compartment I, when the orientation of rotor is as shown in FIG. 31, to conduit 813 and then to the vacuum chamber. Subatmospheric pressure is not generated within the pump cavity even though the volume of a pump compartment is significantly increased upon rotation of rotor 865 since atmospheric-pressure air is also introduced to the pump cavity from exhaust tube 889 and exhaust pipe 891. It will be appreciated that the presence of gel in conduit 813 does not limit the rate of vacuum release since pump 860 can generate a sufficient air pressure to overcome the resistance of the gel, so that air may be reintroduced into the vacuum chamber.

As explained hereinabove, pump 860 may be made from inexpensive Acetal mixed with Teflon, and therefore may be disposable. If so desired, pump 860 may be produced from the same types of steel used for Wankel engines.

Figure 33:
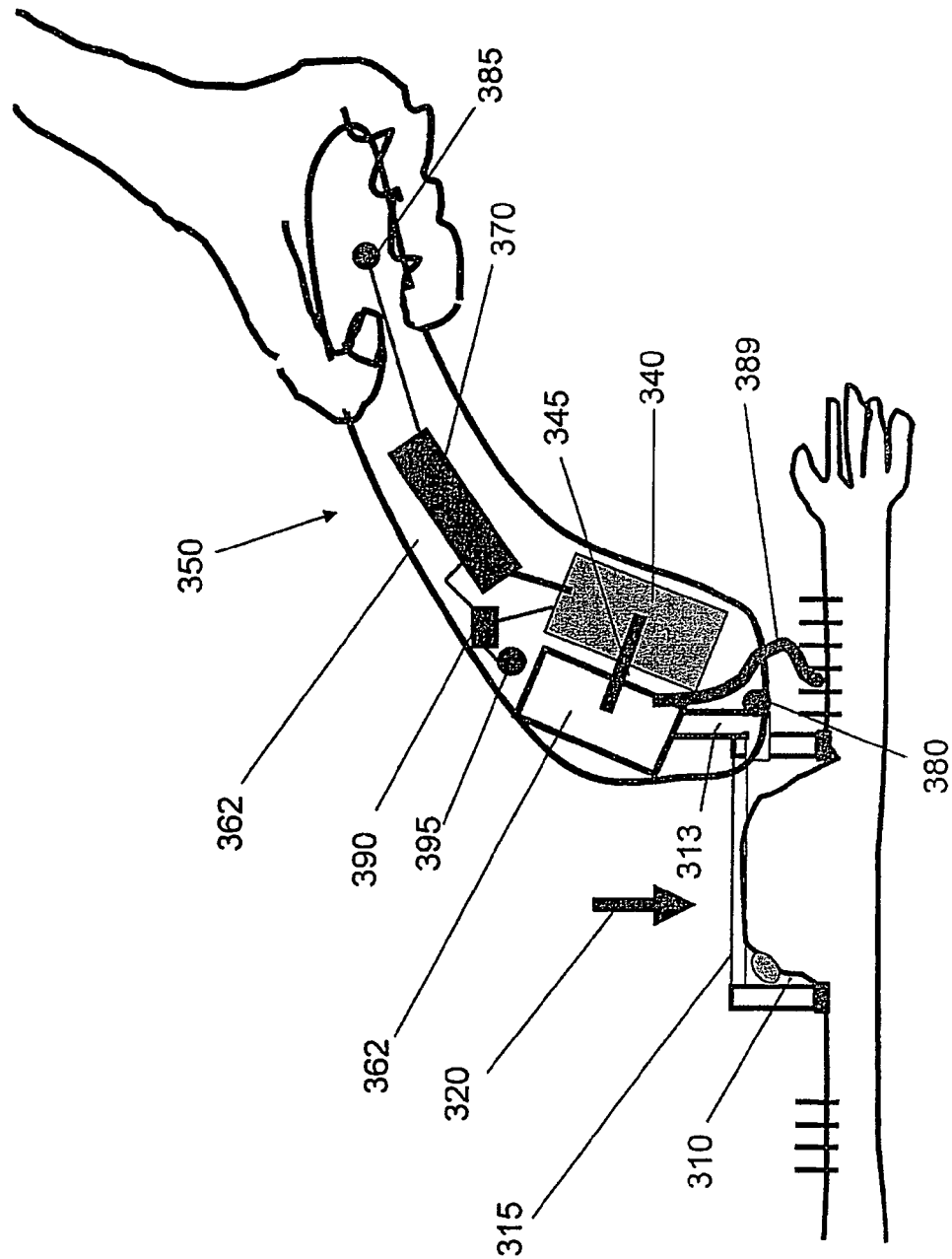
FIG. 33 schematically illustrates a dermatological handpiece system according to one embodiment of the invention.

FIG. 33 schematically illustrates a dermatological handpiece system designated generally by 350 which facilitates reliable and speedy light-based vacuum-assisted treatments in conjunction with gel coated skin. Handpiece system 350 comprises vacuum chamber 310 and handpiece body 362, which is attached to vacuum chamber 310 by attachment means 380 such as a set of screws for fixed attachment or a pivotable attachment means. Handpiece body 362 houses disposable Wankel type vacuum pump 360, as described hereinabove, small brushless motor 340 which drives pump 360 by means of shaft 345, control unit 390 for controlling the motor direction and speed, and battery 370, which powers motor 340 and control unit 390. Pump 360 is in communication via conduit 313 with vacuum chamber 310 having a transmitting element 315 through which IPL or laser light 320 propagates to a skin target. Exhaust tube 389 leads from pump 360 to a skin area to indicate which skin area has undergone a light-based vacuum-assisted treatment.

A handpiece body 362 has a sufficiently small size, low weight and ergonometric design so as to prevent operator fatigue. For example, handpiece body 362 may have a weight of 0.5 kg, a length of 8 cm, a width of 5 cm, and a height of 10-20 cm. Handpiece body 362 is intermittently held by one hand of an operator for more than one hour during repeated repositioning thereof to different skin areas, during vacuum-assisted dermatological treatments of the back or legs. A small handpiece body size also reduces the length of conduit 313 and exhaust tube 389.

The illustrated vacuum chamber 310 is a stand-alone device which is separate from the IPL or laser light source. With such an arrangement, handpiece body 362 is held by one hand and the IPL or laser handpiece is held by the other hand. Motor 340 may be activated by depressing operating button 385 in electrical connection with battery 370, which is positioned in the upper portion of handpiece body 362 and is accessible to a finger of the operator. The rotational direction of motor 340 and consequently of the pump rotor may be reversed e.g. by quickly depressing button 385 twice. The motor may be deactivated by depressing button 385 in a different sequence. Alternatively, pump 360 may be automatically activated by means of sensor 395 in communication with control unit 390, e.g. a skin contact detector, which is adapted to detect the placement of vacuum chamber 310 on a selected skin area. When sensor 395 in communication with control unit 390 is an optical sensor adapted to detect the termination of a light-based treatment pulse, the rotational direction of motor 340 and of the pump rotor may be automatically reversed by means of control unit 390 in order to restore the air pressure within vacuum chamber 310 to atmospheric pressure.

The handpiece system may be embodied such that a single handpiece (not shown) including both the light source and the vacuum pump is used. In this embodiment, the control unit is adapted to control the operation of both the vacuum pump and of the light source. Consequently the control unit can synchronize in sequence a vacuum generating step, a treatment firing step, and a vacuum release step for each treatment cycle. The control unit is therefore suitable for synchronizing a predetermined delay ranging from approximately 0.5 sec to approximately 4 seconds between the activation of the vacuum pump and the firing of the source, in order to ensure that a skin area will be in contact with the transmitting element of the vacuum chamber for a sufficiently long nerve inhibiting duration after the light source is fired. The control unit is also suitable for increasing the pressure in the vacuum chamber to atmospheric pressure by reversing the polarity of the motor following deactivation of the light source.

In another embodiment of the invention, the evacuation of the vacuum chamber may be achieved by means of a peristaltic pump.

Figure 34:
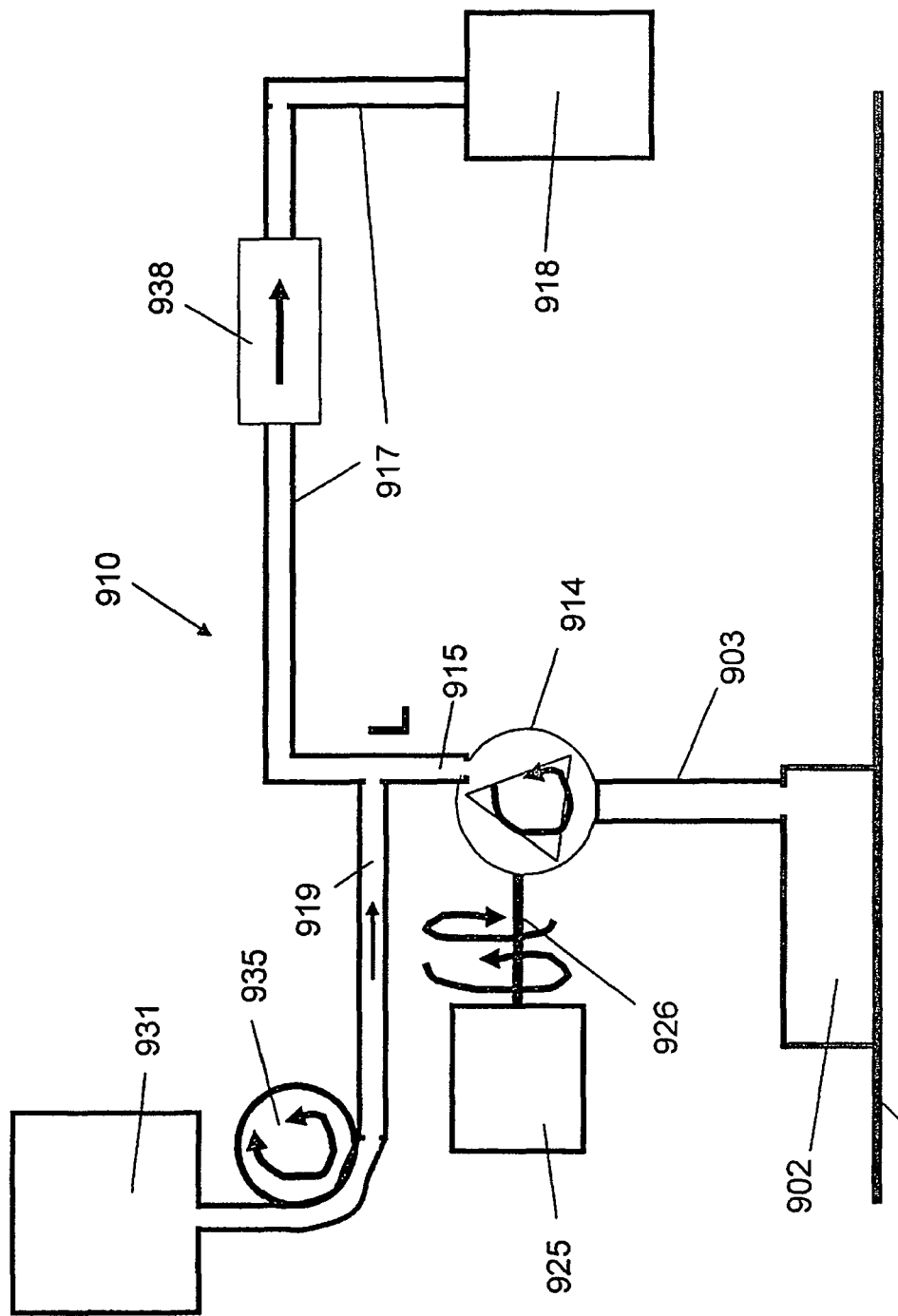
FIG. 34 schematically illustrates apparatus which comprises a pain inhibiting dermatological air-gel vacuum pump and a dissolving solution pump, for providing a repetitive gel cleaning and dissolving capability.

FIG. 34 illustrates apparatus 910 comprising a pain inhibiting dermatological air-gel vacuum pump 914 and a peristaltic pump 935 in fluid communication with dermatological pump 914 has a repetitive gel cleaning and dissolving capability.

As shown, the suction end of Wankel type dermatological air-gel pump 914, or any other suitable rotary or diaphragm pump with similar capabilities, which has a high instantaneous throughput of approximately 5 cm$^3$/0.1 sec, is in communication with vacuum chamber 902 positioned on skin surface 906 via conduit 903. Shaft 926 of dermatological pump 914 is driven by motor 925, which may be an inexpensive reversible direct current (DC) motor. A DC motor can be instantly reversed by reversing its polarity. The vacuum level generated by pump 914 is variable, and is a function of the rotational speed of the rotor of motor 925, which in turn depends on the DC voltage applied thereto. Conduit 903 may be of a short length, e.g. 20 mm if pump 914 is housed within a treatment handpiece, or may be longer, e.g. 3 m if pump 914 is housed within a remote control box, distant from the handpiece, and may be made from Tygon. The discharge end of pump 914 is connected to tube 915, which branches at junction L into hoses 917 and 919. Hose 917 terminates at gel accumulating reservoir 918 and hose 919 terminates at dissolving solution reservoir 931.

In a vacuum applying and pain inhibiting mode, dermatological pump 914 evacuates air and gel from vacuum chamber 902. Gel is discharged through tube 917 and is collected in reservoir 918. Tube 917 is relatively long, e.g. 3 m. Although the gel has excellent lubrication properties and is therefore able to lubricate dermatological pump 914, it tends to dry quickly and to become solid and sticky.

To allow the gel to be reused, a dissolving solution reservoir 931 is provided, which is filled with a cleaning and gel dissolving solution, such as NaCl at a concentration of 2-4%. Peristaltic pump 935 having a relatively low throughput of approximately 200 cm$^3$/10 min is adapted to deliver the dissolving solution from reservoir 931 through hose 919, which is sequentially squeezed by pressing elements of peristaltic pump 935. The dissolving solution is able to flow through hose 917 to gel accumulating reservoir 918 and through tube 915 to dermatological pump 914 and conduit 903. Hose 919 is provided with a check valve (not shown) in the vicinity of junction L, to prevent the flow of gel to reservoir 931. Junction L is typically spaced 2 cm from dermatological pump 914.

The delivery of the dissolving solution to reservoir 918 may be supplemented by means of liquid pump 938 having a relatively low throughput of approximately 200 cm$^3$/10 min, which is installed within an intermediate portion of hose 917 between junction L and reservoir 918. Pump 938, which may be constantly working or in operation for a relatively long period of e.g. 10 minutes, also prevents the backflow of gel from reservoir 918 to dermatological pump 914 during the vacuum release mode.

Dermatological pump 914 may be housed within a handpiece, to increase the mobility of a health professional during a skin treatment, while gel accumulating reservoir 918, dissolving solution reservoir 931, peristaltic pump 935, and liquid pump 938 may be disposed within a remote control box (not shown).

The operation of apparatus 910 is as follows:

A) Once vacuum chamber 902 has been placed on skin surface 906, a suitable skin contact detector generates a signal to enable operation of dermatological pump 914.

B) Dermatological pump 914 is operated in the vacuum applying mode for a very short period of approximately 0.1 seconds, during which air is evacuated from vacuum chamber 902 and a small volume of gel is drawn from above skin surface 906 through tube 903. The drawn gel is delivered through pump 938 to gel accumulating reservoir 918.

C) Once the vacuum level within vacuum chamber 902 has reached a pain inhibiting level and the drawn skin is flattened, the treatment light is fired.

D) Following termination of the treatment pulse, the rotational direction of dermatological pump 914 is reversed and pump 914 is operated in the vacuum release mode for a short period of approximately 0.1 seconds, to allow the handpiece to be repositioned to another skin target.

E) Peristaltic pump 935 is periodically commanded by a control unit (not shown) to commence a gel cleaning and dissolving operation, such as after 100 vacuum applying cycles of pump 914. The frequency of operation for peristaltic pump 935 is dependent upon the viscosity of the gel being utilized. The dissolving solution is delivered by peristaltic pump 935 to junction L and is drawn therefrom by pump 938 to reservoir 918. During the cleaning operation, by which gel in hose 917 and reservoir 918 is dissolved, dermatological pump 914 may continue its operation without having to disrupt the rate of skin treatments.

F) Gel in dermatological pump 914 and in vacuum chamber 902 is cleaned at the end of each treatment session. Vacuum chamber 902 is placed in a small liquid container (not shown), whereupon dermatological pump 914 is operated in a reverse rotational direction so that the dissolving solution may be drawn through tubes 915 and 903 from reservoir 931 while peristaltic pump 935 is also in operation.

There is usually no need to initiate a gel cleaning and dissolving operation after each vacuum applying and treatment cycle.

It will be appreciated that in addition to the Wankel type, other types of air-gel vacuum pumps may be used as well, such as other types of rotary pumps and diaphragm pumps.

Skin Gliding Apparatus

Some light-based hair removal devices operate at high repetition rates which enable fast treatment by gliding the device over the skin. An example of such a device is the Light Sheer diode laser manufactured by Lumenis which can operate at a repetition rate of 2 pulses per sec. The size of the laser exit beam is approximately 10×10 mm. The laser is highly efficient at 40 J/cm$^2$; however, it is very painful, attaining a pain level of 5.

In a preferred embodiment of the invention, a vacuum chamber is provided with skin gliding apparatus. Very fast and painless treatments may be performed by gliding the laser unit distal end over a sapphire transmitting element at a speed ranging from 0.3-40 cm/sec. A gliding action is made possible by means of a suitable track formed in, or attached to, the transmitting element. The track supports the laser unit distal end, and is adapted to minimize friction between the laser distal end and the transmitting element, and to prevent the latter from being scratched. The skin gliding apparatus is preferably configured in such a way so as to maintain the laser unit distal end in a disposition which is substantially perpendicular with respect to the transmitting element and to prevent overlaps or voids between adjacent spots that are treated by the treatment light. Pain is absent due to the relatively large size of the transmitting element, which ensures that a sufficiently large number of pressure receptors are squeezed so that a signal transmitted therefrom inhibits reception of a pain signal, and due to the relatively high vacuum level. In contrast to prior art treatments wherein immediate sharp pain is felt during each treatment pulse, necessitating a patient to rest during a long delay before continuing the treatment or to be applied with a risky analgesic topical cream, the treatment speed of apparatus of the present invention employing a vacuum chamber need not be slowed.

For example, a vacuum chamber having a size of e.g. 20×40 mm is suitable for inhibiting pain in conjunction with treatment light generated by the Light Sheer diode laser having an energy density of 40 J/cm$^2$. The laser unit distal end may be displaced over a sapphire transmitting element at a speed of 10 mm every 0.5 seconds. The applied vacuum is maintained for a duration of 4 seconds, thereby allowing a skin surface having a similar area of 20×40 mm to be treated by the treatment light without having to release the vacuum.

Figure 36:
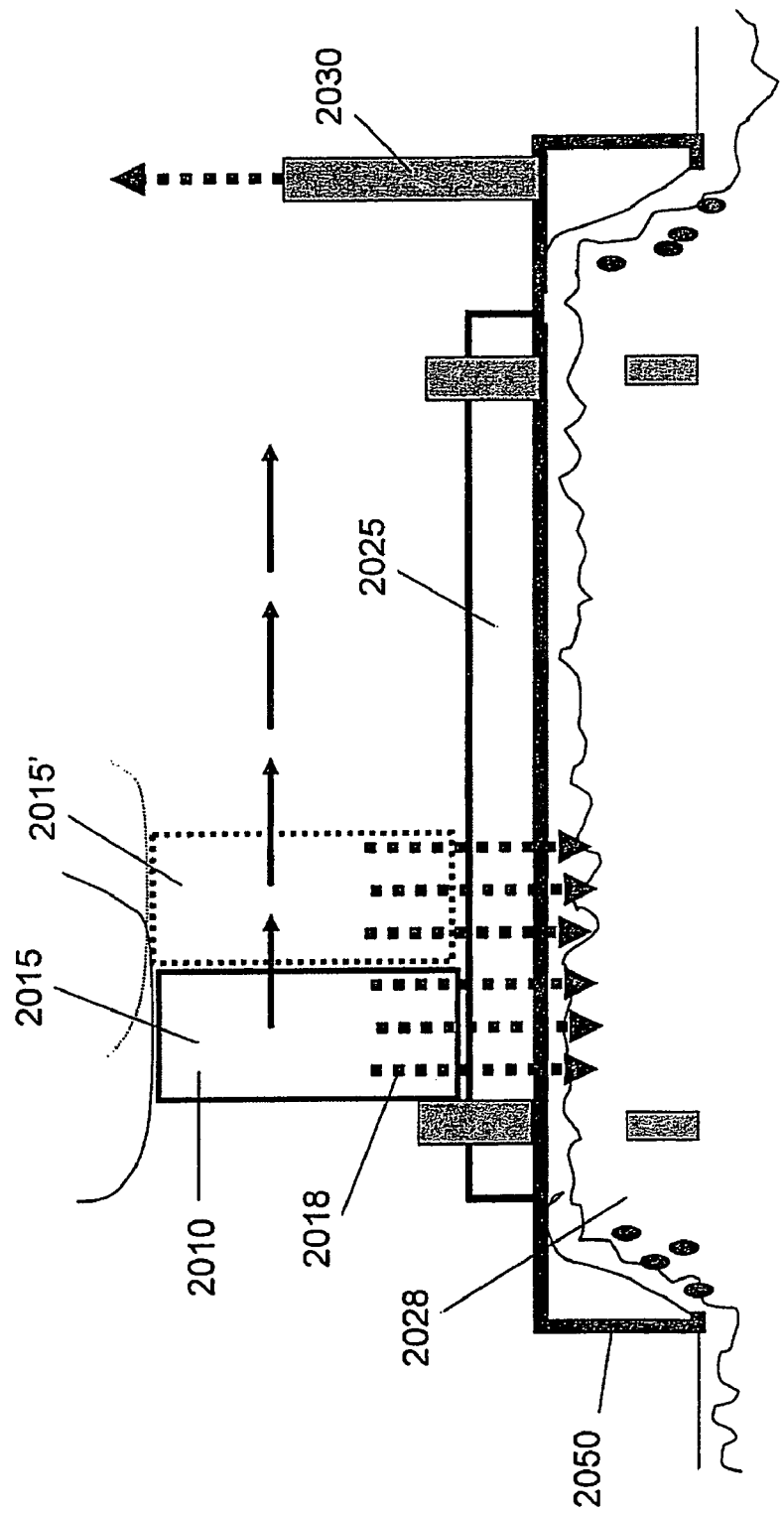
FIG. 36 schematically illustrates another embodiment of the invention wherein gliding apparatus is used to displace a laser or IPL distal end along a large sized transmitting element of a pain inhibiting vacuum chamber.

FIG. 36 schematically illustrates the gliding of a laser distal end on the transmitting element of a vacuum chamber with respect to the following steps:

A) Laser distal end 2010 is initially positioned in contact with the top of transmitting element 2025 of vacuum chamber 2050 at position 2015.
B) Air is evacuated from vacuum chamber 2050 via conduit 2030 within 0.5 sec at a vacuum level of at least 500 mmHg which is suitable for inducing pain inhibition.
C) Treatment laser pulse 2018 is fired at position 2015 towards skin target 2028 therebelow.
D) Laser distal end 2010 is displaced to position 2015' at a speed of L/t, where L is the beam diameter and t is the interval between laser pulses. The laser distal end may be automatically and cyclically repositioned if the gliding track is provided with equally spaced stations, whereat the laser distal end is urged to be stationary when light is emitted therefrom.
E) Treatment laser pulse 2018 is fired at position 2015' towards the skin target therebelow.
F) Steps D) and E) are repeated until laser distal end 2010 is displaced along the entire surface area of transmitting element 2025.
G) Laser distal end 2010 is displaced to original position 2015.
H) The vacuum within vacuum chamber 2050 is released within 0.5 second.
I) Vacuum chamber 2050 is raised and repositioned.

The displacement of laser distal end 2010 may be externally triggered, i.e. by means of an optical detector that senses the presence of a marker on transmitting element 2025 that corresponds to each target position. Alternatively, laser distal end 2010 is driven by a suitable mechanism at a constant speed of L/t over transmitting element 2025 in free running fashion, i.e. not externally triggered. For example, a laser distal end that produces a 12-mm diameter light beam, such as the Light Sheer of Lumenis, will be driven at a speed of 20 mm/sec if the laser is operated in a free running mode at a 2 Hz repetition rate. In the free running mode, a photodiode may be employed, which is adapted to detect a light pulse generated by the laser and to generate an audible signal being indicative that the laser distal end may be repositioned.

FIGS. 41a and 41b illustrate top and side views, respectively, of a transmitting element of a vacuum chamber which is provided with another configuration of bipolar RF-assisted metallic conducting electrodes suitable for skin flattening and pain inhibition in conjunction with laser or IPL treatment light. Sapphire transmitting element 950 is formed with a plurality of slits which are filled with a metallic material such as aluminum, to produce electrodes 951. The dimensions of the slits may be for example a length of 17 mm, a width of 2 mm, and a spacing between two adjacent slits of 30 mm. Electrodes 951 are formed such that the uppermost portion 953 thereof is concave and the lowermost portion 957 thereof in contact with drawn, flattened skin is convex. The concave shape of uppermost portion 953 facilitates the seating therein of RF electrodes 956 provided at the distal end of an IPL or laser unit 955, such as one manufactured by Syneron Medical Ltd., Israel, which generates light 954 transmitted through transmitting element 950. The convex shape of lowermost portion 957 provides good contact with the skin.

By employing such a configuration of electrodes 951, the RF-assisted IPL or laser unit 955 can be glided upon transmitting element 950 at a high speed of V, e.g. capable of moving a distance of 30 mm within 10 millisec. Convex electrodes 956 of IPL or laser unit 955 will therefore be quickly seated into the corresponding concave portions 953 of electrodes 951 above a selected skin target prior to be treated by light 954.

Figure 37A:
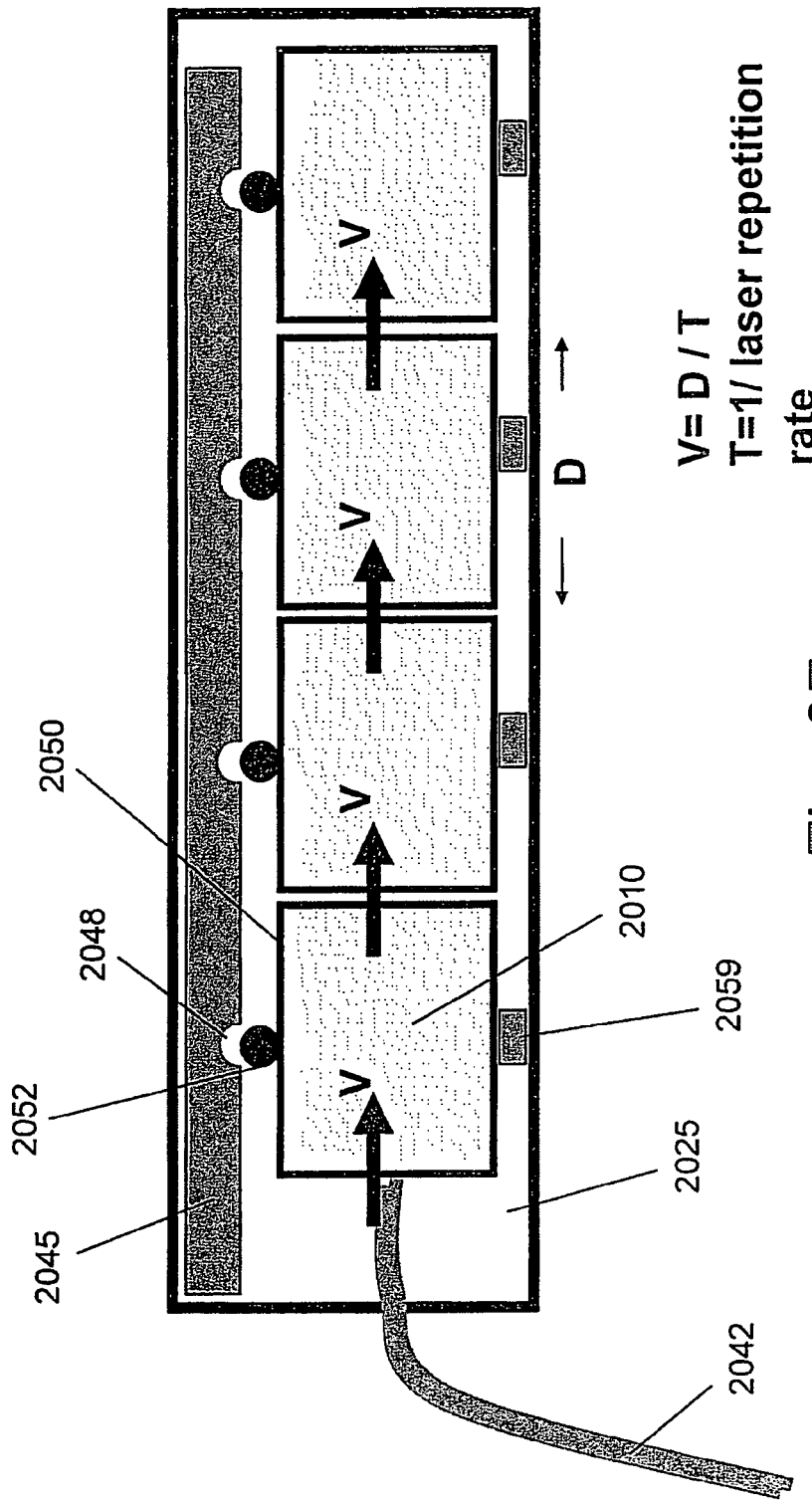
FIGS. 37a and 37b schematically illustrate two embodiments of a gliding apparatus, respectively.
Figure 37B:
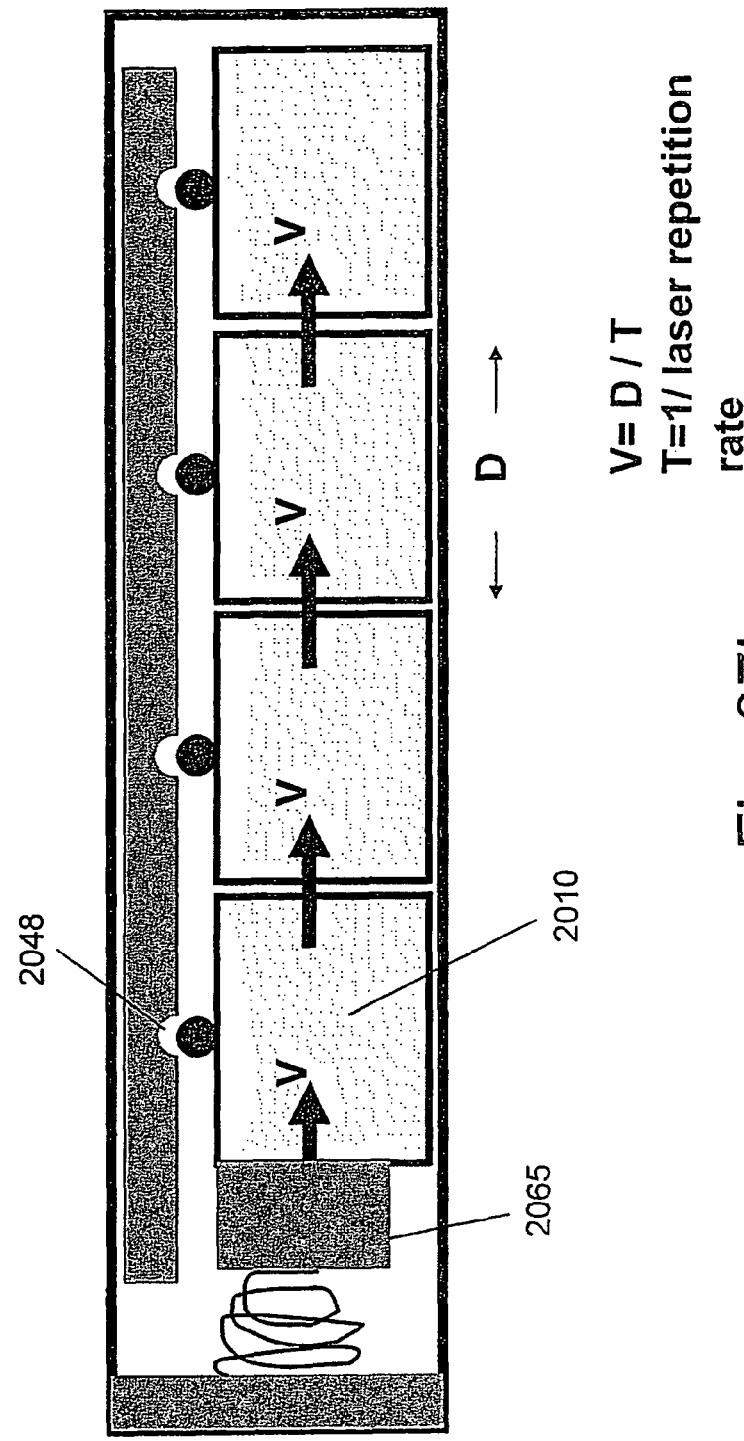

FIGS. 37a and 37b schematically illustrate two driving means, respectively, for gliding a laser distal end 2010 having a size D over the top surface of transmitting element 2025 of a pain inhibiting vacuum chamber.

In FIG. 37a, the driving means is a pneumatic tube 2042 which displaces laser distal end 2010 at a constant speed, or is manual force. A linear ruler 2045 for measuring the displacement of distal end 2025, in which equally spaced apertures 2048 are bored, is attached to transmitting element 2025. Laser distal end 2010 has a frame 2050, to which a spring biased spherical element 2052 for enabling laser distal end 2010 to be linearly displaced along the ruler is attached. Spring 2059 urges spherical element 2052 into a corresponding aperture 2048 whenever a spherical element 2052 is in front of the corresponding aperture 2048. By quickly driving laser distal end 2010, the latter is displaced from aperture to aperture by discrete steps, so that a treatment pulse may be fired at each subsequent step. If laser distal end 2010 is displaced by manual force, the force for disengaging spherical element 2052 from the aperture 2048 in which it is seated can be controlled by selecting the strength of spring 2059. Spring strength is selected to enable disengagement of spherical element 2052 from a corresponding aperture 2048 within a time duration T inversely proportional to the laser repetition rate. As a result, laser distal end 2010 is synchronously displaced with respect to the free running laser repetition rate at a speed of V which is equal to D/T, so that the skin surface under the vacuum chamber may be uniformly treated. A photodiode (not shown) may be employed to detect a laser or IPL pulse and to generate an audible signal, thereby enabling the synchronization of the laser distal end displacement with the laser operation.

In FIG. 37b, the driving means is spring motor 2065, which is provided with a suitable transmission or actuator to linearly displace laser distal end 2010 from one aperture 2048 to another.

Scanning Apparatus

Some lasers for hair removal such as an Nd:YAG laser produced by Sciton Inc., USA or an Alexandrite laser produced by Lumenis employ a scanner to cover large treatment areas within a short time duration. In accordance with the present invention, a scanning laser can scan the area of a skin surface underlying the transmitting element of the vacuum chamber. Scanning is normally fast, and may reach a repetition rate of 5 pulses/sec. By employing a large transmitting element, application of the vacuum may be maintained for a sufficiently long duration to complete a full scan coverage of a treatment area. As an example, a sapphire transmitting element of 20×40 mm can be used. An Nd:YAG laser with a beam diameter of 10×10 mm will have to scan 8 spots to cover a skin area underlying the transmitting element. The scanning can be achieved within 2 seconds at a repetition rate of 4 pulses/sec. Once scanned, the vacuum is released and the process is repeated at the next skin area. Scanners may also be linear scanners which are less expansive and can utilize either a stepper motor or a galvanometric motor such as produced by Cambridge Technology, Inc., USA.

Figure 38:
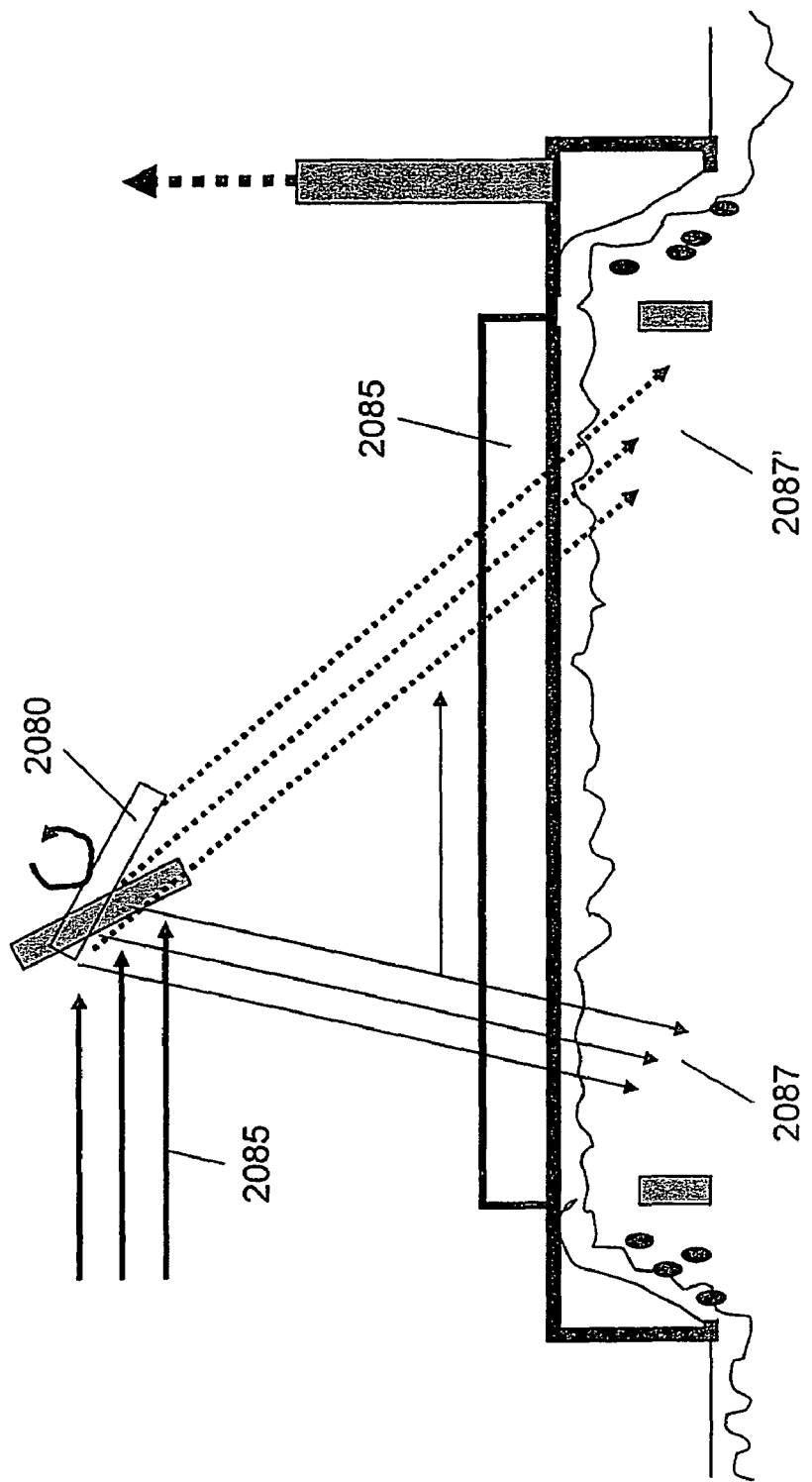
FIG. 38 schematically illustrates a pivotable scanner that is used in conjunction with a large sized pain inhibiting vacuum chamber.

FIG. 38 schematically illustrates a pivotable linear scanner 2080 that can direct a laser beam 2085, such as generated by an Alexandrite laser, to various flattened skin targets 2087 and 2087' underlying transmitting element 2085 of the vacuum chamber. After the entire underlying skin surface is scanned by treatment light 2085, scanner is returned to its original position and the vacuum is released, to allow the vacuum chamber to be repositioned.

Figure 39:
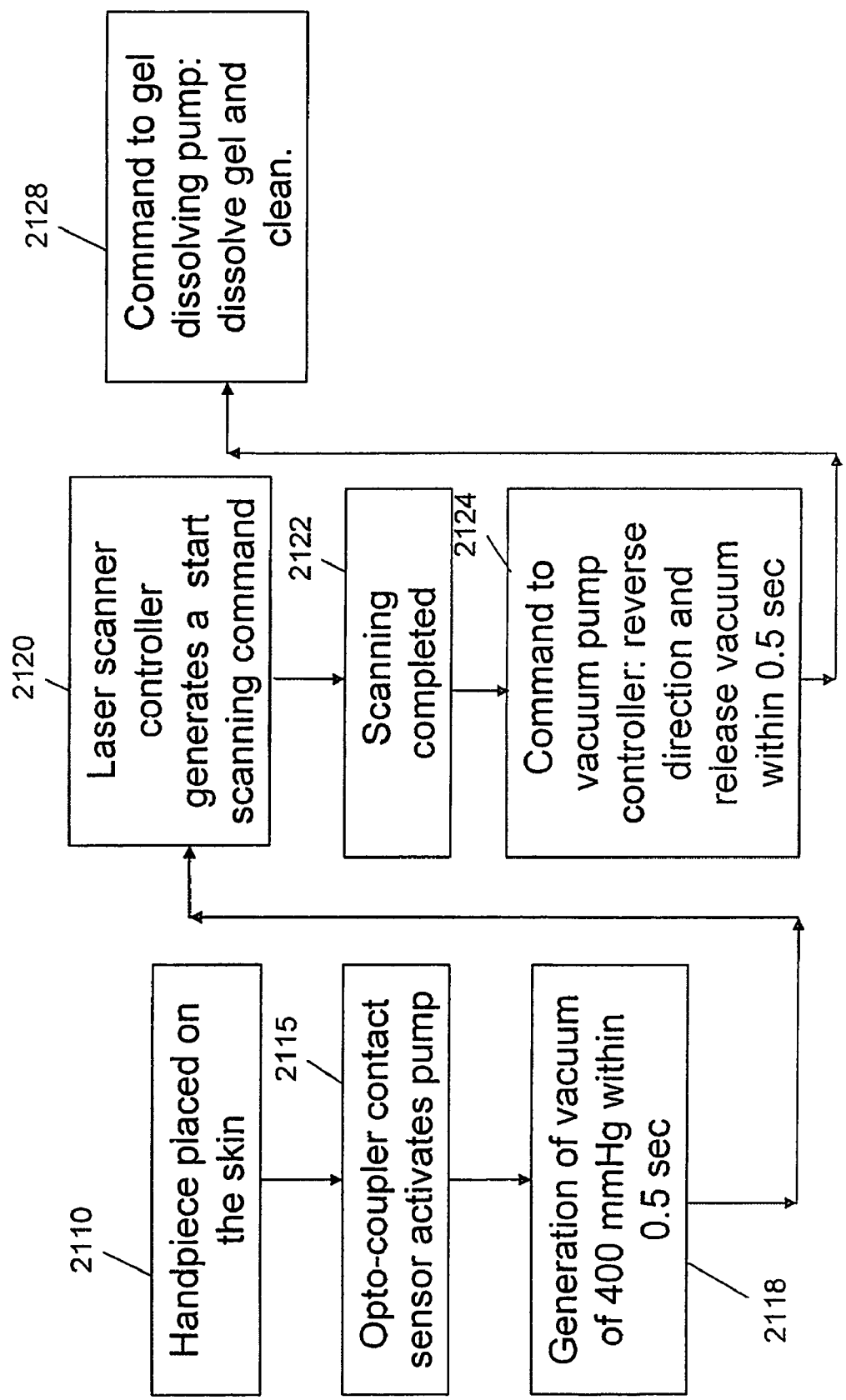
FIG. 39 is a flow chart of a method for synchronizing the operation of a laser beam scanner with respect to that of a pain inhibiting vacuum pump.

FIG. 39 illustrates a typical sequence of commands for treating a skin target with a scanner, in accordance with an embodiment of the present invention. Such a sequence is suitable for hair removal in conjunction with an exemplary light source which is an Alexandrite laser an exemplary scanner which is a linear scanner. In step 2110, a handpiece in which the light source and vacuum chamber are housed is placed on a skin target. In step 2115, an opto-coupler contact sensor senses contact with the skin target and transmits a signal to activate the vacuum pump. In step 2118, a vacuum level of at least 400 mmHg is generated, optionally by means of a pressure sensor, within the vacuum chamber in less than 0.5 seconds. In step 2120, the laser scanner controller initiates a command to commence the scanning of a laser beam in controlled fashion throughout the entire skin surface underlying the transmitting element. After the scanning process is completed in step 2122, optionally as detected by means of an optical sensor, the vacuum pump controller is commanded in step 2124 to reverse the direction of the vacuum pump and to release the vacuum within 0.5 seconds. A gel dissolving pump is then commanded in step 2128 to deliver a dissolving solution in order to dissolve and clean gel.

Figure 40:
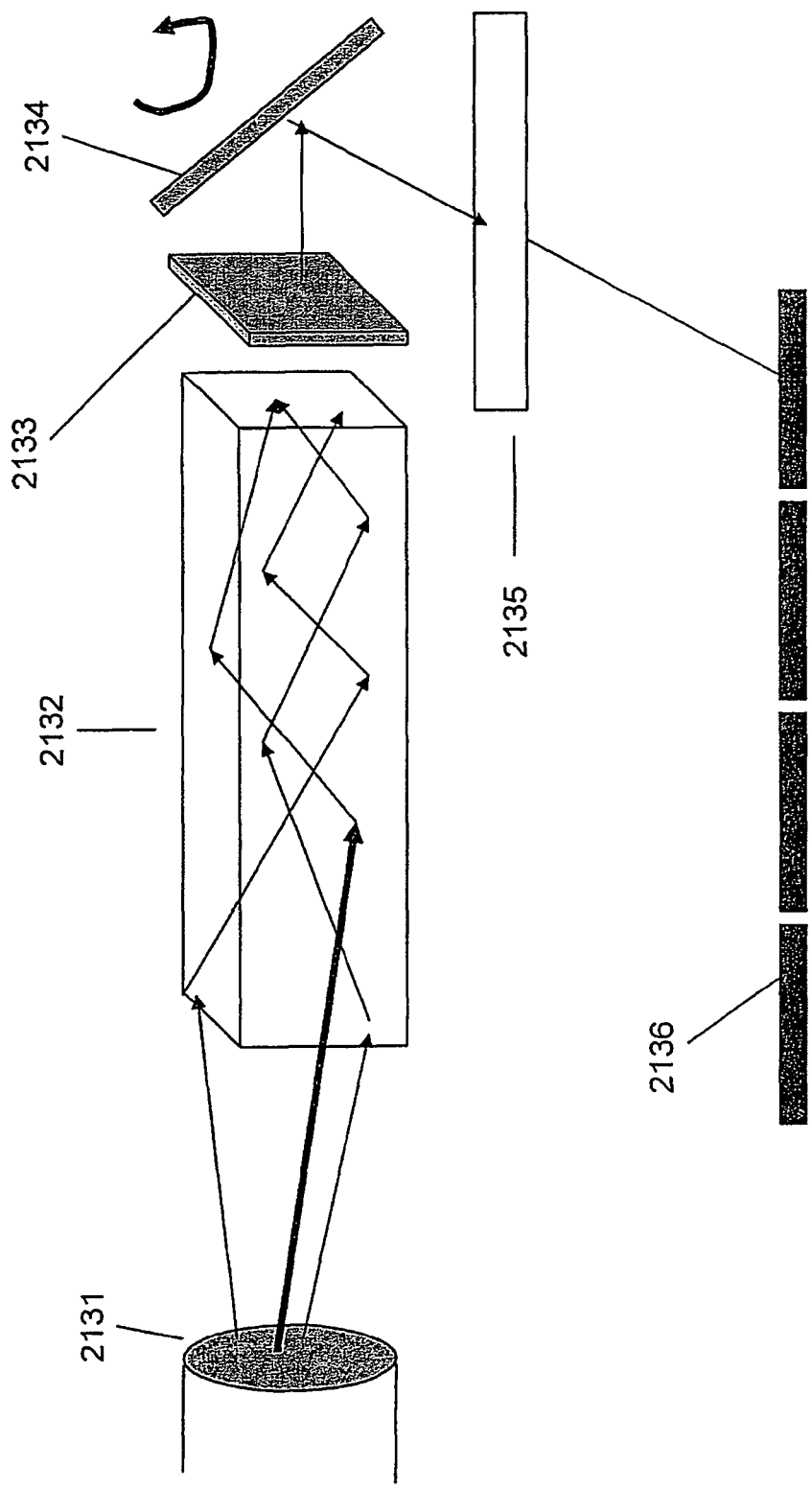
FIG. 40 schematically illustrates a kaleidoscopic square beam homogenizer which enables the homogeneous scanning of a laser beam without overlap on a vacuum chamber transmitting element.

FIG. 40 illustrates another embodiment of the present invention which enables the homogeneous scanning of a laser beam such as produce by a hair removal Alexandrite laser or Nd:YAG laser on the vacuum chamber transmitting element. A distal fiber 2131 having a diameter of e.g. 1 mm produces a round beam. The output beam is fed into a square kaleidoscope 2132 having for example a width of 5 mm and a length of 50 mm. The square beam 2133 exiting kaleidoscope 2132 is imaged on the skin surface and is scanned with a scanning mirror 2134 to produce an array 2136 of square beams on the skin surface. The transformation of a round beam into a square beam enables scanning without any overlap on the vacuum chamber transmitting element. The prevention of scanning beam overlap is particularly important to avoid hyperpigmentation on dark skin.

Figure 44:
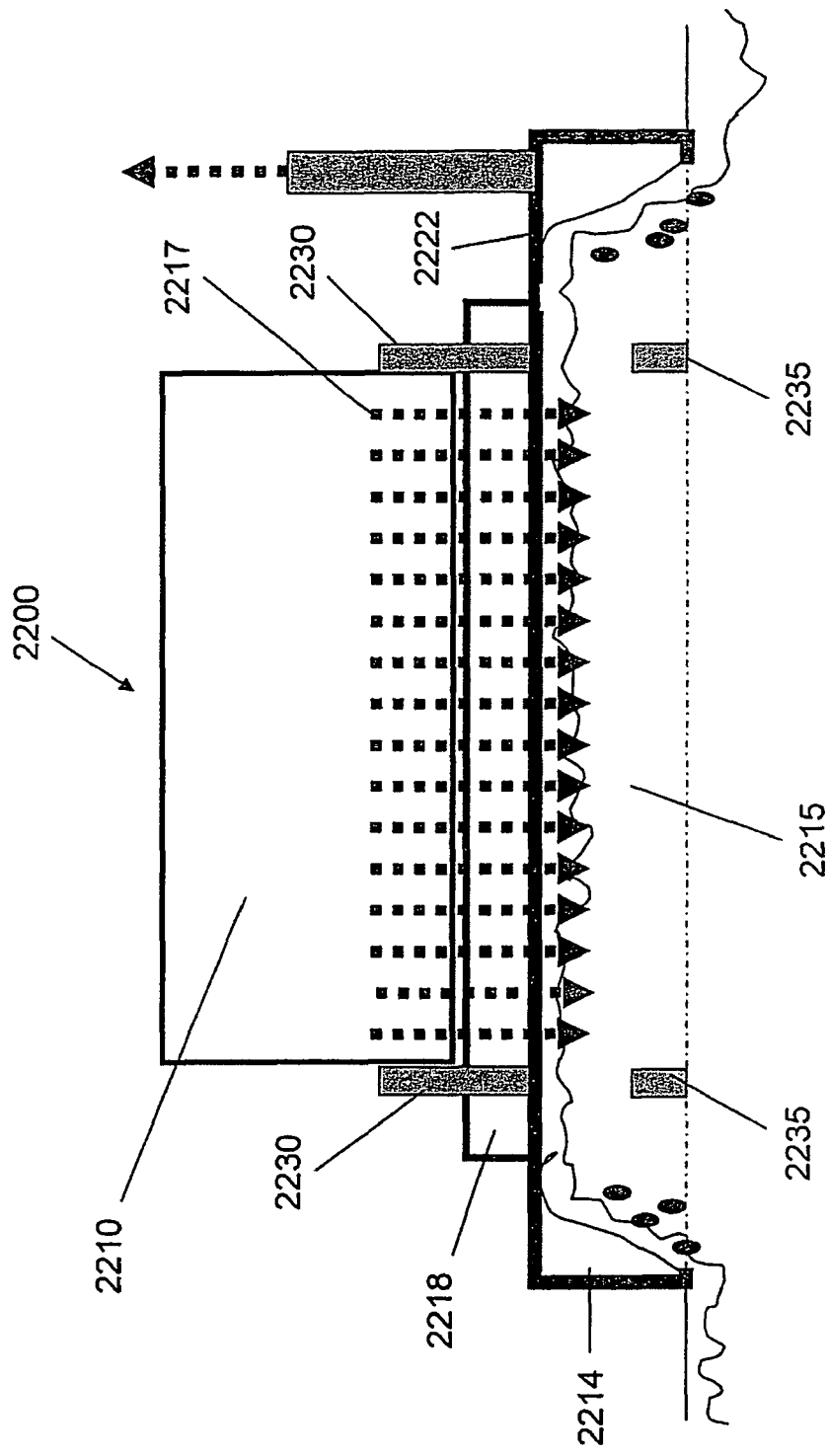
FIG. 44 schematically illustrates means for centering a light source distal end with respect to a vacuum chamber.

FIG. 44 illustrates apparatus 2200 which is provided with means to releasably attach the distal end of an IPL or laser source to the vacuum chamber. The releasably attaching means may be a pair of vertical walls 2230, or any other suitable mechanical elements, attached to cover 2222 of vacuum chamber 2214. Walls 2230, which may have a thickness of 2 mm and a height of 5 mm, also serve to center the distal end 2210 of an IPL source for treating skin target 2215 by treatment beam 2217 generated thereby with respect to the walls of vacuum chamber 2214, above transmitting element 2218. IPL distal end may be quickly placed the two walls 2230. Apparatus 2200 is also provided with two markers 2235 positioned on the side of vacuum chamber 2214. The spacing between the two markers 2235 is substantially equal to the diameter of beam 2217, to enable the accurate repositioning of vacuum chamber 2214 to a subsequent skin target without gaps or overlaps.

Figure 20:
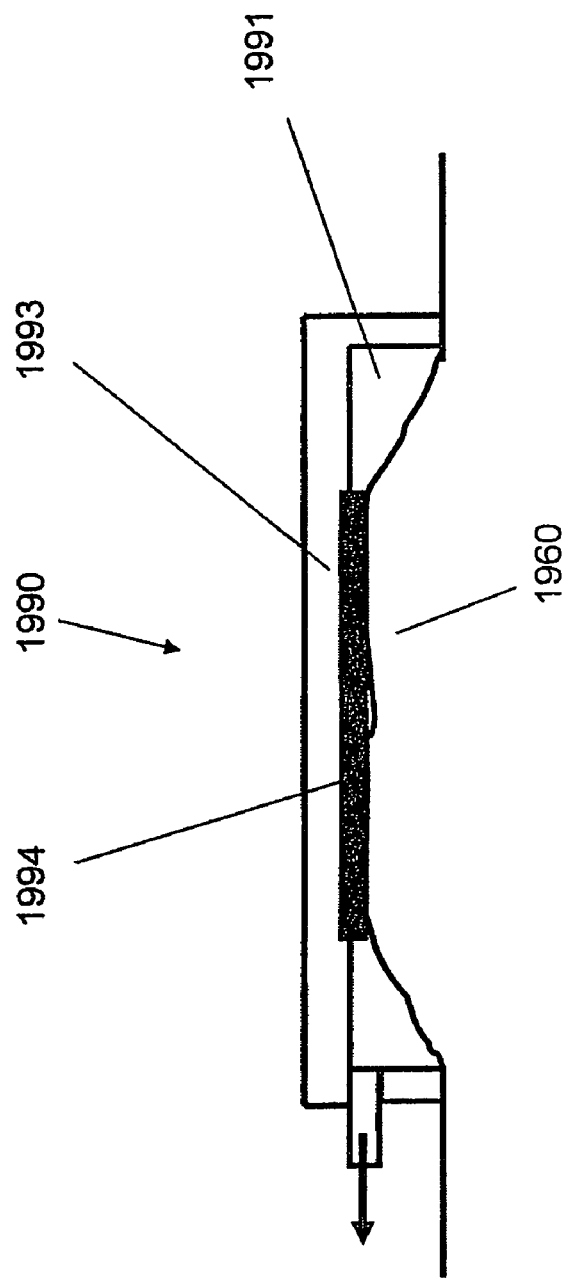
FIG. 20 is a schematic drawing of apparatus in accordance with yet another embodiment of the invention.

In FIG. 20, apparatus 1990 comprises a thin polycarbonate layer 1994, e.g. having a thickness of 10 microns, attached to the distal face of transmitting element 1993 and transparent to the treatment light directed to skin target 1960. Vacuum chamber 1991 is suitably sized and the applied vacuum level is sufficient to draw skin target 1960 to be in pressing contact with polycarbonate layer 1994. Polycarbonate layer 1994 is sufficiently thin to conduct heat from skin target 1960 to transmitting element 1993, is sufficiently soft to provide good mechanical matching between skin target 1960 and transmitting element 1993, and also provides good optical matching therebetween.

As described hereinabove, applying a vacuum to the vacuum chamber may either increase or decrease the blood volume fraction within a skin target, depending on a selected configuration of the vacuum chamber. Accordingly, a health professional may employ two differently configured vacuum chambers, each of which is releasably attachable to the same light source handpiece, in order to effect two distinct types of vacuum-assisted light-based treatment, respectively, with a minimum delay to the patient. Thus a single light source and a single vacuum pump may be used for both treatment of vascular lesions by increasing blood concentration within a skin target and for painless hair removal.

In summation, Table I below tabulates the main differences between prior art vacuum-assisted light-based treatment methods, by which ablated skin and vaporous debris are evacuated from a skin target, and that of the present invention:

TABLE I

|  | Present Invention | Prior Art Smoke Evacuators |
|---|---|---|
| Treatment Depth | Subcutaneous | Skin surface |
| Light source | Non-ablative, 400-1800 nm | Ablative, above 1800 nm |
| High Vacuum Level (approximately 0.5 atm) | Yes | No; evacuated air is replaced by fresh air |
| Automatic Release of Vacuum, to Allow Displacement of Treatment Handpiece | Yes; by means of control unit | Not necessary due to low vacuum level |
| Contact between Skin and Transmitting element | Yes; for pain alleviation | No |
| Suitable for Employment of Gel | Yes | No |
| Vacuum-Assisted Pain Alleviation | Yes | No |
| Enhanced Skin Redness | Yes; when skin is not flattened | No |
| Suitable for Non-Ablative IPL and Nd:YAG, Dye, Alexandrite, Ruby, and Diode Lasers | Yes | No; Suitable for Ablative Laasers |

Figure 26:
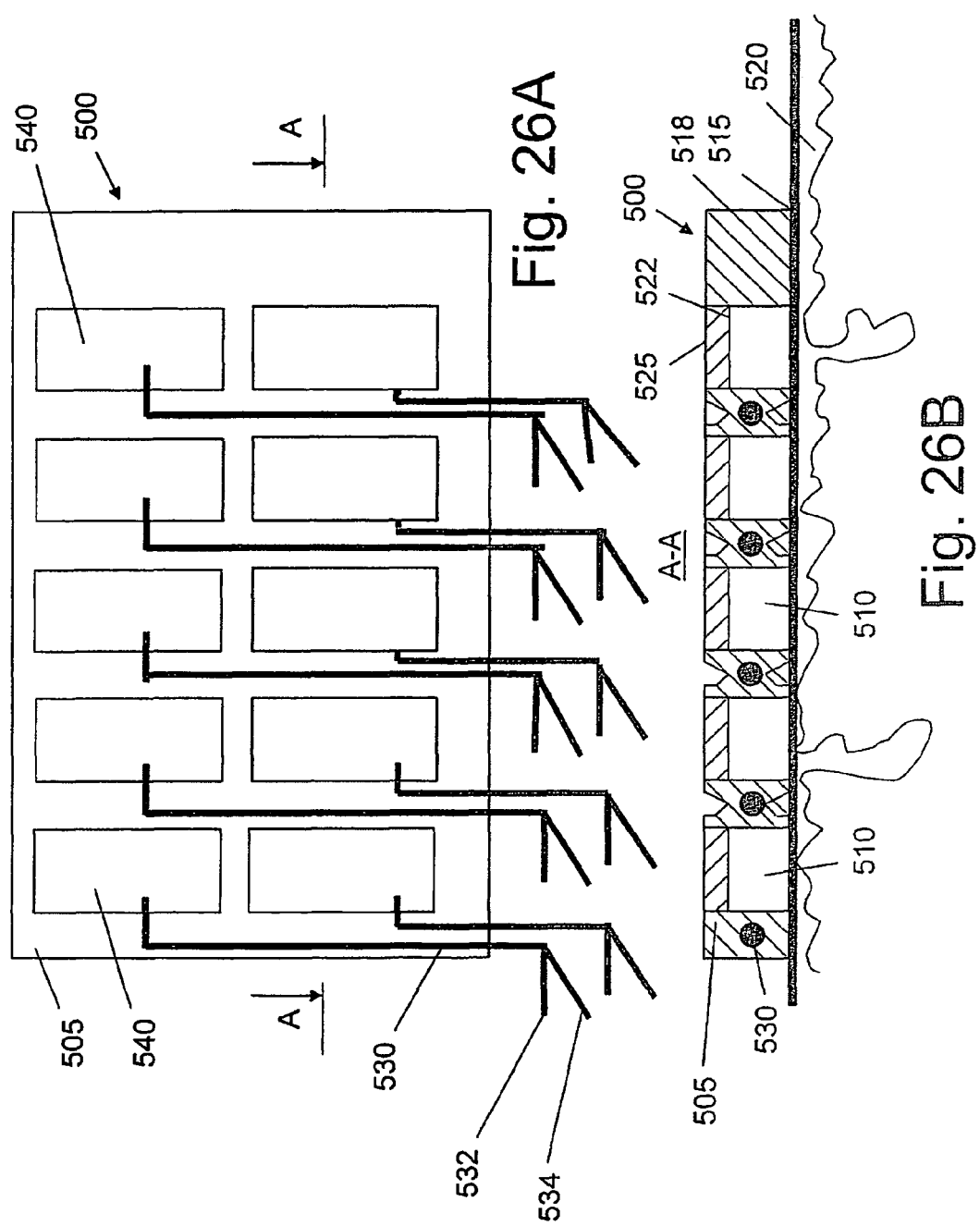
FIG. 26A is a plan view of an array of vacuum chambers and FIG. 26B is a cross sectional view thereof, taken about plane A-A of FIG. 26A.

FIGS. 26A-B illustrate another embodiment of the invention by which a vacuum chamber need not be repositioned from one skin target to another. FIG. 26A is a schematic plan view of the apparatus and FIG. 26B is a cross sectional view thereof. As shown, array 500 of vacuum chambers is embodied by a single flat sheet 505, e.g. disposable and produced from low cost, transparent or translucent molded silicon, which is placed on skin surface 520 and formed with a plurality of vacuum chambers 510. The interior of each vacuum chamber 510 is defined by a bottom which is coplanar with bottom edge 515 of sheet 505, two side walls 522 extending proximally from bottom edge 515, and top edge 522 separated distally from upper surface 525 of sheet 505. A transmitting element 540 corresponding to each vacuum chamber 510 is secured to sheet 505, directly above top edge 522 of the vacuum chamber. Transmitting element 540 may be an inexpensive thin polycarbonate plate or a diffuser. The bulk material of sheet 505 is also formed with a plurality of conduits 530, each of which in communication with a corresponding vacuum chamber 510 and through which air is evacuated from the corresponding vacuum chamber. The distance between adjacent vacuum chambers 510 is sufficiently small to allow light which has diffused from the interior of each chamber to treat a skin area located underneath a corresponding conduit 530. Each conduit 530 branches into portions 532 and 534, wherein all conduit portions 532 are in communication with a vacuum pump (not shown) and all conduit portions 534 are in communication with a source of compressed air (not shown).

Array 500 advantageously allows a large-area skin surface, such as of an arm or leg, to be treated by a light source. The treatment light source is sequentially directed to each vacuum chamber 510. Following propagation of the light through a selected vacuum chamber in order to treat a corresponding skin target, the light source may be quickly moved or glided to another skin target without having to move a vacuum chamber and overcoming the force which urges it to the skin surface. Since a vacuum chamber is not displaced, gel is similarly not moved and does not accumulate. Consequently, there is no need to provide means for preventing obstruction of gel within the vacuum pump.

Array 500 is also provided with at least one contact detector (not shown), which triggers a signal to activate the vacuum pump. When the contact detector senses the placement of array 500 on a skin surface, the vacuum pump is activated, and the air from all vacuum chambers 510 is evacuated simultaneously. The health professional then sequentially directs the light source to each vacuum chamber 510. Following completion of the treatment for the entire skin surface, the light source is deactivated and then the vacuum pump is deactivated. Alternatively, each vacuum chamber is provided with a contact detector, two control valves to control the passage of fluid through conduits portions 532 and 534, respectively, and light detector (all of which are not shown). When a treatment handpiece is placed on a transmitting element 540, the corresponding contact detector transmits a signal to activate the vacuum pump, open the control valve which regulates the fluid passage through the corresponding conduit portion 532, and then activates the light source. Upon completion of the light treatment, the light source is deactivated after a predetermined period of time or is manually deactivated. The light detector transmits a signal to close the control valve which regulates the fluid passage through the corresponding conduit portion 532 and to open the control valve which regulates the fluid passage through the corresponding conduit portion 534, in order to release the vacuum. This cycle is repeated for all vacuum chambers 510.

Vacuum-Assisted Photodynamic Therapy

The aforementioned skin flattening process can be used to improve the treatment of skin lesions with photodynamic therapy (PDT) and light which normally has a shallow penetration depth into the skin, such as blue, green or yellow light. Some lesions, such as acne rich with porphyrins, and malignant and precancerous lesions, such as actinic keratosis, can be treated by applying Levulan ALA produced by DUSA Pharmaceuticals, Inc., USA, which is absorbed by the porphyrins so as to be selectively attracted to fast dividing cells, and by photodynamic treatments. The porphyrins are selectively activated by blue light at e.g. 405 nm, by green light at e.g. 514 nm, and by yellow light at e.g. 585 nm. Melanin and blood in the skin normally do not allow light at these wavelengths to penetrate deep into the skin due to strong absorption. By stretching the skin and expelling blood from the skin which is flattened by the cover of the vacuum chamber, light penetration is enhanced and treatment is improved. An array of light emitting diodes such as produced by Philips Lumileds Lighting Company, USA having a power density of 1-20 milliwatts/cm$^2$ may be used.

In another embodiment, the transmitting element of the vacuum chamber is more separated from the skin surface, to prevent the skin target from being flattened. The applied vacuum causes emptying of the sebacious glands of acne lesions. After the vacuum is applied, blue, green or yellow treatment light may be fired, after which a skin flattening light treatment may be performed.

By employing the aforementioned skin flattening procedure, tattoos may be painlessly removed in conjunction with laser or IPL treatment light. Tattoos are often applied over large areas of the skin, such as on half the circumference of an arm, and a large number of patients are desirous of removing the tattoo after a few years. Also, eyebrow tattoos or lip tattoos fade and generally need to be removed prior to applying a new tattoo. Tattoo removal is most efficiently performed with a Q-switched laser, e.g. having an energy density of 10 J/cm$^2$ and a pulse duration of 10 nsec, with a frequency doubled Nd:YAG laser operating at 532 nm for red tattoos or having an energy density of 10 J/cm$^2$ and a pulse duration of 10 nsec for other colored tattoos, or with a Ruby, Alexandrite, or Nd:YAG laser operating at 694 nm, 755 nm, and 1064 nm, respectively, for blue tattoos, a treatment with which is often very painful when the skin target is not flattened in accordance with the method of the present invention.

Prior art wide-area tattoo removal is generally not tolerable and requires the application of a topical analgesic cream such as EMLA which is risky when applied over larger areas. By firing the tattoo removal treatment light through a transparent transmitting element of a vacuum chamber which flattens the skin at a vacuum level suitable for inhibiting pain transmission from the pain receptors in the skin target, tattoo removal from very large skin areas may be performed without any pain and without any interruptions. With use of a pain inhibiting vacuum chamber, significant pain reduction may be noticeable, such as from a pain level of 4 which is very painful to a pain level of 2 which is not painful.

When red tattoos are removed with green laser or IPL light according to prior art methods, blood vessels present in the skin are thermally damaged since red blood vessels absorb green light. The thermal damage often results in bruises which last a few days. In contrast, the skin target does not become bruised during tattoo removal in accordance with the method of the present invention due to the expulsion of blood vessels from the skin target as a result of the skin flattening process. Tattoo removal may be performed with or without the application of gel to the skin surface.

A light beam suitable for tattoo removal having a typical energy density level of 4-13 J/cm$^2$ generally does not generate an excessive amount of heat in the skin or in the transmitting element which is in contact with the flattened skin. As a result, an inexpensive glass or plastic transmitting element may be used since the use of a sapphire transmitting element having high thermal conductivity is unnecessary. Accordingly, an affordable disposable vacuum chamber for tattoo removal may be employed. Due to the superficial bleeding and the resulting skin contamination associated with tattoo removal, the use of a disposable vacuum chamber is quite beneficial. The size of a vacuum chamber for tattoo removal is selected according to the size of the tattooed area and the bodily location, e.g. an eyebrow may require a thin and elongated vacuum chamber. The typical size of a vacuum chamber ranges between 12×20 mm and 25×60 mm, although other sizes may be selected as well. A typical height of the vacuum chamber ranges between 2-8 mm.

The removal of pigmented lesions is very similar to the removal of tattoos. Tattoo removal laser and IPL units are suitable for the removal of pigmented lesions. An IPL unit is generally employed for the removal of pigmented lesions due to its capability of removing unwanted hair with the same unit. The prior art treatment of pigmented lesions is also painful, and the use of a vacuum chamber for is therefore of great utility. The size of a vacuum chamber for the treatment of pigmented lesions is similar to that for tattoo removal. A vacuum chamber which is excessively small, e.g. 5×5 mm, may not efficiently inhibit pain transmission.

EXAMPLE 1

An experiment was performed to determine the time response of skin erythema following application of a vacuum onto various skin locations. A pipe of 6 mm diameter was sequentially placed on a hand, eye periphery, arm, and forehead at a subatmospheric pressure of approximately 100 millibar. The skin locations were selected based on the suitability for treatment: the hands and eye periphery for wrinkle removal, arm for hair removal, and forehead for port wine stain treatment. The vacuum was applied for the different periods of time of 1/10, 1/2, 1, 2, 3 seconds and then stopped. The erythema level and erythema delay time were then measured.

The response time of the hand and eye periphery was 1/2 sec, the response time of the arm was 1 second and the response time of the forehead was 1/2 second. Accordingly, the experimental results indicate that the necessary delay between the application of the vacuum and firing of the laser or intensed pulsed light is preferably less than 1 second, so as not to delay the total treatment time, since the repetition rate of most laser or intensed pulsed light sources is generally less than 1 pulse/sec.

The erythema delay time was less than 1 second, and therefore the experimental results indicate that patients will not sense appreciable aesthetic discomfort following treatment in accordance with the present invention.

EXAMPLE 2

An intense pulsed light system comprising a broad band Xe flashlamp and a cutoff filter for limiting light transmission between 755 nm and 1200 nm is suitable for aesthetic treatments, such that light delivered through a rectangular light guide is emitted at an energy density of 20 J/cm$^2$ and a pulse duration of 40 milliseconds, for hair removal with respect to a treated area of 15×45 mm.

While efficacy of such a light system for the smoothening of fine wrinkles, i.e. photorejuvenation, is very limited by prior art devices, due to the poor absorption of light by blood vessels at those wavelengths, enhanced light absorption in targeted skin structures in accordance with the present invention would increase the efficacy.

A transparent vacuum chamber of 1 mm height is preferably integrally formed with a handpiece through which intense pulsed light is directed. A diaphragm miniature pump, such as one produced by Richly Tomas which applies a vacuum level of 100 millibar, is in communication with the chamber and a control valve is electronically opened or closed. When the control valve is opened, the pressure in the vacuum chamber is reduced to 100 millibar within less than 10 milliseconds. As a result of the application of vacuum, the skin slightly protrudes into the vacuum chamber at an angle as small as 1/15-1/45 radian (height divided by size of skin target) and a height of 1 mm. Blood is drawn into the drawn skin target, which achieves a much pinker hue and therefore has a higher light absorbence. The increased redness of the skin increases the light absorption by a factor of 3. As a result, the efficacy of the aforementioned light system is similar to that of a prior art system operating at 60 Joules/cm$^2$, which is known to provide adequate results in wrinkle removal procedures. At energy density levels as high as 20 J/cm$^2$, it is preferable to chill the epidermis in order to avoid a risk of a burn. Epidermis chilling is accomplished by means of an aluminum plate, which is chilled by a thermoelectric chiller. The plate is in contact with the skin and chills the skin just before the handpiece is moved to the chilled skin target, prior to treatment.

The invention has thereby converted an intense pulsed light device for hair removal into an efficient photorejuvenation device as well.

EXAMPLE 3

An Nd:YAG laser operating at 1064 nm, 40 milliseconds pulse duration, and energy density of 70 J/cm$^2$ is suitable for prior art hair removal having a spot size of 7 mm. By prior art hair removal, absorption of light in the hair shaft melanin is limited, with a contributory factor in hair removal being attributed to the absorption of light by blood in the hair follicle bulb zone. Since the energy density level of 70 J/cm$^2$ is risky to the epidermis of dark skin, it would be preferable to operate the laser at 40 J/cm$^2$.

A vacuum chamber is preferably integrally formed with a handpiece through which intense pulsed light is directed, at a distance of 1 mm from the skin target. A vacuum is applied to the skin target for 2 seconds. The blood concentration near the follicle bulb and in the bulge at a depth of 4 and 2 mm, respectively, is increased by a factor of 2. As a result the laser is operated with the same efficacy at energy levels closer to 40 J/cm$^2$ and is much safer.

EXAMPLE 4

A Dye laser emitting light at a wavelength of 585 nm, with a spot size of 5 mm and pulse duration of 1 microsecond, is used by prior art methods for treatment of vascular lesions, such as telangectasia, and port wine stains, at an energy density level ranging from 10-15 J/cm$^2$ and for the smoothing of wrinkles at an energy density level of 3-4 J/cm$^2$. Some disadvantages of the prior art method are the purpura that is often produced on the skin during vascular treatments and the very large number of treatments (more than 10) which are necessary for the smoothening of wrinkles.

By applying a controlled vacuum to a vacuum chamber in contact with a skin target, having either a moderate vacuum level of approximately 600 millibar or a vacuum which is modulated at a frequency of 10 Hz for 1 seconds prior to the firing of the laser, the efficacy of the laser is enhanced. Consequently it is possible to treat vascular lesions at 7 J/cm$^2$ without creating a purpura and to remove wrinkles with a much smaller number of treatments (5).

EXAMPLE 5

A prior art diode laser operated at 810 nm or a Dye laser is suitable for treating vascular rich psoriatic skin, wherein the treated area per pulse is approximately 1 cm$^2$. By employing a vacuum chamber attached to the distal end of the handpiece of either of these lasers, blood is drawn to the lesion and treatment efficacy is improved. The vacuum may be applied for 2 seconds prior to firing the laser beam.

EXAMPLE 6

A deep penetrating laser, such as a pulsed diode laser at 940 nm, an Nd:YAG laser, or an intense pulsed light source operating at an energy density of 30 J/cm$^2$, is suitable for thermally damaging a gland, when a vacuum chamber is attached to the distal end of the handpiece thereof. When vacuum is applied for a few seconds, e.g. 1-10 seconds, above a gland such as a sweat gland, excessive blood is drawn into the gland. After the pulsed laser beam is directed to the skin, the absorption of the laser beam by the drawn blood generates heat in the gland, which is thereby damaged. It is therefore possible to more efficiently thermally damage glands with a laser or intense pulsed light source when vacuum is applied to the skin.

EXAMPLE 7

By placing a vacuum chamber on a skin target in accordance with the present invention prior to the firing of an intense pulsed light source, the treatment energy density level for various types of treatment is significantly reduced with respect with that associated with prior art devices. The treatment energy density level is defined herein as the minimum energy density level which creates a desired change in the skin structure, such as coagulation of a blood vessel, denaturation of a collagen bundle, destruction of cells in a gland, destruction of cells in a hair follicle, or any other desired effects.

The following is the treatment energy density level for various types of treatment performed with use of the present invention and with use of prior art devices:

a) treatment of vascular lesions, port wine stains, telangectasia, rosacea, and spider veins with light emitted from a dye laser unit and having a wavelength of 585 nm: 5-12 J/cm$^2$ (present invention), 10-15 J/cm$^2$ (prior art);

b) treatment of vascular lesions, port wine stains, telangectasia, rosacea, and spider veins with light emitted from a diode laser unit and having a wavelength of 940 nm: 10-30 J/cm$^2$ (present invention), 30-40 J/cm$^2$ (prior art);

c) treatment of vascular lesions with light emitted from an intense pulsed non-coherent light unit and having a wavelength of 570-900 nm: 5-20 J/cm$^2$ (present invention), 12-30 J/cm$^2$ (prior art);

d) treatment of vascular lesions with light emitted from a KPP laser unit manufactured by Laserscope, USA, and having a wavelength of 532 nm: 4-8 J/cm$^2$ (present invention), 8-16 J/cm$^2$ (prior art);

e) photorejuvination with light emitted from a dye laser unit and having a wavelength of 585 nm: 2-4 J/cm$^2$ and requiring 6 treatments (present invention), 2-4 J/cm$^2$ and requiring 12 treatments (prior art);

f) photorejuvination with light emitted from a an intense pulsed non-coherent light unit and having a wavelength ranging from 570-900 nm: 5-20 J/cm$^2$ (present invention), approximately 30 J/cm$^2$ (prior art);

g) photorejuvination with a combined effect of light emitted from an intense pulsed non-coherent light unit and having a wavelength ranging from 570-900 nm and of a RF source: 10 J/cm$^2$ for both the intense pulsed non-coherent light unit and RF source (present invention), 20 J/cm$^2$ for both the intense pulsed non-coherent light unit and RF source (prior art);

h) hair removal with light emitted from a Nd:YAG laser unit and having a wavelength of 1604 nm: 25-35 J/cm$^2$ (present invention), 50-70 J/cm$^2$ (prior art);

i) porphyrin-based photodynamic therapy with light emitting diodes delivering blue light (420 nm), orange light (585 nm), or red light (630 nm) for a treatment duration ranging from 10 msec to 10 min: 5-20 J/cm$^2$ (present invention), 20-30 J/cm$^2$ (prior art).

EXAMPLE 8

A vacuum chamber made of polycarbonate having a length of 50 mm, a width of 25 mm, a height of 3 mm, and a transmitting element made of sapphire was used during the treatment of unwanted hairs of 5 patients with an intense pulsed light system which emitted energy in the spectral band of 670-900 nm. A thin layer of gel at room temperature having a thickness of 0.5 mm was applied to a skin target. The suction openings had a diameter of 1 mm and were formed in the vacuum chamber walls at a height of 0.5 mm below the transmitting element, in order to prevent the obstruction of the openings by gel or by the drawn skin. A small canister serving as a gel trap was provided intermediate to the fluid passage between the vacuum chamber and the vacuum pump, to prevent gel from being drawn to the inlet port of the vacuum pump. A vacuum level of 500 mmHg was generated within the vacuum chamber and caused the skin target to be drawn in contact with the transmitting element.

An intense pulsed light system having a treatment beam length of 40 mm and width of 15 mm was fired with an energy density of 16-20 J/cm$^2$ and a pulse duration of 30-40 milliseconds. One patient underwent a back hair removal treatment, wherein areas of the back were treated as a control without application of a vacuum onto the skin surface and other areas were treated while a vacuum was applied to the skin surface. The other patients underwent a hair removal treatment on their legs, chest and abdomen such that a vacuum was applied to some areas, while the treatment of an adjacent area was not vacuum assisted, as a control. For all five patients, a skin chiller was not employed.

Figure 21:
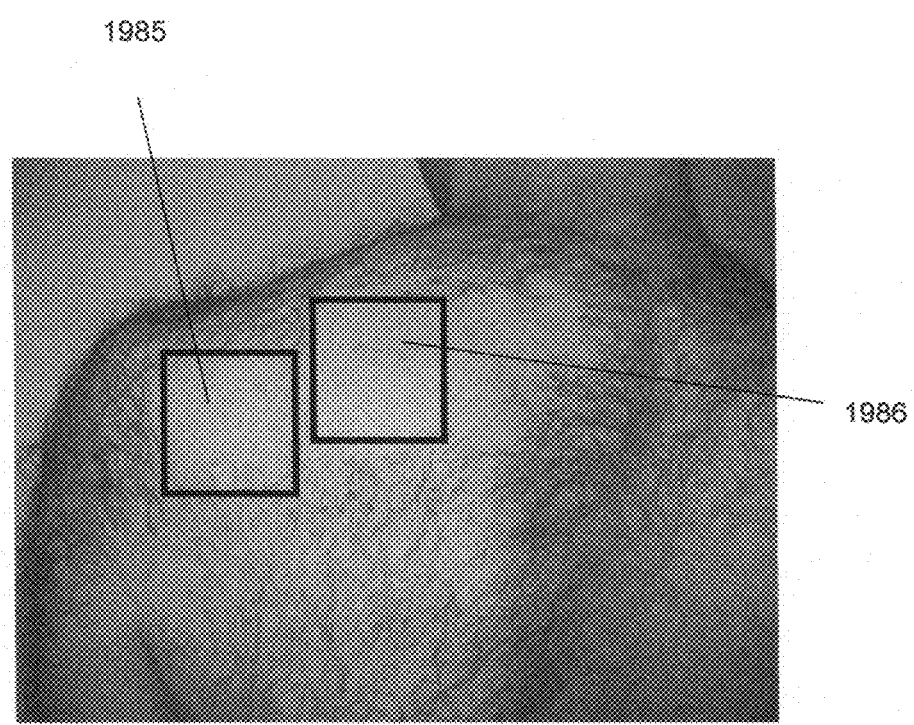
FIG. 21 is a photograph of the back of a patient, illustrating the efficacy of the hair removal treatment of the invention.

FIG. 21 is a photograph which illustrates two back areas 1985 and 1986, respectively, of one of the patients two months after being treated for hair removal. A vacuum was not applied to the skin surface of back area 1985, while a vacuum was applied to the skin surface of back area 1986. As shown, both back areas remained hairless two months after treatment.

The pain sensation of the patients was categorized into five levels: Level 0 indicating that pain was not felt at all, Level 5 indicating that pain was untolerable after a few laser shots whereby a patient grimaced and uncontrollably reacted after each shot, Level 1 indicating that the treatment was sensed but without pain, and Levels 2, 3, and 4 indicating an increasing level of pain. All of the patients consistently suffered Pain Level 3-5 when a vacuum was not applied, and the pain was alleviated (Level 2) or was completely prevented (Level 1 or 0) when a vacuum was applied. Pain alleviation was found to be dependent on the time delay between the application of the vacuum and the firing of the intense pulsed light. Pain alleviation was sensed when the intense pulsed light was fired at least 1.5 seconds after application of the vacuum onto the skin surface.

EXAMPLE 9

A patient undergoing a hair removal treatment was tested for pain sensitivity. An intense pulsed Diode laser (Light Sheer, Lumenis) operating at 810 nm was employed. A vacuum chamber made of polycarbonate having a length of 40 mm, a width of 15 mm, a height of 3 mm, and a transmitting element made of sapphire was used. A thin layer of gel at room temperature having a thickness of 0.5 mm was applied to a skin target. The suction openings had a diameter of 1 mm and were formed in the vacuum chamber walls at a height of 0.5 mm below the transmitting element. A small canister serving as a gel trap was provided intermediate to the fluid passage between the vacuum chamber and the vacuum pump, to prevent gel from being drawn to the inlet port of the vacuum pump.

When a vacuum was not applied to the skin target and the light source operated at an energy density of 42 J/cm$^2$ and a pulse duration of 30 milliseconds, the patient sensed a Pain Level of 5. When a vacuum level of 500 mmHg was generated within the vacuum chamber causing the skin target to be drawn in contact with the transmitting element and the light source operated at an energy density of 42 J/cm$^2$ and a pulse duration of 30 milliseconds, the patient sensed a considerably reduced Pain Level of 2. This reduced pain level during the vacuum assisted treatment was found to be equivalent to the mild pain sensed when the light source operated at an energy density of only 26 J/cm$^2$ and a pulse duration of 30 milliseconds and a vacuum was not applied to the skin target.

EXAMPLE 10

The pain level distribution resulting from a light-based, vacuum-assisted skin flattening skin treatment was compared to that resulting from a conventional light-based skin treatment. Light generated by an IPL Lovely unit manufactured by Msq Ltd., Israel and having an energy density of 18 J/cm$^2$, a wavelength greater than 640 nm, and a pulse duration of 30 msec was directed to 41 different skin targets. Light generated by an Alexandrite laser unit having an energy density of 25 J/cm$^2$ and a pulse duration of 3 msec was directed to 2 different skin targets. Light generated by a diode laser having an energy density of 42 J/cm$^2$ and a pulse duration of 2 msec was directed to 2 different skin targets. To 27 of those skin targets a vacuum of 500 mmHg was applied by means of a vacuum chamber having a planar, 20×50 mm sapphire transmitting element such that the skin target was flattened by the transmitting element. The skin treatment of the remaining 18 targets was performed without generation of a vacuum.

Figure 46:
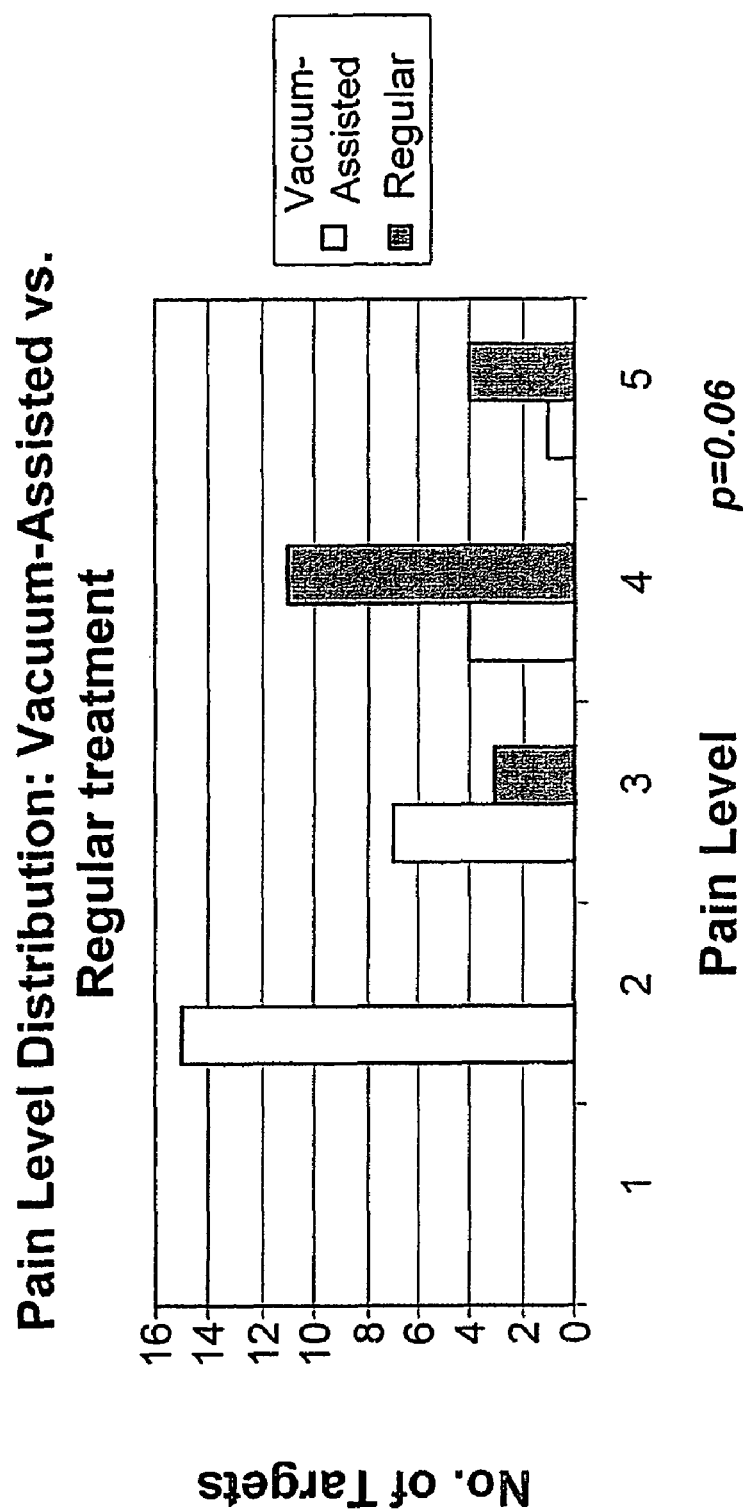
FIG. 46 illustrates a bar chart of the pain level distribution of patients that underwent light-based skin treatments, comparing the pain sensation of a vacuum-assisted treatment with a treatment that was not vacuum-assisted.

FIG. 46 illustrates a bar chart reflecting the pain sensation of patients that underwent each of the 45 skin treatments. The pain sensation was evaluated according to a modified McGill pain questionnaire and was categorized according to the Chi-square statistical technique with a deviation p of 0.06. Of the 18 skin targets that were not subjected to a vacuum, 4 (22.2%) were perceived as having a Pain Level of 5, 11 (61.1%) were perceived as having a Pain Level of 4, and 3 (16.7%) were perceived as having a Pain Level of 3. Of the 27 skin targets that were subjected to a vacuum that is capable of inducing skin flattening, 1 (3.7%) was perceived as having a Pain Level of 5, 4 (14.8%) were perceived as having a Pain Level of 4, 7 (25.9%) were perceived as having a Pain Level of 3, and 15 (55.6%) were perceived as having a Pain Level of 2. Thus the majority of targets which were not subjected to a vacuum perceived a Pain Level of 4, which is very painful, while the majority of targets that were subjected to a vacuum perceived a Pain Level of 2, which is nearly without any pain. A patient undergoing a vacuum-assisted skin flattening skin treatment may therefore anticipate a dramatic pain reduction.

EXAMPLE 11

The influence of the vacuum level during a skin flattening skin treatment on the perceived pain level was tested. Light generated by an IPL Lovely unit manufactured by Msq. Ltd., Israel and having an energy density of 18 J/cm$^2$, a wavelength greater than 640 nm, and a pulse duration of 30 msec was directed to 10 different skin targets. The pain sensation was evaluated according to a modified McGill pain questionnaire. Table II below reflects the average pain level reduction that was perceived for the different vacuum levels that were applied to each of the 10 skin targets.

At a vacuum level of approximately 150 mmHg, the perceived average pain level was 4. The perceived pain level was further reduced to a pain level of 3 when a vacuum level of 300 mmHg was applied, and a significant pain reduction to a pain level of 2 was achieved when a vacuum level of 500 mmHg was applied.

TABLE II

| Applied Vacuum (mmHg) | Level of Pain Reduction |
|---|---|
| 0 | 0 |
| 100 | 0 |
| 200 | 0 |
| 300 | 1 |
| 400 | 1 |
| 500 | 2 |

EXAMPLE 12

The influence of the surface area of the transmitting element during a skin flattening skin treatment on the perceived pain level was tested. Light generated by an IPL Lovely unit manufactured by Msq Ltd., Israel and having an energy density of 18 $J/cm^2$, a wavelength greater than 640 nm, and a pulse duration of 30 msec was directed to 10 different skin targets. Light generated by a diode laser having an energy density of 42 $J/cm^2$ and a pulse duration of 2 msec was directed to 2 different skin targets. The vacuum level that was applied to each of the skin targets was 500 mmHg. The pain sensation was evaluated according to a modified McGill pain questionnaire.

For a transmitting element of 9×9 mm, the average perceived pain level was 3. For a transmitting element of 12×20 mm, the average perceived pain level was a tolerable 2-3. For a transmitting element of 20×40 mm, the average perceived pain level was 1-2, which was nearly without any pain.

EXAMPLE 13

The casing of a tested Wankel type vacuum pump in accordance with the present invention had a width of 50 mm, a length of 50 mm, and a height of 10 mm. The length of the central face slots 8 83A was 20 mm. The rotational speed of the pump rotor was 1500 rpm, or 25 revolutions per second, which was achieved by means of a small brushless motor. At such a rotational speed, the evacuation rate was 18 $cm^3$/sec for an average volume of a vacuum generating compartment of 0.25 $cm^3$. This evacuation rate is suitable for evacuating a vacuum chamber having typical dimensions of 20 mm×40 mm×5 mm height, or a typical volume of 4 $cm^3$, within approximately 0.2 seconds. Since the vacuum needs to be generated prior to the firing of a light-based treatment pulse, the treatment speed was able to exceed a rate of 1 Hz. For a 500-pulse treatment and an average vacuum generation duration of 1 second for each treatment pulse, 12,500 rotor revolutions are needed. Plastic materials with a low friction coefficient of e.g. 0.1 wear only after approximately 50,000 revolutions, and therefore the pump is certainly durable for a 500-pulse treatment.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

The invention claimed is:

1. A dermatological vacuum pump which is in fluid communication with a vacuum chamber placeable on a gel coated skin area and provided with a transmitting element transparent or translucent to pulsed light suitable for effecting a light-based dermatological treatment on the proximate end thereof and with an opening on the distal end thereof, said pump comprising:
  a) an eccentrically rotating rotor having an outer profile of generally equilateral triangular shape with convexly curved faces terminating at an apex, wherein each of said faces is formed with a central face slot adjacent to the centerline of the corresponding face and substantially parallel thereto; and
  b) a casing formed with an epitrochoidal inner wall defining a cavity in which said rotor rotates and being configured such that the apexes of said rotor are in contact with said wall throughout the eccentric angular displacement of said rotor, wherein variably sized compartments defined by the volume within said cavity between said inner wall and a corresponding face of said rotor and through which controlled volumes of air and gel drawn from said vacuum chamber are sequentially transferable to a pump discharge, following operation of said pump, are established, wherein each of said compartments increases from a first volume to a second volume in an intake-expansion cycle to generate a vacuum in said vacuum chamber, decreases from said second volume to a third volume in a compression-exhaust cycle to discharge air and gel, wherein a corresponding rotor face in the vicinity of a central face slot is flexible upon reaction to the force applied thereto by gel that is pressurized within a corresponding compartment during a compression-exhaust cycle.

2. The vacuum pump according to claim 1, wherein the casing is formed with an inlet in communication with a conduit through which air and gel are drawn from the interior of the vacuum chamber to the pump cavity and with an outlet through which the air and gel are discharged to an exhaust tube.

3. The vacuum pump according to claim 2, further comprising an exhaust pipe larger in size than the exhaust tube.

4. The vacuum pump according to claim 3, further comprising means for limiting the vacuum level generated within the vacuum chamber.

5. The vacuum pump according to claim 4, wherein the vacuum level generated within the vacuum chamber is limited by means of remaining atmospheric-pressure not discharged through the exhaust tube or exhaust pipe, said remaining atmospheric-pressure air being transferable to the inlet and mixable with the air drawn from the vacuum chamber.

6. The vacuum pump according to claim 5, wherein the evacuation rate is sufficiently high to allow the completion of a treatment cycle at each treatment site within 1-3 seconds, 2-3 seconds, or less than one second.

7. The vacuum pump according to claim 4, wherein the vacuum level generated within the vacuum chamber is limited to approximately 0.05-0.1 atmospheres.

8. The vacuum pump according to claim 2, further comprising means for restoring the pressure within the vacuum chamber to atmospheric pressure.

9. The vacuum pump according to claim 8, wherein the vacuum chamber pressure is restorable to atmospheric pressure within approximately 0.1 second.

10. The vacuum pump according to claim 8, wherein the rotational direction of the pump is reversible, in order to deliver atmospheric-pressure air to the vacuum chamber.

11. The vacuum pump according to claim 8, which is capable of evacuating air and gel from said vacuum chamber for at least 500 treatment cycles, each of said treatment cycles being characterized by a vacuum generating step, a treatment firing step, and a vacuum release step, and of generating, during each of said treatment cycles, a vacuum level within said vacuum chamber which is suitable for drawing said skin area to said vacuum chamber via said opening.

12. The vacuum pump according to claim 11, wherein the evacuation rate is sufficiently high to allow the completion of a treatment cycle at each treatment site within 3 seconds.

13. The vacuum pump according to claim 1, wherein the vacuum level generated within the vacuum chamber is greater than 500 mm Hg.

14. The vacuum pump according to claim 1, further comprising means for the rotor to conform to the shape of the casing.

15. The method according to claim 1, wherein vacuum is applied from about 0.1 to 6 seconds.

16. A dermatological handpiece system, comprising:
   a) a vacuum chamber placeable on a gel coated skin area and provided with a transmitting element transparent or translucent to pulsed light suitable for effecting a light-based dermatological treatment on the proximate end thereof and with an opening on the distal end thereof;
   b) a handpiece body attached to said vacuum chamber;
   c) a vacuum pump housed in said handpiece body, comprising an eccentrically rotating rotor having an outer profile of generally equilateral triangular shape with convexly curved faces terminating at an apex such that each of said faces is formed with a central face slot adjacent to the centerline of the corresponding face and substantially parallel thereto, and a casing formed with an epitrochoidal inner wall defining a cavity in which said rotor rotates and being configured such that the apexes of said rotor are in contact with said wall throughout the eccentric angular displacement of said rotor;
   d) a conduit in fluid communication with said vacuum chamber and a first port of said pump cavity;
   e) an exhaust tube in communication with a second port of said pump cavity;
   f) a bi-directional motor for driving said pump rotor;
   g) a control unit for said motor;
   h) a power source for said motor and said control unit; and
   i) means in electrical communication with said power source for activating and deactivating said motor, wherein variably sized compartments defined by the volume within said cavity between said inner wall and a corresponding face of said rotor and through which controlled volumes of air and gel drawn from said vacuum chamber via said conduit are sequentially transferable to said exhaust tube, following activation of said motor, are established, wherein each of said compartments increases from a first volume to a second volume in an intake-expansion cycle to generate a vacuum in said vacuum chamber, decreases from said second volume to a third volume in a compression-exhaust cycle to discharge air and gel, wherein a corresponding rotor face in the vicinity of a central face slot is flexible upon reaction to the force applied thereto by gel that is pressurized within a corresponding compartment during a compression-exhaust cycle.

17. The handpiece system according to claim 16, wherein the control unit, following reception of a suitable command, is capable of reversing the rotational direction of the motor and consequently of the rotor, in order to deliver atmospheric-pressure air to the vacuum chamber.

18. The handpiece system according to claim 16, wherein gel discharged from the exhaust tube to a skin area constitutes indication means that a skin target has undergone a light-based treatment.

19. The handpiece system according to claim 16, wherein the means for activating and deactivating the motor are at least one sensor in electrical communication with the control unit.

20. The handpiece system according to claim 16, wherein the handpiece body has a sufficiently small size, low weight and ergonometric design so as to prevent operator fatigue when intermittently held by one hand of an operator for more than one hour during repeated repositioning thereof to different skin areas.

21. The handpiece system according to claim 16, wherein the handpiece body further houses a light source providing the pulsed light.

22. The handpiece system according to claim 21, wherein the control unit is adapted to control the operation of both the vacuum pump and of the light source.

23. The handpiece system according to claim 22, wherein the control unit is suitable for synchronizing in sequence a vacuum generating step, a treatment firing step, and a vacuum release step for each treatment cycle of a corresponding skin area.

24. The handpiece system according to claim 23, wherein the control unit is suitable for synchronizing a predetermined delay ranging from approximately 0.5 sec to approximately 4 seconds between the activation of the vacuum pump and the firing of the source, in order to ensure that a drawn skin area will be in contact with the transmitting element of the vacuum chamber for a sufficiently long nerve inhibiting duration after the light source is fired.

25. The handpiece system according to claim 23, wherein the control unit is also suitable for increasing the pressure in the vacuum chamber to atmospheric pressure by reversing the polarity of the motor following deactivation of the light source.

26. The apparatus according to claim 21, wherein the light source comprises a laser light source, an intense pulsed non-coherent light source, or a light emitting diode light source.

27. The apparatus according to claim 26, wherein the light source is a Q-switched laser suitable for removing tattoos or pigmented lesions.

28. The dermatological handpiece system of claim 16 further comprising a Wankel mechanism to generate a vacuum in a vacuum chamber placed on a gel coated skin area.

29. The dermatological handpiece system of claim 16 further comprising a peristaltic pump to generate a vacuum in a vacuum chamber placed on a gel coated skin area.

30. The dermatological handpiece system of claim 29 wherein the peristaltic pump is attached to a handpiece housing a light source suitable for effecting a light-based vacuum-assisted dermatological treatment.

31. The apparatus according to claim 16, wherein the vacuum pump and the vacuum chamber generate vacuum greater than 150 mmHg.

32. The apparatus according to claim 16, wherein the area of the transmitting element is greater than 100 mm$^2$.

33. An apparatus for alleviating or preventing pain caused by a light-based treatment of a targeted skin structure, comprising:
   a) a non-ablative intense pulsed monochromatic or non-coherent light source for generating any spectral band of light having a wavelength ranging from 400 to 1800 nm;
   b) a vacuum chamber placed on a skin target which is formed with an aperture on the distal end thereof and provided with a transmitting element on the proximate end thereof, the transmitting element being transparent or translucent to the light generated by the light source and suitable for transmitting the light in a direction substantially normal to a skin surface adjoining the skin target;
c) a vacuum pump for applying a vacuum to the vacuum chamber, the level of the applied vacuum suitable for drawing the skin target through the aperture towards, and in a compressing relation against, the transmitting element, whereby to alleviate or prevent the transmission of a pain signal generated by pain receptors located within the skin target; and
d) a gliding apparatus for displacing a distal end of the light source over the transmitting element at a speed ranging from 0.3 to 40 cm/sec.

34. An apparatus for alleviating or preventing pain caused by a light-based treatment of a targeted skin structure, comprising:
a) a non-ablative intense pulsed monochromatic or non-coherent light source for generating any spectral band of light having a wavelength ranging from 400 to 1800 nm;
b) a vacuum chamber placed on a skin target which is formed with an aperture on the distal end thereof and provided with a transmitting element on the proximate end thereof, the transmitting element being transparent or translucent to the light generated by the light source and suitable for transmitting the light in a direction substantially normal to a skin surface adjoining the skin target;
c) a vacuum pump for applying a vacuum to said vacuum chamber, the level of the applied vacuum suitable for drawing the skin target through the aperture towards, and in a compressing relation against, the transmitting element, whereby to alleviate or prevent the transmission of a pain signal generated by pain receptors located within the skin target; and
d) a scanner for scanning by means of the generated light substantially the entire area of the skin target which underlies the transmitting element at a repetition rate of up to 5 pulses/sec.

35. The apparatus according to claim 34, further comprising a pressure sensor in communication with the interior of the vacuum chamber for determining whether the applied vacuum level is sufficient to inhibit the transmission of pain signals.

36. The apparatus according to claim 34, further comprising a skin contact detector for sensing the placement of the vacuum chamber onto the skin target.

37. The apparatus according to claim 36, further comprising an electronic control unit which is suitable for:
a) receiving a first signal from the skin contact sensor upon placement of the vacuum chamber onto the skin target;
b) transmitting a second signal to a vacuum pump actuator to operate the vacuum pump and to initiate a vacuum applying mode;
c) receiving a third signal from a pressure sensor in communication with the interior of the vacuum chamber when the applied vacuum level is sufficient to inhibit the transmission of pain signals;
d) transmitting a fourth signal to a light source controller to trigger operation of the light source or to enable triggering of the light source;
e) receiving a fifth signal from an optical sensor which is adapted to detect the deactivation of the light source; and
f) transmitting a sixth signal to the vacuum pump actuator to initiate a vacuum release mode.

38. The apparatus according to claim 37, further comprising a dissolving solution pump in fluid communication with a dissolving solution reservoir and with a conduit connected to a vacuum pump discharge, for cleaning and dissolving accumulated gel.

39. The apparatus according to claim 38, wherein the control unit is further adapted to transmit a seventh signal to a dissolving solution pump actuator to activate the dissolving solution pump following a predetermined number of cycles of the vacuum applying and vacuum release mode.

40. The apparatus according to claim 37, wherein the duration of the vacuum applying mode ranges from 0.1 to 6 seconds.

41. The apparatus according to claim 34, wherein the vacuum pump is suitable for evacuating air and gel from the vacuum chamber.

42. The apparatus according to claim 34, wherein the transmitting element is chilled.

43. The apparatus according to claim 34, further comprising means for centering a light source distal end with respect to, and above, walls of the vacuum chamber.

44. The apparatus according to claim 34, further comprising means for repositioning the vacuum chamber to another skin target without gaps or overlaps.

45. An apparatus for alleviating or preventing pain caused by a light-based treatment of a targeted skin structure, comprising:
a) a non-ablative intense pulsed monochromatic or non-coherent light source for generating any spectral band of light having a wavelength ranging from 400 to 1800 nm:
b) a vacuum chamber placed on a skin target which is formed with an aperture on the distal end thereof and provided with a transmitting element on the proximate end thereof, the transmitting element being transparent or translucent to the light generated by the light source and suitable for transmitting the light in a direction substantially normal to a skin surface adjoining the skin target; and
c) a vacuum pump for applying a vacuum to said vacuum chamber, the level of the applied vacuum suitable for drawing the skin target through the aperture towards, and in a compressing relation against, the transmitting element, whereby to alleviate or prevent the transmission of a pain signal generated by pain receptors located within the skin target;
wherein the vacuum pump is a rotary pump having an eccentrically rotating rotor having an outer profile of generally equilateral triangular shape with convexly curved faces terminating at an apex, each of said faces being formed with a central face slot adjacent to the centerline of the corresponding face and substantially parallel thereto.

* * * * *